(12) United States Patent
Hateboer et al.

(10) Patent No.: US 7,604,960 B2
(45) Date of Patent: Oct. 20, 2009

US007604960B2

(54) TRANSIENT PROTEIN EXPRESSION METHODS

(75) Inventors: Guus Hateboer, Heemstede (NL);
Menzo J. E. Havenga, Alphen a/d Rijn (NL); Ronald Vogels, Linschoten (NL);
Lennart Holterman, Zoetermeer (NL)

(73) Assignee: Crucell Holland B.V., Leiden (NL)

( * ) Notice: Subject to any disclaimer, the term of this patent is extended or adjusted under 35 U.S.C. 154(b) by 39 days.

(21) Appl. No.: 11/809,697

(22) Filed: Jun. 1, 2007

(65) Prior Publication Data

US 2008/0113409 A1 May 15, 2008

Related U.S. Application Data

(60) Continuation-in-part of application No. 11/592,409, filed on Nov. 3, 2006, now Pat. No. 7,470,523, which is a division of application No. 10/234,007, filed on Sep. 3, 2002, now Pat. No. 7,132,280, which is a division of application No. 09/549,463, filed on Apr. 14, 2000, now Pat. No. 6,855,544.

(60) Provisional application No. 60/129,452, filed on Apr. 15, 1999.

(51) Int. Cl.
*C12P 21/06* (2006.01)
*C12N 15/00* (2006.01)
*C12N 15/861* (2006.01)

(52) U.S. Cl. .................. 435/69.1; 435/320.1; 435/455; 424/233.1

(58) Field of Classification Search ........................ None
See application file for complete search history.

(56) References Cited

U.S. PATENT DOCUMENTS

| | | | |
|---|---|---|---|
| 4,703,008 A | 10/1987 | Lin | |
| 4,835,260 A | 5/1989 | Shoemaker | |
| 5,047,335 A | 9/1991 | Paulson et al. | |
| 5,192,539 A | 3/1993 | Van Der Marel et al. | |
| 5,441,868 A | 8/1995 | Lin | |
| 5,457,089 A | 10/1995 | Fibi et al. | |
| 5,494,790 A | 2/1996 | Sasaki et al. | |
| 5,631,158 A | 5/1997 | Dorai et al. | |
| 5,767,078 A | 6/1998 | Johnson et al. | |
| 5,773,569 A | 6/1998 | Wrighton et al. | |
| 5,789,247 A | 8/1998 | Ballay et al. | |
| 5,830,851 A | 11/1998 | Wrighton et al. | |
| 5,835,382 A | 11/1998 | Wilson et al. | |
| 5,856,298 A | 1/1999 | Strickland | |
| 5,994,128 A | 11/1999 | Fallaux et al. | |
| 6,033,908 A | 3/2000 | Bout et al. | |
| 6,037,453 A | 3/2000 | Jardieu et al. | |
| 6,475,753 B1 | 11/2002 | Ruben et al. | |
| 6,492,169 B1 | 12/2002 | Vogels et al. | |
| 6,558,948 B1 | 5/2003 | Kochanek et al. | |
| 6,653,101 B1 | 11/2003 | Cockett et al. | |
| 6,855,544 B1 | 2/2005 | Hateboer et al. | |
| 6,878,549 B1 | 4/2005 | Vogels et al. | |
| 2002/0116723 A1 | 8/2002 | Grigliatti et al. | |
| 2003/0087437 A1 | 5/2003 | Asada et al. | |
| 2003/0092160 A1 | 5/2003 | Bout et al. | |

FOREIGN PATENT DOCUMENTS

| | | |
|---|---|---|
| EP | 0 185 573 | 6/1986 |
| EP | 0 411 678 | 2/1991 |
| EP | 0 833 934 B1 | 4/1998 |
| WO | WO 93/03163 | 2/1993 |
| WO | WO 95/05465 | 2/1995 |
| WO | WO 95/29994 | 11/1995 |
| WO | WO 97/00326 | 1/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 99/24068 | 5/1999 |
| WO | WO 00/61164 | 10/2000 |
| WO | WO 00/63403 | 10/2000 |
| WO | WO 01/38362 A2 | 5/2001 |
| WO | WO 02/053580 | 7/2002 |
| WO | WO 03/038100 A1 | 5/2003 |
| WO | WO 03/048197 A1 | 6/2003 |
| WO | WO 03/048348 A2 | 6/2003 |
| WO | WO 03/051927 | 6/2003 |
| WO | WO 2004/003176 | 1/2004 |
| WO | WO 2004/099396 | 11/2004 |
| WO | WO 2007/134325 | 11/2007 |

OTHER PUBLICATIONS

Zhou et al. Journal of Virology, 1996, 70(10):7030-7038.*
Alkhatib et al., "Expression of Bicistronic Measles Virus P/C mRNA by Using Hybrid Adenovirus: Levels of C Protein Synthesized In Vivo Are Unaffected by the Presence or Absence of the Upstream P Initiator Codon," Journal of Virology, Nov. 1988, pp. 4059-4068, vol. 62, No. 11.

(Continued)

*Primary Examiner*—Stacy B Chen
(74) *Attorney, Agent, or Firm*—TraskBritt

(57) ABSTRACT

Described is a method for producing a protein of interest, the method comprising: a) providing a recombinant adenoviral vector comprising nucleic acid encoding the protein of interest under control of a promoter, wherein the adenoviral vector has deletions in a first region and in a second region of the adenovirus genome, wherein each of the first region and the second region is required for adenoviral genome replication and/or adenovirus particle formation, b) propagating the adenoviral vector in a first type of complementing cells that express proteins from the first and from the second region of the adenovirus genome so as to complement the deletions of the recombinant adenoviral vector, to obtain recombinant adenovirus particles, c) infecting a culture of a second type of complementing cells with the recombinant adenovirus particles, wherein the second type of complementing cells express protein from the first region of the adenovirus genome but not protein from the second region of the adenovirus genome, to produce the protein of interest, and d) harvesting the protein of interest.

20 Claims, 11 Drawing Sheets

OTHER PUBLICATIONS

Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.

Berg et al., High-Level Expression of Secreted Proteins from Cells Adapted to Serum-Free Suspension Culture, Research Report, 1993, pp. 972-978, vol. 14, No. 6.

Bout et al., "Improved helper cells for RCA-free production of E1-deleted recombinant adenovirus vectors," Cancer Gene Therapy, 1996, pp. S24, vol. 3, No. 6.

Bout et al., "Production of RCA-free batches of E1-deleted recombinant adenoviral vectors on PER.C6," Nucleic Acids Symp. Ser. 1998, XP-002115716, pp. 35-36.

Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.

Brown et al., "Evaluation of Cell Line 293 for Virus isolation in Routine Viral Diagnosis," Journal of Clinical Microbiology, Apr. 1986, pp. 704-708, vol. 23, No. 4.

Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.

Caravokri et al., "Constitutive Episomal Expression of Polypeptide I X (pIX) in a 293-Based Cell Line Complements that Deficiency of pIX Mutant Adenovirus Type 5," Journal of Virology, Nov. 1995, pp. 6627-6633, vol. 69, No. 11.

Carroll et al., Abstract, Differential Infection of Receptor-modified Host Cells by Receptor-Specific Influenza Viruses, Virus Research, Sep. 1985, pp. 165-179, vol. 3, No. 2.

Ciccarone et al., "Lipofectamine 2000 Reagent for Transfection of Eukaryotic Cells," Focus, 1999, pp. 54-55, vol. 21, No. 2.

Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.

Cronan, Abstract, Biotination of Proteins in-vivo a post-translational modification to label purify and study proteins, Journal of Biological Chemistry, Jun. 25, 1990, pp. 10327-10333, vol. 265, No. 18.

DuBridge et al., "Analysis of Mutation in Human Cells by Using an Epstein-Barr Virus Shuttle System," Molecular and Cellular Biology, Jan. 1987, pp. 397-387, vol. 7, No. 1.

Endo et al., Growth of Influenza A Virus in Primary, Differentiated Epithelial Cells Derived from Adenoids, Journal of Virology, Mar. 1996, pp. 2055-2058, vol. 70, No. 3.

European Search Report 05 10 0732, Apr. 7, 2005.

Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917. Abstract.

Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7.

Gallimore et al., Transformation of Human Embryo Retinoblasts with Simian Virus 40, Adenovirus and ras Oncogenes, Anticancer Research, 1986, pp. 499-508, vol. 6.

Garnier et al. Scale-up of the adenovirus expression system for the production of recombinant protein in human 293S cells, Cytotechnology, 1994, pp. 145-155, vol. 15.

GenBank Accession No. X02996.1, 1993, "Adenovirus type 5 left 32% of the genome."

Ghosh-Choudhury et al., Protein IX, a minor component of the human adenovirus capsid, is essential for the packaging of the full length genomes, The EMBO Journal, 1987, pp. 1733-1739, vol. 6, No. 6.

Grabenhorst et al., Construction of stable BHK-21 cells coexpressing human secretory glycoproteins and human Gal(beta-1-4)G1cNAc-R alpha-2,6-sialyltransferase alpha-2,6-Linked NeuAc is preferentially attached to the Gal(beta-1- 4)G1cNAc(beta-1-2)Man(alpha-1-3)-branch of diantennary oligosaccharides from secreted recombinant beta-trace protein, Eur. J. Biochem, 1995, pp. 718-725, vol. 232, No. 3, Berlin, Germany.

Graham et al., "Characteristics of a Human Cell Line Transformed by DNA from Human Adenovirus Type 5," J. Gen. Virol., 1977, pp. 59-72, vol. 36.

Graham et al., "Growth of 293 cells in suspension culture," J Gen Virol, Mar. 1987, pp. 937-940, vol. 68.

Graham, Cell Lines, Promochem (visited Apr. 10, 2005) <http://www.lgcpromochem-atcc.com/SearchCatalogs/longview.cfm?view=ce,1146678...>.

Grand et al., "Modulation of the level of expression of cellular genes in adenovirus 12-infected and transformed human cells," Eur Mol Biol Organ J. 1986, 5 (6) 1253-1260. Abstract.

Grand et al., "The high levels of p53 present in adenovirus early region 1-transformed human cells do not cause up-regulation of MDM2 expression," Virology, 1995, vol. 210, No. 2, pp. 323-334. Abstract.

Hollister et al., Stable expression of mammalian beta1,4-galactosyltransferase extends the N-glycosylation pathway in insect cells, Glycobiology, 1998, pp. 473-480, vol. 8, No. 5, IRL Press, United Kingdom.

Holzer et al., "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.

Inoue et al., Production of Recombinant Human Monoclonal Antibody Using ras-Amplified BHK-21 Cells in a Protein-free Medium, Biosci. Biotech. Biochem., 1996, pp. 811-817, vol. 60, No. 5.

Interlocutory Decision of the Opposition Division of Jul. 21, 2003 in the case EP 0 695 351(European application 94 913 174.2).

Jenkins et al., Getting the glycosylation right: Implications for the biotechnology industry, Nature Biotechnology, Aug. 1996, pp. 975-981, vol. 14, No. 8, Nature Publishing, US.

Lopez et al., Efficient production of biologically active human recombinant proteins in human lymphoblastoid cells form integrative and episomal expression vectors, Gene, 1994, pp. 285-291, vol. 148.

Louis et al., Cloning and Sequencing of the Cellular—Viral Junctions from the Human Adenovirus Type 5 Transformed 293 Cell Line, Virology, 1997, pp. 423-429, vol. 233.

Lutz et al., "The Product of the Adenovirus Intermediate Gene IX Is a Transcriptional Activator," Journal of Virology, Jul. 1997, pp. 5102-5109, vol. 71, No. 7.

Manservigi et al., "Protection from Herpes Simplex Virus Type 1 Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Merten et al., Production of Influenza Virus in Cell Cultures for Vaccine Preparation, Exp Med Biol., 1996, pp. 141-151, vol. 397.

Minch et al., Tissue Plasminogen Activator Coexpressed in Chinese Hamster Ovary Cells with alpha(2,6)-Sialyltransferase Contains NeuAc-alpha(2,6)Gal-beta(1,4)G1c-N-AcR Linkages, Biotechnol. Prog., 1995, pp. 348-351, vol. 11, No. 3.

Neumann et al., "Generation of influenza A viruses entirely from cloned cDNAs," Proc. Natl. Acad. Sci., Aug. 1999, pp. 9345-9350, vol. 96.

Opposition against European patent 1 108 787 B1 filed Oct. 5, 2005 in the name and on behalf of CEVEC Pharmaceuticals GmbH.

Opposition against European patent 1 161 548 B1 filed Nov. 16, 2005, in the name and on behalf of CEVEC Pharmaceutical GmbH.

Opposition against European patent 1108787 filed Oct. 5, 2005 in the name and on behalf of Probiogen AG.

ORY et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Parkinson et at., "Stable Expression of a Secretable Deletion Mutant of Recombinant Human Thrombomodulin in Mammalian Cells," The Journal of Biological Chemistry, Jul. 25, 1990, pp. 12602-12610. vol. 265, No. 21.

Pau et al., Abstract, The human cell line PER.C6 provides a new manufacturing system for the production of influenza vaccines, Vaccine, Mar. 21, 2001, pp. 2716-2721, vol. 19, No. 17-19.

Paul et al., Increased Viral Titer Through Concentration of Viral Harvests from Retroviral Packaging Lines, Human Gene Therapy, 1993, pp. 609-615, vol. 4.

Pazur et al., Abstract, Oligosaccharides as immunodeterminants of erythropoietin for two sets of anti-carbohydrate antibodies, Journal of Protein Chemistry, Nov. 2000, pp. 631-635, vol. 19, No. 8.

PCT International Search Report, PCT/NL00/00247, dated Oct. 9, 2000, 3 pages.

Pleschka et al., "A Plasmid-Based Reverse Genetics System for Influenza A Virus," Journal of Virology, Jun. 1996, pp. 4188-4192, vol. 70, No. 6.

PubMed listing of abstracts (visited Apr. 10, 2005) <http://www.ncbi.nlm.nih.gov/entrez/query.fcgi?CMD=search&DB=pubmed.

Reina et al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Schiedner et al., Abstract, Efficient transformation of primary human amniocytes by E1 functions of Ad5: generation of new cell lines for adenoviral vector production, 2000, Hum. Gene Ther. 11, 2105-2116.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Yallop et al., "PER.C6® Cells for the Manufacture of Biopharmaceutical Proteins," Modern Biopharmaceuticals, Ed. J. Knablein, 2005, Wiley-VCH Verlag GmbH & Co. KGaA, Weinheim, Germany.

Yan et al., Novel Asn-linked oligosaccharides terminating in GalNAcbeta(1-4)[Fucalpha(1-3)]GlcNAcbeta(1-.) are present in recombinant human Protein C expressed in human kidney 293 cells, Glycobiology, 1993, pp. 597-608, vol. 3. No. 6.

Yeager et al., Constructing immortalized human cell lines, Current Opinion Biotechnology, 1999, pp. 465-469, vol. 10.

Yu et al., "Enhanced c-erbB-2/neu expression in human ovarian cancer cells correlates with more severe malignancy that can be suppressed by E1A," Cancer Res., 1993, 53 (4) 891-8. Abstract.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

Opposition against EP 1 161 548 filed with EPO on Oct. 8, 2007, 12 pages.

Rhim, Johng S., Development of Human Cell Lines from Multiple Organs, Annals of the New York Academy of Sciences, 2000, pp. 16-25, vol. 919.

* cited by examiner

A: Generation of ΔE1/ΔE2A deficient adenoviruses

B: Transient protein production in absence of virus replication

TRANSIENT PROTEIN EXPRESSION METHODS

CROSS-REFERENCE TO RELATED APPLICATIONS

This application is a continuation-in-part of U.S. patent application Ser. No. 11/592,409, filed Nov. 3, 2006 now U.S. Pat. No. 7,470,523, the contents of the entirety of which is incorporated by this reference, which is a divisional of U.S. patent application Ser. No. 10/234,007, filed Sep. 3, 2002, now U.S. Pat. No. 7,132,280, issued Nov. 7, 2006, the contents of the entirety of which, including its sequence listing, is incorporated by this reference, which is a divisional of U.S. patent application Ser. No. 09/549,463, filed Apr. 14, 2000, now U.S. Pat. No. 6,855,544, issued Feb. 15, 2005, the entire contents of which, including its sequence listing, is incorporated by this reference, which application claims priority under 35 U.S.C. Section 119(e) to Provisional Patent Application Ser. No. 60/129,452 filed Apr. 15, 1999.

TECHNICAL FIELD

The invention relates generally to biotechnology and recombinant protein production, more particularly to the use of a human cell for the production of proteins. The invention is particularly useful for the production of proteins that benefit from post-translational or peri-translational modifications such as glycosylation and proper folding.

BACKGROUND

The expression of human recombinant proteins in heterologous cells has been well documented. Many production systems for recombinant proteins have become available, ranging from bacteria, yeasts, and fungi to insect cells, plant cells and mammalian cells. However, despite these developments, some production systems are still not optimal, or are only suited for production of specific classes of proteins. For instance, proteins that require post- or peri-translational modifications such as glycosylation, γ-carboxylation, or hydroxylation cannot be produced in prokaryotic production systems. Another well-known problem with prokaryotic expression systems is the incorrect folding of the product to be produced, even leading to insoluble inclusion bodies in many cases.

Eukaryotic systems are an improvement in the production of, in particular, eukaryote derived proteins, but the available production systems still suffer from a number of drawbacks. The hypermannosylation in, for instance, yeast strains affects the ability of yeasts to properly express glycoproteins. Hypermannosylation often even leads to immune reactions when a therapeutic protein thus prepared is administered to a patient. Furthermore, yeast secretion signals are different from mammalian signals, leading to a more problematic transport of mammalian proteins, including human polypeptides, to the extracellular, which in turn results in problems with continuous production and/or isolation. Mammalian cells are widely used for the production of such proteins because of their ability to perform extensive post-translational modifications. The expression of recombinant proteins in mammalian cells has evolved dramatically over the past years, resulting in many cases in a routine technology.

In particular, Chinese hamster ovary cells ("CHO cells") have become a routine and convenient production system for the generation of biopharmaceutical proteins and proteins for diagnostic purposes. A number of characteristics make CHO cells very suitable as a host cell. The production levels that can be reached in CHO cells are extremely high. The cell line provides a safe production system, which is free of infectious or virus-like particles. CHO cells have been extensively characterized, although the history of the original cell line is vague. CHO cells can grow in suspension until reaching high densities in bioreactors, using serum-free culture media; a dhfr-mutant of CHO cells (DG-44 clone, Urlaub et al., 1983) has been developed to obtain an easy selection system by introducing an exogenous dhfr gene and thereafter a well-controlled amplification of the dhfr gene and the transgene using methotrexate.

However, glycoproteins or proteins comprising at least two (different) subunits continue to pose problems. The biological activity of glycosylated proteins can be profoundly influenced by the exact nature of the oligosaccharide component. The type of glycosylation can also have significant effects on immunogenicity, targeting and pharmacokinetics of the glycoprotein. In recent years, major advances have been made in the cellular factors that determine the glycosylation, and many glycosyl transferase enzymes have been cloned. This has resulted in research aimed at metabolic engineering of the glycosylation machinery (Fussenegger et al., 1999; Lee et al., 1989; Vonach et al., 1998; Jenikins et al., 1998; Zhang et al., 1998; Muchmore et al., 1989). Examples of such strategies are described herein.

CHO cells lack a functional α-2,6 sialyl-transferase enzyme, resulting in the exclusive addition of sialyc acids to galactose via α-2,3 linkages. It is known that the absence of α-2,6 linkages can enhance the clearance of a protein from the bloodstream. To address this problem, CHO cells have been engineered to resemble the human glycan profile by transfecting the appropriate glycosyl transferases. CHO cells are also incapable of producing Lewis X oligosaccharides. CHO cell lines have been developed that express human N-acetyl-D-glucosaminyltransferase and α-1,3-fucosyl-transferase III. In contrast, it is known that rodent cells, including CHO cells, produce CMP-N-acetylneuraminic acid hydrolase which lead to CMP-N-acetylneuraminic acids (Jenkins et al., 1996), an enzyme that is absent in humans. The proteins that carry this type of glycosylation can produce a strong immune response when injected (Kawashima et al., 1993). The recent identification of the rodent gene that encodes the hydrolase enzyme will most likely facilitate the development of CHO cells that lack this activity and will avoid this rodent-type modification.

Thus, it is possible to alter the glycosylation potential of mammalian host cells by expression of human glucosyl transferase enzymes. Yet, although the CHO-derived glycan structures on the recombinant proteins may mimic those present on their natural human counterparts, a potential problem exists in that they are still found to be far from identical. Another potential problem is that not all glycosylation enzymes have been cloned and are, therefore, available for metabolic engineering. The therapeutic administration of proteins that differ from their natural human counterparts may result in activation of the immune system of the patient and cause undesirable responses that may affect the efficacy of the treatment. Other problems using non-human cells may arise from incorrect folding of proteins that occurs during or after translation, which might be dependent on the presence of the different available chaperone proteins. Aberrant folding may occur, leading to a decrease or absence of biological activity of the protein. Furthermore, the simultaneous expression of separate polypeptides that will together form proteins comprised of the different subunits, like monoclonal antibodies, in correct relative abundancies is of great importance.

Human cells will be better capable of providing all necessary facilities for human proteins to be expressed and processed correctly.

It would thus be desirable to have methods for producing human recombinant proteins that involve a human cell that provides consistent human-type processing like post-translational and peri-translational modifications, such as glycosylation, which preferably is also suitable for large-scale production.

SUMMARY OF THE INVENTION

Described are, among other things, methods and compositions for producing recombinant proteins in a human cell line. The methods and compositions are particularly useful for generating stable expression of human recombinant proteins of interest that are modified post-translationally, for example, by glycosylation. Such proteins are believed to have advantageous properties in comparison with their counterparts produced in non-human systems such as Chinese hamster ovary cells.

Provided are methods for producing at least one proteinaceous substance in a cell including a eukaryotic cell having a sequence encoding at least one adenoviral E1 protein or a functional homologue, fragment and/or derivative thereof in its genome, which cell does not encode a structural adenoviral protein from its genome or a sequence integrated therein, the method including providing the cell with a gene encoding a recombinant proteinaceous substance, culturing the cell in a suitable medium and harvesting at least one proteinaceous substance from the cell and/or the medium. A proteinaceous substance is a substance including at least two amino-acids linked by a peptide bond. The substance may further include one or more other molecules physically linked to the amino acid portion or not. Non-limiting examples of such other molecules include carbohydrate and/or lipid molecules.

A nucleic acid sequence encoding an adenovirus structural protein should not be present in the genome of the cell line for a number of reasons. One reason is that the presence of an adenoviral structural protein in a preparation of produced protein is highly undesired in many applications of such produced protein. Removal of the structural protein from the product is best achieved by avoiding its occurrence in the preparation. Preferably, the eukaryotic cell is a mammalian cell. In a preferred embodiment, the proteinaceous substance harvested from the cell and the cell itself is derived from the same species. For instance, if the protein is intended to be administered to humans, it is preferred that both the cell and the proteinaceous substance harvested from the cell are of human origin. One advantage of a human cell is that most of the commercially most attractive proteins are human.

The proteinaceous substance harvested from the cell can be any proteinaceous substance produced by the cell. In certain embodiments, at least one of the harvested proteinaceous substances is encoded by the gene. In other embodiments, a gene is provided to the cell to enhance and/or induce expression of one or more endogenously present genes in a cell, for instance, by providing the cell with a gene encoding a protein that is capable of enhancing expression of a proteinaceous substance in the cell.

As used herein, a "gene" is a nucleic acid sequence including a nucleic acid sequence of interest in an expressible format, such as an expression cassette. The nucleic acid sequence of interest may be expressed from the natural promoter or a derivative thereof or an entirely heterologous promoter. The nucleic acid sequence of interest can include introns or not. Similarly, it may be a cDNA or cDNA-like nucleic acid. The nucleic acid sequence of interest may encode a protein. Alternatively, the nucleic acid sequence of interest can encode an anti-sense RNA.

Further provided is a method for producing at least one human recombinant protein in a cell, including providing a human cell having a sequence encoding at least an immortalizing E1 protein of an adenovirus or a functional derivative, homologue or fragment thereof in its genome, which cell does not produce structural adenoviral proteins, with a nucleic acid encoding the human recombinant protein. The method involves culturing the cell in a suitable medium and harvesting at least one human recombinant protein from the cell and/or the medium. Until the invention, few, if any, human cells exist that have been found suitable to produce human recombinant proteins in any reproducible and upscaleable manner. We have now found that cells which include at least immortalizing adenoviral E1 sequences in their genome are capable of growing (they are immortalized by the presence of E1) relatively independent of exogenous growth factors. Furthermore, these cells are capable of producing recombinant proteins in significant amounts and are capable of correctly processing the recombinant protein being made. Of course, these cells will also be capable of producing non-human proteins. The human cell lines that have been used to produce recombinant proteins in any significant amount are often tumor (transformed) cell lines. The fact that most human cells that have been used for recombinant protein production are tumor-derived adds an extra risk to working with these particular cell lines and results in very stringent isolation procedures for the recombinant protein in order to avoid transforming activity or tumorigenic material in any protein or other preparations. According to the invention, it is, therefore, preferred to employ a method wherein the cell is derived from a primary cell. In order to be able to grow indefinitely, a primary cell needs to be immortalized in some kind, which, in the invention, has been achieved by the introduction of adenovirus E1.

BRIEF DESCRIPTION OF THE DRAWINGS

Figure 3:
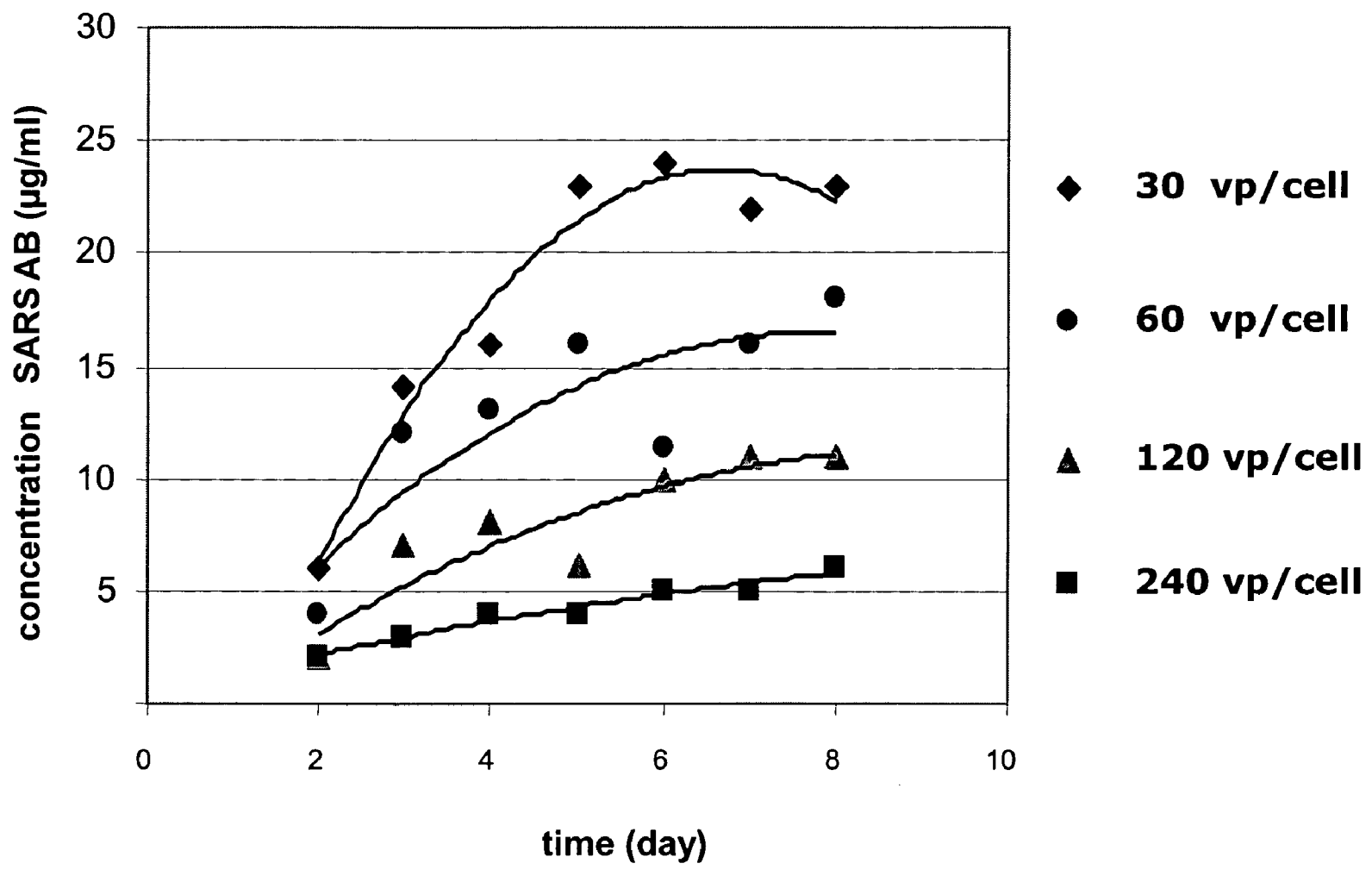

FIG. 3. Virus mediated SARS-AB production in PER.C6 cells after infection with various MOI's of Ad5.dE1.dE2A.SARS-AB viruses. Five similar PER.C6 cultures (shaker flasks) were infected in parallel with 0, 30, 60, 120 or 240 vp/cell Ad5.dE1.dE2A.SARS-AB. SARS-AB concentration in medium samples was determined using HPLC-protA column chromatography standardized for IgG quantity measurement. See example 36 for details.

FIG. 5. Virus-mediated SARS-AB production in PER.C6 culture medium after infection with either purified or crude lysate preparations of Ad5.dE1.dE2A.SARS-AB viruses. Two similar cell cultures were infected in parallel with $1 \times 10^9$ infectious virus particles (4 IU/cell) of either CsCl-purified vector (triangles) or with crude lysates containing the vector (squares). See example 36 for details.

B) Binding of SARS-AB to S565. Two different SARS-AB batches (SARS-AB-1 and SARS-AB-2), both produced in PERC.6 cells, after infection with purified virus and crude lysate respectively, were tested and compared to CR3014, a positive control SARS-AB. Amount of SARS-AB bound to S565 was detected after staining with by FACS. See example 37 for details.

Figure 8:
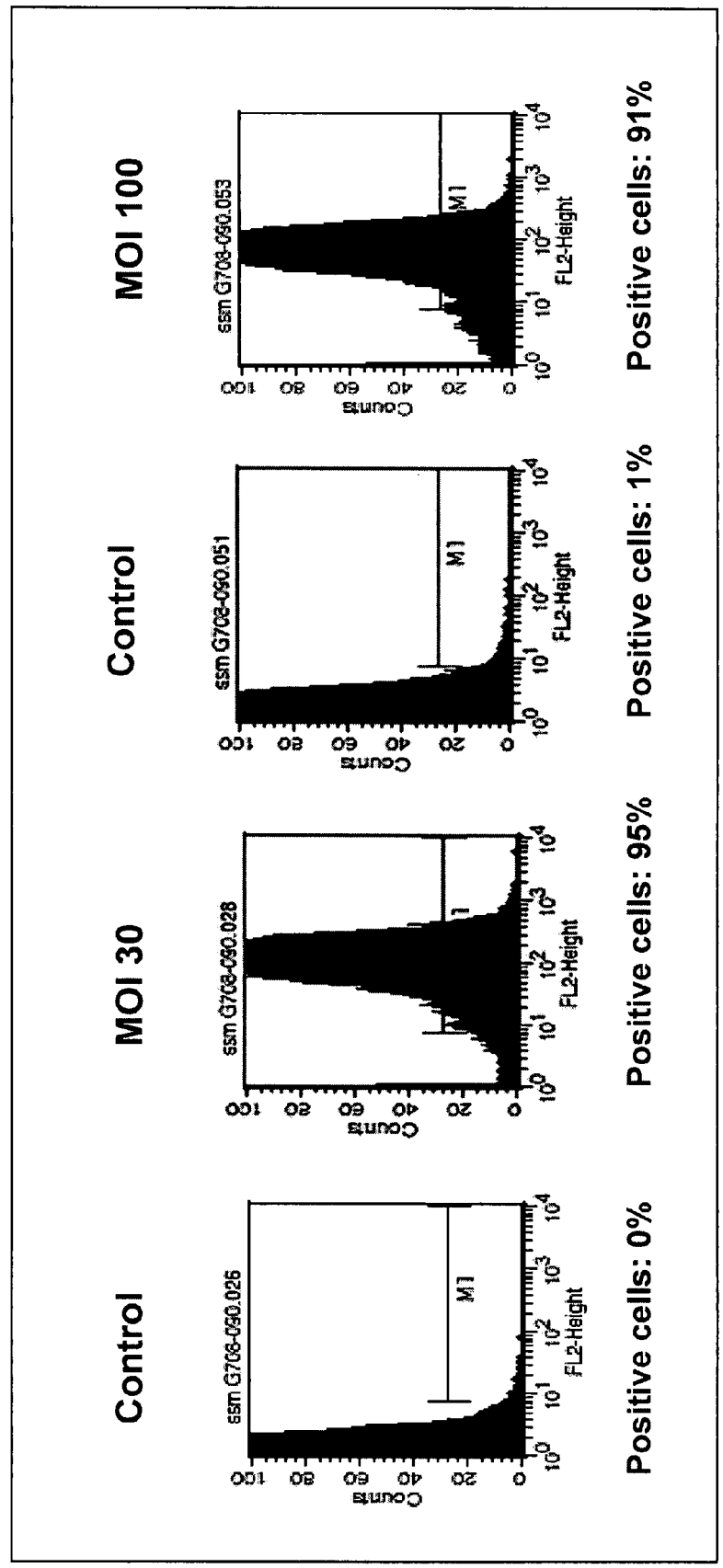

FIG. 8. FACS analysis demonstrating the ability of S1-spike to bind SARS-AB. S1-spike was transiently expressed in PER.C6 cells after infection with 30 and 100 vp/cell of Ad5.dE1.dE2A.S1-spike. Binding of transiently produced SARS-AB was analyzed by FACS after mouse-anti-c-myc-FITC Mab binding. Infected PER.C6 cells (both MOI's) stained only with mouse-anti-c-myc-FITC (no SARS-AB) are depicted as negative controls. See example 37 for details.

Figure 9:
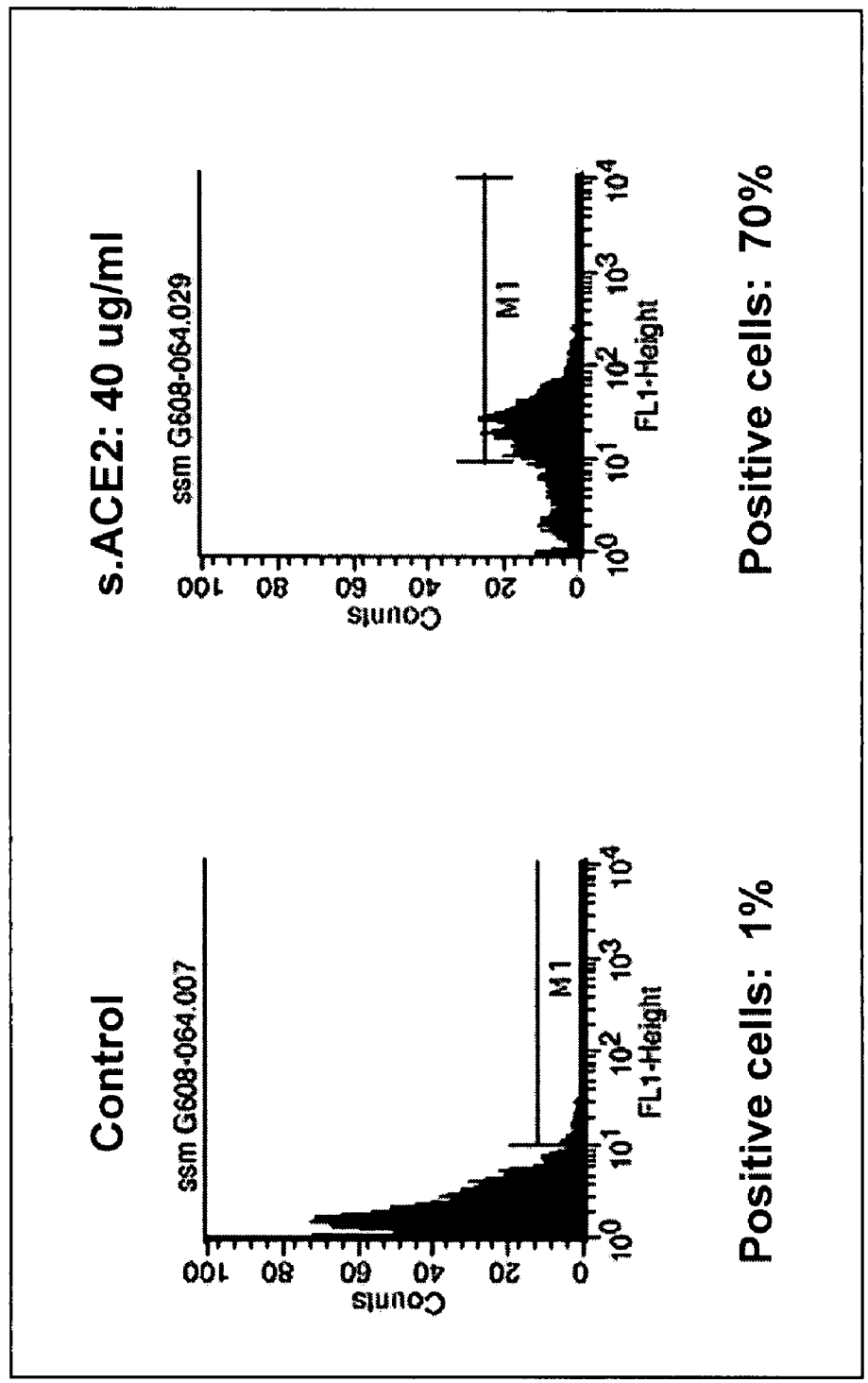

FIG. 9. FACS analysis demonstrating s.ACE2 binding to S1-spike. S1-spike was transiently expressed in PER.C6 cells using Ad5.dE1.dE2A.S1-spike. FACS staining was performed using transiently produced s.ACE2 (40 µg/ml) and subsequently stained with mouse-anti-c-myc-FITC Mab. Infected PER.C6 cells stained only with mouse-anti-c-myc-FITC are depicted as negative controls. See example 37 for details.

Figure 10:
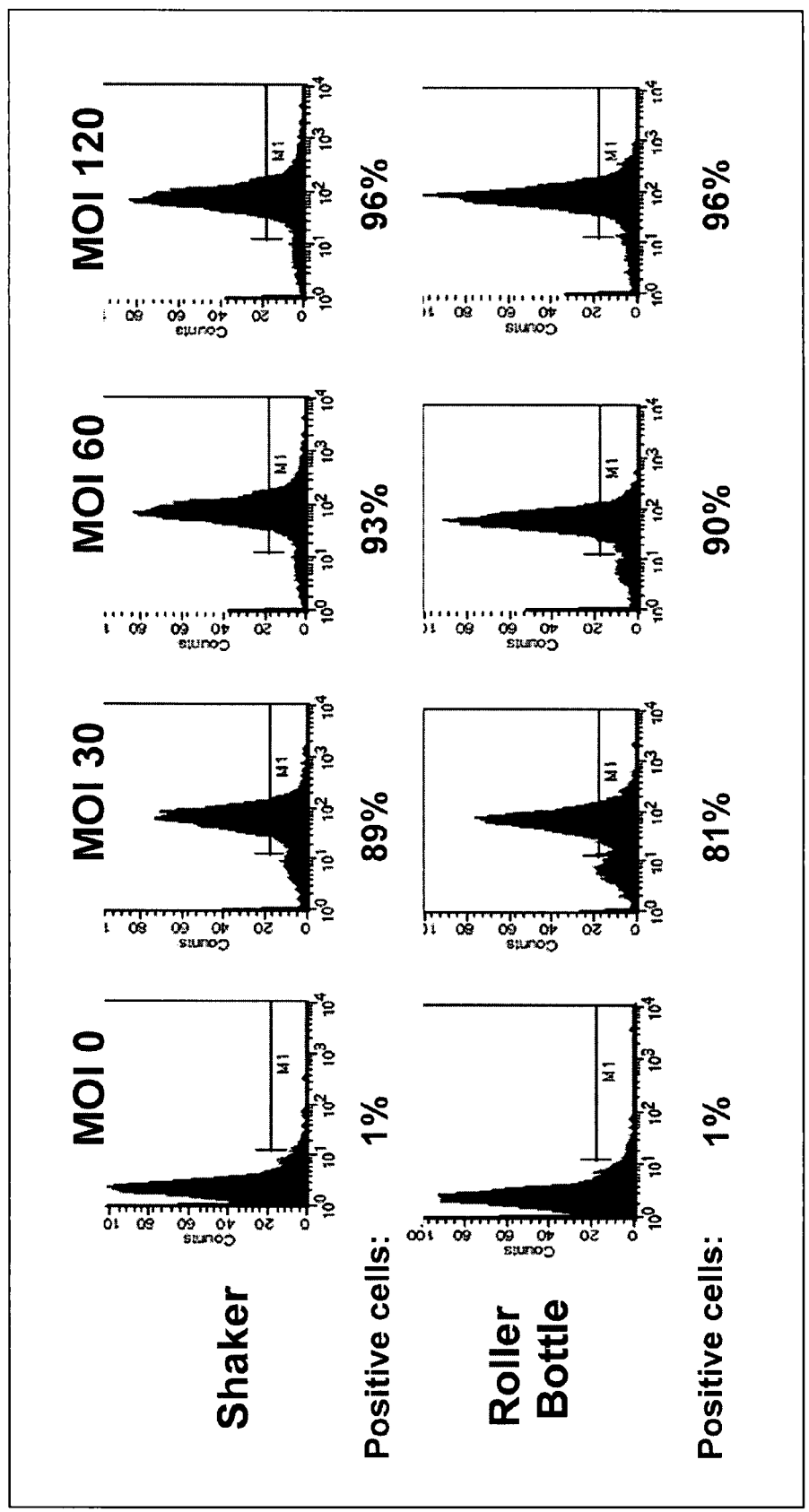

FIG. 10. Analysis of transiently expressed ACE2 on cell membranes of PER.C6 cells. Shaker flasks and roller bottles were infected in parallel with MOI 0, 30, 60 and 120 vp/cell Ad5.dE1.dE2A.ACE2 viruses. For FACS analysis cells were stained with anti-SARSspike IgG and PE-conjugated anti-human IgG (100-fold dilution). Uninfected PER.C6 similarly stained were used as negative control. See example 37 for details.

DETAILED DESCRIPTION

In order to achieve large-scale (continuous) production of recombinant proteins through cell culture, it is preferred to have cells capable of growing without the necessity of anchorage. The cells of the invention have that capability. The anchorage-independent growth capability is improved when the cells include a sequence encoding E2A or a functional derivative or analogue or fragment thereof in its genome, wherein preferably the E2A encoding sequence encodes a temperature sensitive mutant E2A, such as ts125. To have a clean, relatively safe production system from which it is easy to isolate the desired recombinant protein, it is preferred to have a method according to the invention, wherein the human cell includes no other adenoviral sequences. The most preferred cell for the methods and uses of the invention is PER.C6 as deposited under ECACC no. 96022940 or a derivative thereof (see, e.g., U.S. Pat. No. 5,994,128 to Fallaux et al. (Nov. 30, 1999), the contents of which are incorporated by this reference). PER.C6 cells behave better in handling than, for instance, transformed human 293 cells that have also been immortalized by the E1 region from adenovirus (Graham et al., 1977). PER.C6 cells have been characterized and have been documented very extensively because they behave significantly better in the process of up-scaling, suspension growth and growth factor independence. Especially the fact that PER.C6 cells can be brought in suspension in a highly reproducible manner is something that makes it very suitable for large-scale production. Furthermore, the PER.C6 cell line has been characterized for bioreactor growth in which it grows to very high densities.

The cells according to the invention, in particular PER.C6 cells, have the additional advantage that they can be cultured in the absence of animal- or human-derived serum or animal- or human-derived serum components. Thus isolation is easier, while the safety is enhanced due to the absence of additional human or animal proteins in the culture, and the system is very reliable (synthetic media are the best in reproducibility). Furthermore, the presence of the Early region 1A ("E1A") of adenovirus adds another level of advantages as compared to (human) cell lines that lack this particular gene. E1A as a transcriptional activator is known to enhance transcription from the enhancer/promoter of the CMV Immediate Early genes (Olive et al., 1990, Gorman et al., 1989). When the recombinant protein to be produced is under the control of the CMV enhancer/promoter, expression levels increase in the cells and not in cells that lack E1A.

Further provided is a method for enhancing production of a recombinant proteinaceous substance in a eukaryotic cell, including providing the eukaryotic cell with a nucleic acid encoding at least part of the proteinaceous substance, wherein the coding sequence is under control of a CMV-promoter, an E1A promoter or a functional homologue, derivative and/or fragment of either and further providing the cell with E1A activity or E1A-like activity. Like the CMV promoter, E1A promoters are more active in cells expressing one or more E1A products than in cells not expressing such products. It is known that indeed the E1A expression enhancement is a characteristic of several other promoters. For such methods, such promoters are considered to be functional homologues of E1A promoters. The E1A effect can be mediated through the attraction of transcription activators, the E1A promoter or homologue thereof, and/or through the removal/avoiding attachment of transcriptional repressors to the promoter. The binding of activators and repressors to a promoter occurs in a sequence-dependent fashion. A functional derivative and/or fragment of an E1A promoter or homologue thereof, therefore, at least includes the nucleic acid binding sequence of at least one E1A protein regulated activator and/or repressor.

Another advantage of such cells is that they harbor and express constitutively the adenovirus E1B gene. Adenovirus E1B is a well-known inhibitor of programmed cell death, or apoptosis. This inhibition occurs either through the 55K E1B product by its binding to the transcription factor p53 or subsequent inhibition (Yew and Berk 1992). The other product of the E1B region, 19K E1B, can prevent apoptosis by binding and thereby inhibiting the cellular death proteins Bax and Bak, both proteins that are under the control of p53 (White et al., 1992; Debbas and White, 1993; Han et al., 1996; and Farrow et al., 1995). These features can be extremely useful for the expression of recombinant proteins that, when overexpressed, might be involved in the induction of apoptosis through a p53-dependent pathway.

Further provided is the use of a human cell for the production of a human recombinant protein, the cell having a sequence encoding at least an immortalizing E1 protein of an adenovirus or a functional derivative, homologue or fragment thereof in its genome, which cell does not produce structural adenoviral proteins. In certain embodiments, the invention provides such a use wherein the human cell is derived from a primary cell, preferably wherein the human cell is a PER.C6 cell or a derivative thereof.

Further provided is a use according to the invention, wherein the cell further includes a sequence encoding E2A or a functional derivative or analogue or fragment thereof in its genome, preferably wherein the E2A is temperature sensitive.

Also provided is a human recombinant protein obtainable by a method or by a use disclosed herein, the human recombinant protein having a human glycosylation pattern different from the isolated natural human counterpart protein.

In certain embodiments, the invention provides a human cell having a sequence encoding E1 of an adenovirus or a functional derivative, homologue or fragment thereof in its genome, which cell does not produce structural adenoviral proteins, and having a gene encoding a human recombinant protein, preferably a human cell which is derived from PER.C6 as deposited under ECACC no. 96022940.

In yet another embodiment, the invention provides such a human cell, PER.C6/E2A, which further includes a sequence encoding E2A or a functional derivative or analogue or fragment thereof in its genome, preferably wherein the E2A is temperature sensitive.

The proteins to be expressed in these cells using the methods of the invention are well known to persons skilled in the art. They are preferably human proteins that undergo some kind of processing in nature, such as secretion, chaperoned folding and/or transport, co-synthesis with other subunits, glycosylation, or phosphorylation. Typical examples for therapeutic or diagnostic use include monoclonal antibodies that are comprised of several subunits, tissue-specific plasminogen activator ("tPA"), granulocyte colony stimulating factor ("G-CSF") and human erythropoietin ("EPO" or "hEPO"). EPO is a typical product that, especially in vivo, heavily depends on its glycosylation pattern for its activity and immunogenicity. Thus far, relatively high levels of EPO have been reached by the use of CHO cells which are differently glycosylated in comparison to EPO purified from human urine, albeit equally active in the enhancement of erythrocyte production. The different glycosylation of such EPO, however, can lead to immunogenicity problems and altered half-life in a recipient.

The invention also includes a novel human immortalized cell line for this purpose and the uses thereof for production. PER.C6 cells (PCT International Patent Publication WO 97/00326 or U.S. Pat. No. 5,994,128) were generated by transfection of primary human embryonic retina cells using a plasmid that contained the adenovirus serotype 5 (Ad5) E1A- and E1B-coding sequences (Ad5 nucleotides 459-3510) under the control of the human phosphoglycerate kinase ("PGK") promoter.

The following features make PER.C6 particularly useful as a host for recombinant protein production: (1) fully characterized human cell line; (2) developed in compliance with GRP; (3) can be grown as suspension cultures in defined serum-free medium devoid of any human- or animal-derived proteins; (4) growth compatible with roller bottles, shaker flasks, spinner flasks and bioreactors with doubling times of about 35 hours; (5) presence of E1A causing an up-regulation of expression of genes that are under the control of the CMV enhancer/promoter; (6) presence of E1B which prevents p53-dependent apoptosis possibly enhanced through overexpression of the recombinant transgene.

In certain embodiments, the invention provides a method wherein the cell is capable of producing two- to 200-fold more recombinant protein and/or proteinaceous substance than conventional mammalian cell lines. Preferably, the conventional mammalian cell lines are selected from the group consisting of CHO, COS, Vero, Hela, BHK and Sp-2/0 cell lines.

Thus, it would be an improvement in the art to provide a human cell that produces consistent human-type protein processing like post-translational and peri-translational modifications, such as, but not limited to glycosylation. It would be further advantageous to provide a method for producing a recombinant mammalian cell and proteins from recombinant mammalian cells in large-scale production.

Previously, few, if any, human cells suitable for producing proteins in any reproducible and upscaleable manner have been found. The cells of the invention include at least an immortalizing adenoviral E1 protein and are capable of growing relatively independent of exogenous growth factors.

Furthermore, these cells are capable of producing proteins in significant amounts and are capable of correctly processing the generated immunoglobulins.

The fact that cell types that have been used for protein production are tumor-derived adds an extra risk to working with these particular cell lines and results in very stringent isolation procedures for the proteins in order to avoid transforming activity or tumorigenic material in any preparations. It is, therefore, preferred to employ a method according to the invention, wherein the cell is derived from a primary cell. In order to be able to grow indefinitely, a primary cell needs to be immortalized, which in the invention has been achieved by the introduction of an adenoviral E1 protein.

In order to achieve large-scale (continuous) production of proteins through cell culture, it is preferred to have cells capable of growing without the necessity of anchorage. The cells of the invention have that capability. The anchorage-independent growth capability is improved when the cells include an adenovirus-derived sequence encoding E2A (or a functional derivative or analogue or fragment thereof) in its genome. In a preferred embodiment, the E2A encoding sequence encodes a temperature sensitive mutant E2A, such as ts125. The cell may, in addition, include a nucleic acid (e.g., encoding tTa), which allows for regulated expression of a gene of interest when placed under the control of a promoter (e.g., a TetO promoter).

To have a clean and safe production system from which it is easy to isolate the desired proteins, it is preferred to have a method according to the invention, wherein the human cell includes no other adenoviral sequences. The most preferred cell for the methods and uses of the invention is a PER.C6 cell (or a derivative thereof) as deposited under ECACC no. 96022940. PER.C6 cells have been found to be more stable, particularly in handling, than, for instance, transformed human 293 cells immortalized by the adenoviral E1 region. PER.C6 cells have been extensively characterized and documented, demonstrating good process of upscaling, suspension growth and growth factor independence. Furthermore, PER.C6 can be incorporated into a suspension in a highly reproducible manner, making it particularly suitable for large-scale production. In this regard, the PER.C6 cell line has been characterized for bioreactor growth, where it can grow to very high densities.

The cells of the invention, in particular PER.C6, can advantageously be cultured in the absence of animal- or human-derived serum, or animal- or human-derived serum components. Thus, isolation of proteins is simplified and safety is enhanced due to the absence of additional human or animal proteins in the culture. The absence of serum further increases reliability of the system since use of synthetic media, as contemplated herein, enhances reproducibility.

Further provided is the use of a recombinant mammalian cell for the production of at least one polypeptide, the cell having a sequence encoding at least an immortalizing E1 protein of an adenovirus or a functional derivative, homologue or fragment thereof in its genome, which cell does not produce structural adenoviral proteins. In certain embodiments, the invention provides such a use wherein the cell is derived from a primary cell, preferably wherein the human cell is a PER.C6 cell or a derivative thereof.

Further provided is a use according to the invention, wherein the cell further includes a sequence encoding E2A (or a functional derivative or analogue or fragment thereof) in its genome, preferably wherein the E2A is temperature sensitive. In addition, the invention provides a method of using the invention, wherein the cell further includes a trans-activating protein for the induction of the inducible promoter. Also provided is proteins obtainable by a method according to the invention or by a use according to the invention.

In certain embodiments, the invention provides a human cell having a sequence encoding E1 of an adenovirus (or a functional derivative, homologue or fragment thereof) in its genome, which cell does not produce structural adenoviral proteins, and having a gene encoding a human recombinant protein, preferably a human cell which is derived from PER.C6 as deposited under ECACC No. 96022940.

In yet another embodiment, the invention provides such a human cell, PER.C6/E2A, which further includes a sequence encoding E2A (or a functional derivative, analogue or fragment thereof) in its genome, preferably wherein the E2A is temperature sensitive.

Further provided is methods for producing at least one polypeptide in a recombinant mammalian cell utilizing the immortalized recombinant mammalian cell of the invention, culturing the same in a suitable medium, and harvesting at least one polypeptide from the recombinant mammalian cell and/or medium. The recombinant polypeptides, or derivatives thereof, may be used for the therapeutic treatment of mammals or the manufacture of pharmaceutical compositions.

In certain embodiments, a cell is derived from a human primary cell, preferably a cell which is immortalized by a gene product of the E1 gene. In order to be able to grow, a primary cell, of course, needs to be immortalized. A good example of such a cell is one derived from a human embryonic retinoblast.

In cells according to the invention, it is important that the E1 gene sequences are not lost during the cell cycle. It is, therefore, preferred that the sequence encoding at least one gene product of the E1 gene is present in the genome of the (human) cell. For reasons of safety, care is best taken to avoid unnecessary adenoviral sequences in the cells according to the invention. It is thus another embodiment of the invention to provide cells that do not produce adenoviral structural proteins. However, in order to achieve large-scale (continuous) virus protein production through cell culture, it is preferred to have cells capable of growing without needing anchorage. The cells of the invention have that capability. To have a clean and safe production system from which it is easy to recover and, if desirable, to purify the recombinant protein, it is preferred to have a method according to the invention, wherein the human cell includes no other adenoviral sequences. The most preferred cell for the methods and uses of the invention is PER.C6 as deposited under ECACC no. 96022940, or a derivative thereof.

Thus, provided is a method using a cell according to the invention, wherein the cell further includes a sequence encoding E2A or a functional derivative or analogue or fragment thereof, preferably a cell wherein the sequence encoding E2A or a functional derivative or analogue or fragment thereof is present in the genome of the human cell, and most preferably a cell wherein the E2A encoding sequence encodes a temperature sensitive mutant E2A.

Furthermore, as stated, also provided is a method according to the invention wherein the (human) cell is capable of growing in suspension.

Also described is a method wherein the human cell can be cultured in the absence of serum. The cells according to the invention, in particular PER.C6® cells, have the additional advantage that they can be cultured in the absence of serum or serum components. Thus, isolation is easy, safety is enhanced and reliability of the system is good (synthetic media are the best in reproducibility). The human cells of the invention, and in particular those based on primary cells and particularly the ones based on HER cells, are capable of normal post and peri-translational modifications and assembly. This means that they are very suitable for preparing proteins for use in therapeutic applications.

Thus, the invention also includes a method wherein the protein includes a protein that undergoes post-translational and/or peri-translational modification, especially wherein the modifications include glycosylation.

In another aspect, the invention provides the use of an adenoviral E1B protein or a functional derivative, homologue and/or fragment thereof having anti-apoptotic activity for enhancing the production of a proteinaceous substance in a eukaryotic cell, the use including providing the eukaryotic cell with the E1B protein, derivative, homologue and/or fragment thereof. In a preferred embodiment, the use includes a cell of the invention. In certain embodiments, the invention provides such a use in a method and/or a use described herein.

In certain embodiments, the proteinaceous substance or protein is a monoclonal antibody. Antibodies, or immunoglobulins ("Igs"), are serum proteins that play a central role in the humoral immune response, binding antigens and inactivating them or triggering the inflammatory response which results in their elimination. Antibodies are capable of highly specific interactions with a wide variety of ligands, including tumor-associated markers, viral coat proteins, and lymphocyte cell surface glycoproteins. They are, therefore, potentially very useful agents for the diagnosis and treatment of human diseases. Recombinant monoclonal and single chain antibody technology is opening new perspectives for the development of novel therapeutic and diagnostic agents. Mouse monoclonal antibodies have been used as therapeutic agents in a wide variety of clinical trials to treat infectious diseases and cancer. The first report of a patient being treated with a murine monoclonal antibody was published in 1980 (Nadler et al. 1980). However, the effects observed with these agents have, in general, been quite disappointing (for reviews, see Lowder et al. 1985, Mellstedt et al. 1991, Baldwin and Byers 1985). Traditionally, recombinant monoclonal antibodies (immunoglobulins) are produced on B-cell hybridomas. Such hybridomas are produced by fusing an immunoglobulin-producing B-cell, initially selected for its specificity, to a mouse myeloma cell and thereby immortalizing the B-cell. The original strategy of immortalizing mouse B-cells was developed in 1975 (Köhler and Milstein). However, immunoglobulins produced in such hybridomas have the disadvantage that they are of mouse origin, resulting in poor antibody specificity, low antibody affinity and a severe host anti-mouse antibody response (HAMA, Shawler et al. 1985). This HAMA response may lead to inflammation, fever, and even death of the patient.

Mouse antibodies have a low affinity in humans and, for reasons yet unknown, have an extremely short half-life in human circulation (19-42 hours) as compared to human antibodies (21 days, Frödin et al., 1990). That, together with the severity of the HAMA response, has prompted the development of alternative strategies for generating more human or completely humanized immunoglobulins (reviewed by Owens and Young 1994, Sandhu 1992, Vaswani et al. 1998).

One such strategy makes use of the constant regions of the human immunoglobulin to replace its murine counterparts, resulting in a new generation of "chimeric" and "humanized" antibodies. This approach is taken since the HAMA response is mainly due to the constant domains (Oi et al., 1983; Morrison et al., 1984). An example of such a chimeric antibody is CAMPATH-1H (Reichmann et al. 1988). The CAMPATH-1H Ab, used in the treatment of non-Hodgkin's B-cell lymphoma and refractory rheumatoid arthritis, is directed against the human antigen CAMPATH-1 (CDw52) present on all lymphoid cells and monocytes but not on other cell types (Hale et al. 1988, Isaacs et al. 1992). Other examples are Rituxan (Rituximab) directed against human CD20 (Reff et al. 1994) and 15C5, a chimeric antibody raised against human fragment-D dimer (Vandamme et al. 1990, Bulens et al. 1991) used in imaging of blood clotting. However, since these new generation chimeric antibodies are still partly murine, they can induce an immune response in humans, albeit not as severe as the HAMA response against fully murine antibodies of mouse origin.

In another, more sophisticated approach, ranges of residues present in the variable domains of the antibody, but apparently not essential for antigen recognition, are replaced by more human-like stretches of amino acids, resulting in a second generation or hyperchimeric antibodies (Vaswani et al. 1998). A well-known example of this approach is Herceptin (Carter et al. 1992), an antibody that is 95% human, which is directed against HER2 (a tumor-specific antigen) and used in breast tumor patients.

A more preferred manner to replace mouse recombinant immunoglobulins would be one resulting in the generation of human immunoglobulins. Importantly, since it is unethical to immunize humans with experimental biological materials, it is not feasible to subsequently select specific B-cells for immortalization as was shown for mouse B-cells (Köhler and Milstein 1975). Although B-cells from patients were selected for specific antibodies against cancer antigens, it is technically more difficult to prepare human immunoglobulins from human material as compared to mouse antibodies (Köhler and Milstein, 1975). A recombinant approach to produce fully human antibodies became feasible with the use of phage displayed antibody libraries, expressing variable domains of human origin (McCafferty et al. 1990, Clarkson et al. 1991, Barbas et al. 1991, Garrard et al. 1991, Winter et al. 1994, Burton and Barbas, 1994). These variable regions are selected for their specific affinity for certain antigens and are subsequently linked to the constant domains of human immunoglobulins, resulting in human recombinant immunoglobulins. An example of this latter approach is the single chain Fv antibody 17-1A (Riethmuller et al. 1994) that was converted into an intact human IgG1 kappa immunoglobulin named UBS-54, directed against the tumor-associated EpCAM molecule (Huls et al. 1999).

The production systems to generate recombinant immunoglobulins are diverse. The mouse immunoglobulins first used in clinical trials were produced in large quantities in their parental-specific B-cell and fused to a mouse myeloma cell for immortalization. A disadvantage of this system is that the immunoglobulins produced are entirely of mouse origin and render a dramatic immune response (HAMA response) in the human patient (as previously described herein).

Partially humanized or human antibodies lack a parental B-cell that can be immortalized and therefore have to be produced in other systems like CHO cells or Baby Hamster Kidney (BHK) cells. It is also possible to use cells that are normally suited for immunoglobulin production like tumor-derived human or mouse myeloma cells. However, antibody yields obtained in myeloma cells are, in general, relatively low (±0.1 ug/ml) when compared to those obtained in the originally identified and immortalized B-cells that produce fully murine immunoglobulins (±10 ug/ml, Sandhu 1992).

To circumvent these and other shortcomings, different systems are being developed to produce humanized or human immunoglobulins with higher yields.

For example, it was recently shown that transgenic mouse strains can be produced that have the mouse IgG genes replaced with their human counterparts (Bruggeman et al., 1991, Lonberg et al., 1994, Lonberg and Huszar, 1995, Jacobovits, 1995). Yeast artificial chromosomes ("YACs") containing large fragments of the human heavy and light (kappa) chain immunoglobulin (Ig) loci were introduced into Ig-inactivated mice, resulting in human antibody production which closely resembled that seen in humans, including gene rearrangement, assembly, and repertoire (Mendez et al. 1997, Green et al. 1994). Likewise, Fishwild et al. (1996) have constructed human Ig-transgenics in order to obtain human immunoglobulins using subsequent conventional hybridoma technology. The hybridoma cells secreted human immunoglobulins with properties similar to those of wild-type mice including stability, growth, and secretion levels. Recombinant antibodies produced from such transgenic mice strains carry no non-human amino acid sequences.

Nevertheless, human immunoglobulins produced thus far have the disadvantage of being produced in non-human cells, resulting in non-human post-translational modifications like glycosylation and/or folding of the subunits. All antibodies are glycosylated at conserved positions in their constant regions, and the presence of carbohydrates can be critical for antigen clearance functions such as complement activation. The structure of the attached carbohydrate can also affect antibody activity. Antibody glycosylation can be influenced by the cell in which it is produced, the conformation of the antibody and cell culture conditions. For instance, antibodies produced in mouse cells carry glycans containing the Gal alpha1-3Gal residue, which is absent in proteins produced in human cells (Borrebaeck et al. 1993, Borrebaeck, 1999). A very high titer of anti-Gal alpha1-3Gal antibodies is present in humans (100 ug/ml, Galili, 1993), causing a rapid clearance of (murine) proteins carrying this residue in their glycans.

It soon became apparent that, in order to exert an effect, patients need to be treated with very high doses of recombinant immunoglobulins for prolonged periods of time. It seems likely that post-translational modifications on human or humanized immunoglobulins that are not produced on human cells strongly affect the clearance rate of these antibodies from the bloodstream.

It is unclear why immunoglobulins produced on CHO cells also need to be applied in very high dosages, since the Gal alpha1-3Gal residue is not present in glycans on proteins derived from this cell line (Rother and Squinto, 1996). Therefore, other post-translational modifications besides the Gal alpha1-3Gal residues are likely to be involved in specific immune responses in humans against fully human or humanized immunoglobulins produced on such CHO cells.

The art thus teaches that it is possible to produce humanized antibodies without murine-derived protein sequences. However, the current generation of recombinant immunoglobulins still differs from its natural human counterparts, for example, by post-translational modifications such as glycosylation and folding. This may result in activation of the immune system of the patient and cause undesirable responses that may affect the efficacy of the treatment. Thus, despite the development of chimeric antibodies, the current production systems still need optimization to produce fully human or humanized active antibodies.

It is thus clearly desirable to have methods for producing fully human antibodies which behave accordingly, and which are, in addition, produced at higher yields than observed in human myeloma cells.

Thus, it would be an improvement in the art to provide a human cell that produces consistent human-type protein processing like post-translational and peri-translational modifications, such as, but not limited to glycosylation. It would be further advantageous to provide a method for producing a recombinant mammalian cell and immunoglobulins from recombinant mammalian cells in large-scale production.

Therefore, further provided is a method for producing at least one variable domain of an immunoglobulin in a recombinant mammalian cell, including providing a mammalian cell including a nucleic acid encoding at least an immortalizing E1 protein of an adenovirus or a functional derivative, homologue and/or fragment thereof in its genome, and further including a second nucleic acid encoding the immunoglobulin, culturing the cell in a suitable medium and harvesting at least one monoclonal antibody from the cell and/or the medium.

Previously, few, if any, human cells suitable for producing immunoglobulins in any reproducible and upscaleable manner have been found. The cells of the invention include at least an immortalizing adenoviral E1 protein and are capable of growing relatively independent of exogenous growth factors.

Furthermore, these cells are capable of producing immunoglobulins in significant amounts and are capable of correctly processing the generated immunoglobulins.

The fact that cell types that have been used for immunoglobulin production are tumor-derived adds an extra risk to working with these particular cell lines and results in very stringent isolation procedures for the immunoglobulins in order to avoid transforming activity or tumorigenic material in any preparations. It is therefore preferred to employ a method according to the invention, wherein the cell is derived from a primary cell. In order to be able to grow indefinitely, a primary cell needs to be immortalized, which in the invention has been achieved by the introduction of an adenoviral E1 protein.

In order to achieve large-scale (continuous) production of immunoglobulins through cell culture, it is preferred to have cells capable of growing without the necessity of anchorage. The cells of the invention have that capability. The anchorage-independent growth capability is improved when the cells include an adenovirus-derived sequence encoding E2A (or a functional derivative or analogue or fragment thereof) in its genome. In a preferred embodiment, the E2A encoding sequence encodes a temperature sensitive mutant E2A, such as ts125. The cell may, in addition, include a nucleic acid (e.g., encoding tTa), which allows for regulated expression of a gene of interest when placed under the control of a promoter (e.g., a TetO promoter).

The nucleic acid may encode a heavy chain, a variable heavy chain, a light chain, and/or a variable light chain of an immunoglobulin. Alternatively, a separate or distinct nucleic acid may encode one or more variable domain(s) of an Ig (or a functional derivative, homologue and/or fragment thereof) as a counterpart to the first nucleic acid (described above). One or more nucleic acid(s) described herein may encode an ScFv and may be human or humanized. The nucleic acid(s) of the invention can in certain embodiments be placed under the control of an inducible promoter (or a functional derivative thereof).

To have a clean and safe production system from which it is easy to isolate the desired immunoglobulins, it is preferred to have a method according to the invention, wherein the human cell includes no other adenoviral sequences in its genome. The most preferred cell for the methods and uses of the invention is PER.C6 or a derivative thereof as deposited under ECACC no. 96022940. PER.C6 has been found to be more stable, particularly in handling, than, for instance, transformed human 293 cells immortalized by the adenoviral E1 region. PER.C6 cells have been extensively characterized and documented, demonstrating good process of upscaling, suspension growth and growth factor independence. Furthermore, PER.C6 can be incorporated into a suspension in a highly reproducible manner, making it particularly suitable for large-scale production. In this regard, the PER.C6 cell line has been characterized for bioreactor growth, where it can grow to very high densities.

The cells of the invention, in particular PER.C6, can advantageously be cultured in the absence of animal- or human-derived serum, or animal- or human-derived serum components. Thus, isolation of monoclonal antibodies is simplified and safety is enhanced due to the absence of additional human or animal proteins in the culture. The absence of serum further increases reliability of the system since use of synthetic media, as contemplated herein, enhances reproducibility.

Further provided is the use of a recombinant mammalian cell for the production of at least one variable domain of an immunoglobulin, the cell having a sequence encoding at least an immortalizing E1 protein of an adenovirus or a functional derivative, homologue or fragment thereof in its genome, which cell does not produce structural adenoviral proteins. In certain embodiments, the invention provides such a use wherein the cell is derived from a primary cell, preferably wherein the human cell is a PER.C6 cell or a derivative thereof.

Further provided is a use, wherein the cell further includes a sequence encoding E2A (or a functional derivative or analogue or fragment thereof) in its genome, preferably wherein the E2A is temperature sensitive. In addition, the invention provides a method of using the invention, wherein the cell further includes a trans-activating protein for the induction of the inducible promoter. Also provided is immunoglobulins obtainable by a method according to the invention or by a use according to the invention.

Immunoglobulins to be expressed in the cells of the invention are known to persons skilled in the art. Examples of recombinant immunoglobulins include, but are not limited to, Herceptin®, Rituxan (Rituximab®), UBS-54, CAMPATH-1H®, and 15C5.

Further provided are methods for producing at least one variable domain of an immunoglobulin in a recombinant mammalian cell utilizing the immortalized recombinant mammalian cell of the invention, culturing the same in a suitable medium, and harvesting at least one variable domain of a selected Ig from the recombinant mammalian cell and/or medium. Immunoglobulins, variable domains of the immunoglobulins, or derivatives thereof may be used for the therapeutic treatment of mammals or the manufacture of pharmaceutical compositions.

In certain embodiments, further provided is a method for producing a viral protein other than adenovirus or adenoviral protein for use as a vaccine including providing a cell with at least a sequence encoding at least one gene product of the E1 gene or a functional derivative thereof of an adenovirus, providing the cell with a nucleic acid encoding the viral protein, culturing the cell in a suitable medium allowing for expression of the viral protein and harvesting viral protein from the medium and/or the cell. Until the invention, there are few, if any (human), cells that have been found suitable to produce viral proteins for use as vaccines in any reproducible and upscaleable manner and/or sufficiently high yields and/or easily purifiable. We have now found that cells which include adenoviral E1 sequences, preferably in their genome, are capable of producing the viral protein in significant amounts.

Thus, the invention also includes a method wherein the viral protein includes a protein that undergoes post-translational and/or peri-translational modification, especially wherein the modifications include glycosylation. A good example of a viral vaccine that has been cumbersome to produce in any reliable manner is influenza vaccine. The invention provides a method according to the invention wherein the viral proteins include at least one of an influenza virus neuramidase and/or a hemagglutinin. Other viral proteins (subunits) that can be produced in the methods according to the invention include proteins from enterovirus, such as rhinovirus, aphto virus, or poliomyelitis virus, herpes virus, such as herpes simplex virus, pseudorabies virus or bovine herpes virus, orthomyxovirus, such as influenza virus, a paramyxovirus, such as Newcastle Disease virus, respiratory syncitio virus, mumps virus or a measles virus, retrovirus, such as human immunodeficiency virus or a parvovirus or a papova virus, rotavirus or a coronavirus, such as transmissible gastroenteritis virus or a flavivirus, such as tick-borne encephalitis virus or yellow fever virus, a togavirus, such as rubella virus or eastern-, western-, or Venezuelan equine encephalomyelitis virus, a hepatitis causing virus, such as hepatitis A or hepatitis B virus, a pestivirus, such as hog cholera virus or a rhabdovirus, such as rabies virus.

Also provided is the products resulting from the methods and uses according to the invention, especially viral proteins obtainable according to those uses and/or methods, especially when brought in a pharmaceutical composition including suitable excipients and in some formats (subunits) adjuvants. Dosage and ways of administration can be sorted out through normal clinical testing if they are not yet available through the already registered vaccines.

Thus, also provided is a viral protein for use in a vaccine obtainable by a method or by a use according to the invention, the viral protein being free of any non-human mammalian proteinaceous material and a pharmaceutical formulation including such a viral protein.

In a preferred embodiment, the invention provides influenza vaccines obtainable by a method according to the invention or by a use according to the invention.

As shown in U.S. Pat. No. 6,855,544 (the '544 patent) to Hateboer et al, the contents of the entirety of which are incorporated by this reference, immortalized human embryonic retina cells expressing at least an adenovirus E1A protein, such as PER.C6 cells, can be suitably used for the production of recombinant proteins. In preferred aspects in the '544 patent, the transgene encoding the protein of interest is integrated into the cells genome. The advantage of such methods is that long-term stable expression can be obtained, because the transgene is stably inherited. This is particularly advantageous when recombinant proteins are to be used in pharmaceutical applications, where stability and robustness is of paramount importance, for instance to satisfy the strict regulatory requirements imposed by governing authorities. Moreover, large quantities of recombinant protein can be obtained once a suitable cell line has been selected.

However, a disadvantage of methods wherein stable clones are used, is that it takes relatively long (at least several months) and relatively much hands-on time of laboratory personnel to obtain the stable clone with the desired characteristics. Therefore, transient expression methods are seen in some circumstances as an alternative to stable expression methods (e.g., Wurm and Bernard, 1999; Baldi et al, 2007), in particular to obtain limited amounts of material that can be used for pre-clinical testing and in some cases even for phase I clinical trials. Efforts have been made to scale-up transient transfection methods in suspension for certain cell lines to 100 liter scale, so that sufficient material for clinical trials can in principle be obtained. In transient expression methods, a plasmid containing the transgene is transfected into the host cells, generally without applying selection, and the transiently expressed protein is harvested from the pool of transfected cells (i.e., without generating stable clones). As shown in the incorporated '544 patent, PER.C6 cells can also be suitably used for transient expression of proteins. The advantage of transient expression methods is the limited time required to obtain some material of the protein of interest (depending somewhat on the scale, but most effort is required to obtain sufficient cells and plasmid to be transfected, while within a few days after transfection the desired protein can be harvested, so that the total time required for obtaining material in general is not more than a few weeks). A disadvantage of transient transfection with plasmids in suspension is its inherent inefficiency, because i) DNA is not easily taken up by cells, and ii) required transport of the DNA from the cytoplasm where it is taken up into the nucleus where it is transcribed is inefficient. Therefore, only a relatively small subset of the cells of the transfected pool will contribute to expression of the protein of interest (in transient transfection with adherent cells efficient transfection is possible, but those methods are not scalable to industrially useful amounts). Hence, expression levels in such transient suspension systems are usually orders of magnitude lower than those obtainable by recombinant expression from stable cell clones. Furthermore, because of these inherent disadvantages that become increasingly more apparent at larger scale, the scalability of these systems has its limits, and it is questionable whether transient plasmid transfections for protein production could become economically profitable beyond the 100 liter scale. The best results reported thus far for a multiliter transfection in CHO cells by highly specialized investigators in this field, described a recombinant antibody yield of 22 mg/l (Muller et al, 2007).

Disclose herein is a relatively clean and scalable transient expression system for efficient high level expression of proteins of interest, by infection of suitable cells with recombinant adenovirus vectors. This system allows for clean 'super-transfection' of the cells, and has the advantages of transient systems (fast), and does not, or to a much less extent, have the disadvantages described above. For instance, because adenovirus vectors infect cells very efficiently and moreover deliver their transgenes into the nucleus of the infected cell, the inherent disadvantage described for the transient transfection with plasmids have been overcome, and using the system of the invention provides a very high percentage of cultured cells that contribute to expression of the protein. In addition, the system is very fast and thus has advantages over the stable transfection methods described above. Moreover, the system is scalable, in principle to very large bioreactor scale (e.g., 10 1, 100 1, 500 1, 1000 1, 2000 1, 5000 1, 10000 1, 20000 1) since the host cells can be cultured to very large scale according to known methods, and adenovirus biology will serve for very efficient infection levels and thus expression of the transgene in a very high proportion of the cells in the large culture. The system can thus be used at industrial scale to prepare proteins of interest, for instance for characterization of the protein, pre-clinical testing, phase I testing, and in certain cases even for phase II testing. The system can also be downscaled to prepare small quantities of many different proteins for testing some properties of a variety of candidate proteins, e.g., in a multi-well format. Our first results as reported herein for expression of an antibody demonstrate a yield of 140 mg/l.

Recombinant adenoviruses are widely used in the field of gene therapy and in the field of vaccine preparation. In general in these fields, the recombinant adenovirus has a deletion in at least one region required for replication of the adenovirus, e.g., the early region 1 (E1), providing space for a transgene of interest that can be expressed in the target cells. Because of the deletion of one essential region, the resulting virus is replication deficient in normal cells, and to propagate the virus a so-called complementing cell is used, that provides in trans the functions deleted from the adenovirus genome. Most, if not all, adenovirus vectors used today have a deletion in E1, and complementing cells providing the E1 function are used for complementation. Several such E1-complementing cells are known in the art, such as HEK293, 911, PER.C6, and many others. A particularly useful complementing cell is a PER.C6 cell (U.S. Pat. No. 5,994,128, incorporated herein by reference). Construction of recombinant adenovirus and complementing cell lines that complement the corresponding deficiencies in the genome of the recombinant adenovirus have been extensively described and is part of the knowledge of the skilled person, which can make such materials in a routine fashion based on this knowledge, see e.g., U.S. Pat. Nos. 6,133,028; 5,994,128; and 6,482,616, all incorporated in their entirety by reference herein.

Figure 1:
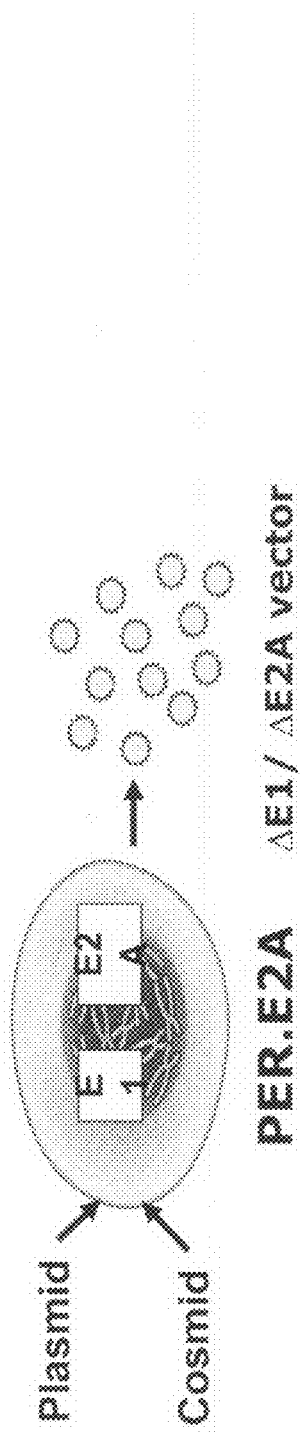
FIG. 1. Schematic drawing of the invention. In a first step (A), a recombinant adenoviral vector with deletions in E1 and E2A is propagated in a first type of complementing cells that express both E1 and E2A of adenovirus (here PER.E2A cells) (the recombinant adenoviral vector in this Fig. is generated in situ by recombination of a plasmid containing the left end of the adenovirus genome and a transgene encoding the protein of interest with a cosmid containing the remainder of the adenovirus genome, inside the complementing cell, but other methods are equally suitable). In this step, recombinant adenovirus particles are formed ($\Delta$E1/$\Delta$E2A vector). In a second step (B), the recombinant adenovirus particles are used to infect a second type of complementing cells that express E1, but not E2A (here PER.C6 cells), so that the adenovirus particles can infect and produce protein in these cells, but cannot replicate and form adenovirus progeny in these cells. This results in very efficient (high yield, fast) transient production of the protein of interest.
Figure 1:
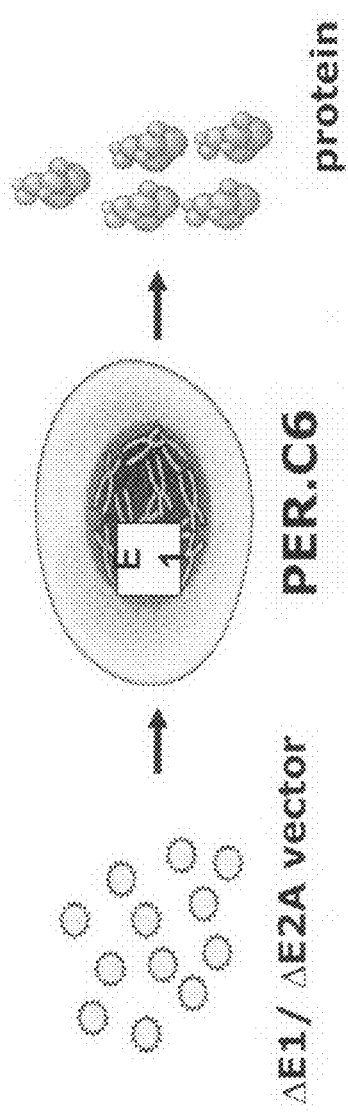

The transient protein expression system disclosed herein makes use of recombinant adenovirus that has at least two deletions in the genome of wild-type adenovirus. The deletions are in regions of the adenovirus genome that are required for adenovirus genome replication and/or for adenovirus particle formation. The recombinant adenovirus genome further comprises a transgene, comprising nucleic acid encoding the protein of interest in expressible format. In preferred embodiments, the adenovirus genome is deleted in the E1 region, which is thus one of the at least two deletions. The other deletion is in a region of the adenovirus genome that is required for adenovirus genome replication or adenovirus particle formation, and in certain embodiments is in the E2A region. In a first step, for propagation of the adenovirus, a complementation cell line is used that complements both deletions. For instance, for an adenovirus with deletions in E1 and E2A, a complementation cell that expresses both E1 and E2A is used in this step. In this manner, recombinant adenovirus particles are obtained, which contain a genome comprising the transgene and having deletions in the two regions. These obtained adenovirus particles are used to infect a second type of complementing cells, which complement only one of the two deletions. In preferred embodiments, the second type of complementing cells expresses adenoviral E1 protein. The recombinant adenovirus particles can efficiently infect these cells, but cannot be propagated therein or at least not form infectious particles therein because the functions required for adenovirus replication or particle formation are absent (i.e., both from the genome of the recombinant adenovirus and from the complementing cell). Therefore, these cells are infected with the recombinant adenovirus, but do not produce adenovirus particles unlike the first complementing cell line. The infection however results in very efficient transient production of the transgene of the adenovirus. The protein of interest is then harvested, without adenovirus particles being produced. FIG. 1 shows a scheme of the method of the invention.

Others have used adenovirus vectors for production of recombinant proteins in complementing cell lines (Massie et al, 1995; Garnier et al, 1994). However, those methods used adenovirus vectors with a deletion in E1 and infected E1-expressing complementing cells, so that adenovirus particles could be formed. The instant invention has the advantage that no adenovirus particles are formed in the final step during expression of the transgene, and thus provides a cleaner system. This is very important when proteins for pharmaceutical use are produced, since the presence of adenovirus particles in the protein preparation will not be allowed in view of regulatory considerations, so that the methods described by others will require additional efforts to remove adenovirus particles. Moreover, the cells do not have to spend energy in forming adenovirus particles, so that the cells are more committed to producing the protein of interest, which may result in higher yields.

Multiply deficient adenovirus vectors, and cells for complementing these, have previously been described by us and by others (e.g., U.S. Pat. Nos. 6,482,616, 6,395,519 and 6,133,028, incorporated herein by this reference). However, in those cases, the cells were just used to complement the vectors, which were subsequently used for gene therapy or vaccine purposes, i.e., the generated recombinant adenoviral particles were used to infect normal cells in a living organism. In contrast, the invention comprises a step of infecting other cultured complementing cells for protein production. In the methods previously disclosed, the purpose was never to produce recombinant protein in vitro in high quantities like in the current invention, but rather to infect cells in vivo to obtain some expression therein in situ. The methods previously described are therefore further silent on harvesting the protein of interest (which was not the goal, nor possible), which is a step of the currently invented methods. Moreover, in the methods previously described, all deficiencies of the adenovirus vectors were complemented in the complementing cells, whereas methods of the invention include a step of infecting cells that do not complement all deficiencies in the adenovirus genome, and isolating protein after this step.

The invention thus provides a method for producing a protein of interest, the method comprising: a) providing a recombinant adenoviral vector comprising nucleic acid encoding the protein of interest under control of a promoter, wherein the adenoviral vector has deletions in a first region and in a second region of the adenovirus genome, wherein each of the first region and the second region is required for adenoviral genome replication and/or adenovirus particle formation, b) propagating the adenoviral vector in a first type of complementing cells that express proteins from the first and from the second region of the adenovirus genome so as to complement the deletions of the recombinant adenoviral vector, to obtain recombinant adenovirus particles, c) infecting a culture of a second type of complementing cells with the recombinant adenovirus particles, wherein the second type of complementing cells express protein from the first region of the adenovirus genome but not protein from the second region of the adenovirus genome, to produce the protein of interest, and d) harvesting the protein of interest.

In preferred embodiments, the first region of the adenovirus genome is the E1 region. Nearly all adenovirus vectors that are currently used have a deletion in E1, and therefore several complementing cells that express E1 protein are available. Any cell expressing E1 protein and susceptible to adenovirus infection can be used. As non-limiting examples, such cells can be derived from for instance human cells, for instance from a kidney (example: HEK 293 cells, see Graham et al, 1977), lung (e.g., A549, see e.g., WO 98/39411) or retina (example: HER cells such as PER.C6 cells, see U.S. Pat. No. 5,994,128), or from amniocytes (e.g., N52.E6, described in U.S. Pat. No. 6,558,948), and similarly from several other types of cells (see, e.g., Xu et al, Cytotechnology 51: 133-140 (2006); DE 19754103, Kim J-S. et al. (2001) Experimental and Molecular Medicine 33: 145-149). Methods for obtaining such cells are described for instance in U.S. Pat. Nos. 5,994,128 and 6,558,948. Thus, the second type of complementing cells, as used in step c) of the invention, is readily available. Another advantage of embodiments wherein the first region of the adenovirus genome is the E1 region, is that the expression of E1 protein (from the complementing cell) may increase expression of the protein of interest (from the adenovirus transgene), especially when the protein of interest is under control of certain promoters that can be transactivated by E1A, e.g., the CMV promoter. In certain embodiments, the second type of complementing cells as used in step c) of the invention are HEK293 cells. In a particularly preferred embodiment, the complementing cells in step c) are PER.C6 cells. PER.C6 cells for the purpose of the invention means cells from an upstream or downstream passage or a descendent of an upstream or downstream passage of cells as deposited under ECACC no. 96022940, i.e., having the characteristics of those cells. PER.C6 cells have several advantages over other E1-complementing cells, for instance with regard to scalability, safety, ease of handling, and the wide expertise that has been built up with this cell line over the course of many programs for production of pharmaceutical materials using these cells by various companies. PER.C6 cells have for instance been cultured at 20,000 liter scale, demonstrating its applicability for large scale production. Extensive characterization of the cell line, and administration to numerous subjects of several different pharmaceutical products produced in this cell line without any cell line related adverse event, has demonstrated its safety for pharmaceutical purposes. We further demonstrate herein that the yields of recombinant protein produced using the method of the invention are surprisingly high.

The second region of the adenovirus genome may be chosen from any region that is required for adenovirus genome replication or adenovirus particle formation, and can be E1 (only in embodiments where the first region is not the E1 region), but more typically is chosen from other parts of the early region of the adenovirus genome, e.g., E2A, E2B (Ad DNA polymerase) or E4. These regions are required for adenovirus genome replication. Recombinant adenovirus vectors with deletions in E1 and E2A, E2B or E4, as well as cells that complement such vectors have been described before, and are thus available (see, e.g., U.S. Pat. Nos. 6,063,622, 6,482,616 and 6,133,028, incorporated by reference).

In further embodiments, the second region of the adenovirus genome is a region that is not required for replication, but is required for particle formation, e.g., a late gene such as 100K and/or 33K (both encoded by the L4 region, required for correct splicing of the major late transcription unit (MLTU) and therefore for late gene expression; Farley et al, 2004). One potential advantage of such embodiments is that the adenovirus particles used for infection in step c) can replicate inside the complementing cell, so that the amount of template DNA from which protein is expressed is amplified and thus expression of the protein of interest may be further increased, while at the same time no new viral particles can be formed. Adenovirus vectors with deletions of E1 and the 100K gene and complementation cells for such vectors have been described and are thus available (Hodges et al, 2001; U.S. Pat. No. 6,328,958, incorporated by reference). The same is true for pTP and IVa2 proteins (U.S. Pat. No. 6,328,958), and these can thus also be used as the second region of the adenovirus genome in further embodiments of the invention. Further possibilities for the second region of the adenovirus genome according to the invention include hexon, 51K/55K, and combinations of any of the above. The DNA sequence of the Ad5 genome and the encoded proteins therein are completely known (Genbank M73260), and the skilled person can thus generate the desired adenovirus vectors, and the desired complementing cell lines, using routine molecular biology methods.

In certain embodiments, the second region of the adenovirus genome is the E2A region. Adenovirus with deletions in both E1 and E2A has been described, and cell lines expressing E2A have also been described previously, e.g., in U.S. Pat. No. 6,395,519, incorporated in its entirety herein by reference. Such cell lines may be based on PER.C6 cells (that express the E1 region), wherein the E2A region has been introduced and integrated into the genome. Such cell lines may also be based on other E1-complementing cell lines such as HEK293, wherein the E2A region has been introduced. In certain embodiments, a temperature sensitive E2A protein is expressed in the first type of complementing cells used in step b) of the invention, for instance the ts125 E2A mutant (see U.S. Pat. No. 6,395,519). In other embodiments, wild type E2A is expressed and regulated by an inducible promoter (see, e.g., U.S. Pat. No. 6,482,616, incorporated by reference herein). Thus, the first type of complementing cell lines that can be used in step b) of the invention have also been described and are available to the skilled person. In certain preferred embodiments, the first type of complementing cells used in step b) of the invention are PER.C6 cells that express the ts125 E2A protein, which cells are referred to herein as PER.E2A or PER.C6.E2A (see U.S. Pat. No. 6,395,519 for generation of this cell line). E1-deleted adenovirus can be propagated in these cells, and also E1/E2A-deleted adenovirus (adenovirus with deletions in both E1 and E2A) can be propagated in these cells, while PER.C6 cells (without E2A) can only be used to propagate E1-deleted adenovirus. E1/E2A-deleted adenovirus is most efficiently propagated in PER.E2A cells at 34° C., although temperatures of 32° C.-37° C. can be used. In step b) of the invention, recombinant adenovirus particles are formed upon replication and particle formation in the first type of complementing cell. These particles are subsequently used for infection of the second type of complementing cell, which will not complement all deficiencies in the adenoviral genome, but will allow for expression of the recombinant protein of interest that is encoded by the transgene in the adenovirus genome.

The recombinant adenovirus may in certain embodiments further have a deletion in E3, but since this region is not required for adenovirus genome replication or adenovirus particle formation, it needs not be complemented. Deletion of the E3 region or part thereof can be advantageous if the transgene is too large to be accommodated by the adenovirus having only deletions in the first and second regions of the adenovirus genome, as is known to the skilled person. Deletion of the E3 region or part thereof from a recombinant adenovirus genome can be done by routine molecular biology methods known to the person skilled in the art. For the methods of the invention, adenovirus containing the E3 region, as well as adenovirus wherein E3 has been deleted, have been used and gave similar results.

The invention in one preferred embodiment thus provides a method for producing a protein of interest, the method comprising: a) providing a recombinant adenoviral vector comprising nucleic acid encoding the protein of interest under control of a promoter, wherein the adenoviral vector has deletions in the E1 and the E2A regions of the adenovirus genome, b) propagating the adenoviral vector in complementing cells that express adenoviral E1 protein and adenoviral E2A protein, to obtain recombinant adenovirus particles, c) infecting a culture of complementing cells that express adenoviral E1 protein but not adenoviral E2A protein with the recombinant adenovirus particles, to produce the protein of interest, and d) harvesting the protein of interest.

The serotype of the adenovirus for the invention is not material, and the invention can thus be practiced with adenovirus of any serotype, including adenovirus type 2, 5, 7, 11, 26, 35, 49, 50, 51, or a chimeric adenovirus with a genome comprising parts derived from different serotypes, and the like. It can further be an adenovirus from different species, e.g., bovine, ovine, canine, etc, but in preferred embodiments is a human type adenovirus. Complementing cells for several adenovirus serotypes and adenovirus species have been previously described and are thus available for use according to the invention. In certain embodiments, the adenovirus is a human adenovirus type 5 (Ad5).

Recombinant adenovirus genome can be routinely prepared using standard technology, known to the skilled person (e.g., Hosfield and Eldridge, Strategies 13: 100-102, Stratagene). One exemplary method uses two plasmids that are introduced into the first type of complementing cell to form the adenoviral genome via homologous recombination (see e.g., U.S. Pat. No. 6,878,549, incorporated by reference herein). Another method uses two plasmids that are first formed into an adenoviral genome in bacteria or yeast, from which the adenovirus genome is isolated and subsequently used for introduction into the first type of packaging cell (see e.g., He et al, 1998, U.S. Pat. No. 5,922,576, incorporated by reference herein). Such a system is commercially available (described by Hosfield and Eldridge in Strategies 13: 100-102, Stratagene). A first plasmid in these methods suitably contains the left end of the adenovirus genome, wherein E1 has been deleted and is or has been replaced by a transgene that encodes the protein of interest (e.g., in the form of an expression cassette: a promoter operably linked to nucleic acid encoding the protein of interest, and usually a transcription terminator/polyadenylation signal). The second plasmid is usually much larger and suitably is a cosmid (see e.g., U.S. Pat. No. 6,878,549). It contains the remainder of the adenovirus genome and has the desired deletions, e.g., an E2A deletion, and optionally an E3 deletion. Upon recombination these plasmids form the recombinant adenoviral vector comprising the nucleic acid encoding the protein of interest under control of a promoter, of step a) of the invention. Introduction of this vector in the first complementing cells leads to propagation and adenovirus particle generation (step b) of the invention). Cloning of nucleic acid encoding the protein of interest into the adenovirus genome can be done by routine methods, for instance in plasmids containing the left end of the adenovirus genome with a deletion in E1, often referred to as adapter plasmids (e.g., U.S. Pat. No. 6,878,549).

In steps b) and c) of the invention, the complementing cells are cultured in suitable culture medium, using routine methods known to the skilled person. The protein of interest as produced in step c) is preferably secreted into the culture medium. Step d) comprises the harvesting of the protein of interest, and can be performed according to methods known to the skilled person. Harvesting comprises separating the complementing cells from the culture medium, e.g., by centrifugation, filtration, or other methods. The culture medium (supernatant) contains the protein of interest, and can be used directly for certain applications (e.g., testing production levels, product quality analysis), but more typically the protein of interest is further purified from the cell culture supernatant. This can be done using methods known to the skilled person, and dependent from the protein of interest. Methods to purify proteins of interest from a biological matrix such as a cell culture supernatant are available, and usually comprise one or more of centrifugation, filtration, chromatography, and the like. Various useful chromatographic methods are available to purify proteins, including but not limited to anion exchange chromatography, cation exchange chromatography, hydrophobic interaction chromatography, affinity chromatography (e.g., antibody purification on protA columns), size exclusion chromatography, hydroxyapatite chromatography, etc. The skilled person will use methods that are most appropriate for purification of the protein of interest to the desired purity. One or more known virus inactivation steps may be included in the purification procedure if the protein is to be administered to humans.

The protein of interest can be any protein. In certain embodiments, the protein of interest is selected from the group consisting of an antibody, erythropoietin, a blood clotting factor such as Factor VIII, Factor IX, Factor X, Factor XIII, Factor V, Factor VII, or variants thereof, a hormone, a viral protein other than an adenovirus protein, such as an influenza protein, such as hemaglutinin (HA) or neuraminidase (NA), etc. In certain embodiments, the protein of interest is a human protein. In certain embodiments, the protein is a secreted protein. Non-limiting examples of a protein of interest according to the invention are enzymes, hormones, immunoglobulin chains, therapeutic proteins like anti-cancer proteins, blood coagulation proteins, multi-functional proteins, diagnostic proteins, or proteins or fragments thereof useful for vaccination purposes, all known to the person skilled in the art. In certain embodiments, the protein of interest comprises post-translational modifications such as glycosylation, i.e., it is a glycoprotein. In certain embodiments, it comprises at least a variable part of an immunoglobulin heavy or light chain. In certain embodiments, the protein of interest is an antibody. In case where the protein of interest comprises more than one subunit, nucleic acid encoding each subunit can be suitably cloned in an adenovirus vector in the form of a multicistronic transcription unit, e.g., by using an internal ribosome entry site (IRES), according to methods and using means well known to the person skilled in the art. As used herein, an "internal ribosome entry site" or "IRES" refers to an element that promotes direct internal ribosome entry to the initiation codon of a cistron (a protein encoding region), thereby leading to the cap-independent translation of the gene. IRES sequences and use thereof for expression are well known to the person skilled in the art. See e.g., Jackson R J, Howell M T, Kaminski A (1990) Trends Biochem Sci 15 (12): 477-83), Jackson R J and Kaminski, A. (1995) RNA 1 (10): 985-1000, Martinez-Salas, 1999, and Rees et al, 1996. In other embodiments, instead of using an IRES, two or more proteins or subunits are expressed from separate promoters, and both expression units (promoter+sequence encoding protein/subunit of interest) is incorporated into a single adenoviral vector. In such embodiments, it may be beneficial to use different promoters for each of the proteins/subunits, in order to increase the stability of the resulting adenovirus. In certain embodiments, one promoter is a CMV promoter. Alternatively, to express more than one protein or more than one subunit of a multimeric protein such as an antibody, cells in step c) may be co-infected with two or more recombinant adenovirus vectors, each coding for a different protein or subunit. Experiments with heavy and light chain of an antibody each encoded on a different adenovirus vector and co-infection of these vectors into the second type of complementing cells according to step c) of the invention showed that this also resulted in expression of antibodies, and thus this method can be used as an alternative to expressing both subunits from a single adenovirus vector using an IRES between heavy and light chain.

Nucleic acid encoding a protein of interest is typically available, for instance in the form of cDNA, genomic DNA or synthetic DNA, and can be cloned in the recombinant adenoviral vector. The nucleic acid encoding the protein of interest preferably is cloned in operable association with a promoter that can drive transcription of the nucleic acid, all according to standard and routine methods known to the skilled person (see, e.g., Sambrook, Fritsch and Maniatis, *Molecular Cloning: A Laboratory Manual,* 2nd edition, 1989).

Co-expression of an enzyme involved in glycosylation, e.g., a sialyltransferase, e.g., an alfa-2,6-sialyltransferase or an alfa-2,3-sialyltransferase, with the protein of interest can be achieved using methods of the invention. Methods and means for over-expression of enzymes involved in post-translational modification, in particular alfa-2,6-sialyltransferase or alfa-2,3-sialyltransferase, in PER.C6 cells have been previously described, and were shown to increase sialylation of recombinant proteins produced in PER.C6 cells. See, e.g., US 2005/0164386 and US 2005/0181359, both incorporated herein by reference. A suitable α-2,6-sialyltransferase is a human α-2,6-sialyltransferase, the sequence of which was described by Grundmann et al, 1990. In certain embodiments, the second type of complementing cells express recombinant nucleic acid encoding an alfa-2,3-sialyltransferase, for instance under control of a heterologous promoter. The alfa-2,3-sialyltransferase may for instance be a human α-2,3-sialyltransferase, known as SIAT4C or STZ (Genbank accession number L23767, see also U.S. Pat. No. 5,494,790). In certain embodiments, sialyltransferase may be over-expressed by integration of the DNA encoding the sialyltransferase into the genome of the second type of complementing cells. In other and preferred embodiments, sialyltransferase is co-expressed with the protein of interest by including the nucleic acid encoding the sialyltransferase in the adenovirus vector, e.g., in operable linkage with an IRES, behind the nucleic acid encoding the protein of interest, or in operable linkage with a separate promoter. Infection of the second type of complementing cells in step c) of the invention with such an adenovirus will ensure expression of both the protein of interest and of the sialyltransferase. Alternatively, the sialyltransferase may be co-expressed from a different adenoviral vector that is co-infected into the second type of complementing cell in step c) of the invention, as described supra.

In general, the production of a recombinant protein in a host cell comprises the introduction of nucleic acid in expressible format into the host cell, culturing the cells under conditions conducive to expression of the nucleic acid and allowing expression of the nucleic acid in the cells. For the purpose of this application "express," "expressing" or "expression" refers to the transcription and translation of a gene encoding a protein.

Nucleic acid encoding a protein in expressible format may be in the form of an expression cassette, and usually requires sequences capable of bringing about expression of the nucleic acid, such as enhancer(s), promoter, polyadenylation signal, and the like. Several promoters can be used for expression of recombinant nucleic acid, and these may comprise viral, mammalian, synthetic promoters, and the like. In certain embodiments, a promoter driving the expression of the nucleic acid of interest is the cytomegalovirus (CMV) immediate early promoter, for instance comprising nt. −735 to +95 from the CMV immediate early gene enhancer/promoter, as this promoter has been shown to give high expression levels in cells expressing E1A of an adenovirus such as the cells of the invention (see, e.g., WO 03/051927). The nucleic acid encoding the protein of interest may be a genomic DNA, a cDNA, synthetic DNA, a combination of these, etc. In certain embodiments, the nucleic acid encoding the protein of interest is a cDNA. If desired, one or more artificial or natural introns may be re-inserted into the cDNA (see, e.g., EP 1283263). It is also possible to remove cryptic splice sites to enhance the expression (see, e.g., U.S. Pat. No. 6,642,028). Codons may be optimized if desired to improve expression (see, e.g., U.S. Pat. No. 6,114,148).

Some well-known and much used promoters for expression in eukaryotic cells comprise promoters derived from viruses, such as adenovirus, e.g., the E1A promoter, promoters derived from cytomegalovirus (CMV), such as the CMV immediate early (IE) promoter (referred to herein as the CMV promoter) (obtainable, for instance, from pcDNA, Invitrogen), promoters derived from Simian Virus 40 (SV40) (Das et al., 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001; Schorpp et al., 1996), actin promoter, an immunoglobulin promoter, heat shock promoters, and the like. Some preferred promoters for obtaining expression in eukaryotic cells, which are suitable promoters in the invention, are the CMV-promoter, a mammalian EF1-alpha promoter, a mammalian ubiquitin promoter such as a ubiquitin C promoter, or a SV40 promoter (e.g., obtainable from pIRES, cat. no. 631605, BD Sciences). Testing for promoter function and strength of a promoter is a matter of routine for a person skilled in the art, and in general may for instance encompass cloning a test gene such as lacZ, luciferase, GFP, etc., behind the promoter sequence, and test for expression of the test gene. Of course, promoters may be altered by deletion, addition, mutation of sequences therein, and tested for functionality, to find new, attenuated, or improved promoter sequences. Strong promoters that give high transcription levels in the second complementing cells of the invention are preferred.

Introduction of the nucleic acid that is to be expressed in a cell, can be done by one of several methods, which as such are known to the person skilled in the art, also dependent on the format of the nucleic acid to be introduced. The methods include but are not limited to transfection, infection, injection, transformation, and the like. For the invention, a recombinant adenovirus is used to infect the second type of complementing cells as host cells for subsequent protein production. Infection takes place by mixing the recombinant adenovirus with the cells, e.g., in a cell culture medium wherein the cells are cultured.

The terms "cell culture medium" and "culture medium" refer to a nutrient solution used for growing mammalian cells that typically provides at least one component from one or more of the following categories: 1) an energy source, usually in the form of a carbohydrate such as glucose; 2) all essential amino acids, and usually the basic set of twenty amino acids plus cysteine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The nutrient solution may optionally be supplemented with one or more components from any of the following categories: 1) hormones and other growth factors as, for example, insulin, transferrin, and epidermal growth factor; 2) salts and buffers as, for example, calcium, magnesium, and phosphate; 3) nucleosides and bases such as, for example, adenosine, thymidine, and hypoxanthine; and 4) protein and tissue hydrolysates. Cell culture media are available from various vendors, and serum-free culture media are nowadays often used for cell culture, because they are more defined than media containing serum. The cells of the invention grow well in serum-containing media as well as in serum-free media. Usually some time is required to adapt the cells from a serum containing medium, such as DMEM+FBS, to a serum-free medium. Examples of serum-free culture medium that are suitable for use in the invention are EX-CELL™ VPRO medium (JRH Biosciences) and AEM medium (Invitrogen). The cells of the invention in general grow adherently in serum-containing media, but are very proficient in growing in suspension to high cell densities ($10\times10^6$ cells/ml and higher) in serum-free culture media, which means that they do not need a surface to adhere to, but remain relatively free from each other and from the walls of the culture vessel during most of the time. Processes for culturing the cells of the invention to high densities and/or for obtaining very high product yields from these cells have been described (WO 2004/099396), incorporated herein by reference. Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components. The conditions for growing or multiplying cells (see, e.g., *Tissue Culture*, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in *Mammalian Cell Biotechnology: a Practical Approach* (M. Butler, ed., IRL Press, 1991).

For small scale experiments, adherent cultures can be used. In preferred embodiments however, the second type of complementing cells in step c) of the invention are in suspension. Suspension cultures are scalable, which is an advantage of such embodiments. PER.C6 cells are very suitable for suspension culture, and can be cultured in suspension to very high cell densities. HEK293 cells can also be cultured in suspension. Thus, in preferred embodiments, the culture of complementing cells in step c) of the invention is a suspension culture.

The protein of interest may be produced by growing the cells of the invention that express the desired protein under a variety of cell culture conditions. For instance, cell culture procedures for the large or small-scale production of proteins are potentially useful within the context of the invention. Procedures including, but not limited to, a fluidized bed bioreactor, hollow fiber bioreactor, roller bottle culture, or stirred tank bioreactor system may be used, in the later two systems, with or without microcarriers, and operated alternatively in a batch, fed-batch, or continuous mode. In preferred embodiments, the cells are in suspension. For simplicity and economic reasons, it is preferred to use a batch process for culturing the cells for the invention. However, if very high cell densities are desired prior to infection, it can be useful to feed culture medium or certain nutrients to the cells in certain embodiments, using methods that have been described previously (fed-batch and perfusion cultures for PER.C6 cells; e.g., WO 2004/099396 and WO 2005/095578, both incorporated by reference herein).

The protein of interest preferably is secreted into the culture medium. Naturally secreted proteins contain secretion signals that bring about secretion of the produced proteins. The sequences of secretion signals are known, and can be engineered into non-naturally secreted proteins if desired. Further, sequences that prevent secretion, e.g., transmembrane domains of receptors, can often be removed so that soluble proteins are obtained. In a preferred embodiment, the expressed protein is collected (isolated), preferably from the culture medium. The protein of interest thus preferably is recovered from the culture medium as a secreted polypeptide. For example, as a first step, the culture medium is centrifuged to remove particulate cell debris. The polypeptide thereafter is preferably purified from contaminant soluble proteins and polypeptides, e.g., by filtration, column chromatography, etc, by methods generally known to the person skilled in the art. Suitable purification steps include methods which were known in the art can be used to maximize the yield of a pure, stable and highly active product and are selected from immunoaffinity chromatography, anion exchange chromatography, size exclusion chromatography, etc., and combinations thereof. In certain embodiments, the harvesting of the protein of interest includes at least one chromatography step. The chromatography can be performed in batch, columns, or in other formats, e.g., using membranes that include functional groups. In certain embodiments, the protein of interest is purified to at least 90%, preferably at least 95%, still more preferably at least 99% purity. In particularly preferred embodiments, the protein of interest is purified and formulated into a pharmaceutical composition that is suitable for administration to human subjects, according to methods known to the skilled person.

Since adenovirus particles are much larger than proteins, a size-exclusion step during purification of the protein will already ensure removal of any inadvertently present adenovirus particles. However, to be on the safe side and overcome the potential problems of possible infectious contaminations in the purified protein samples or in the product directly obtained from the cell culture supernatant containing the secreted recombinant protein of choice, the samples and/or the culture supernatant might be treated with procedures for virus inactivation including heat treatment (dry or in liquid state, with or without the addition of chemical substances including protease inhibitors), which procedures are known to the skilled person. After virus inactivation a further purifying step for removing the chemical substances may be necessary, as known to the skilled person. The PER.C6 cells of the invention are available free of adventitious virus and TSE and a well-documented history is available for these cells, so that they can be used to produce proteins in a safe manner.

In step c) of the method of the invention, the second type of complementing cells are infected with recombinant adenovirus particles. This can suitably be performed along a very wide range of multiplicity of infections (moi), generally the moi is between 1 and 10000 virus particles (vp)/cell. It has been surprisingly found herein that lower moi's work as good or better than higher moi's, so that in preferred embodiments the moi is between 1 and 2000 vp/cell, more preferably between 1 and 1000 vp/cell, more preferably between 1 and 200 vp/cell, still more preferably between 1 and 100 vp/cell, typically between 10 and 100 vp/cell, e.g., about 10, 20, 30, 40, 50, 60, 70, 80, or 90 vp/cell. The advantage of the use of lower moi's (100 vp/cell or lower) is that less virus is required, so that step b) of the invention becomes less burdensome: more cells in step c) can be infected with material obtained in step b). This makes the system economically more attractive since less culture media, less time, and smaller reaction vessels are required for step b) then when high moi's would be required for step c). One infectious unit (IU) generally equals about 1-100 vp (depending on variations in batch quality), more typically equals between 5-20 vp. In certain embodiments of the invention, the second type of complementing cells are infected with about between 1-10 IU of the recombinant adenovirus particles obtained in step b) of the invention.

For the methods of the invention, the moi does not necessarily have to be determined prior to infection of step c). It is for instance possible to establish an estimation of the moi for certain conditions with a specific vector, and infect the culture of the second type of complementing cells with an amount of virus based on such estimation. It is also possible to infect several cultures of the second type of complementing cells each with a different amount of virus particles, and empirically find out which worked best when the protein is harvested. If desired, the experiment may be scaled up using the findings of this empirical determination.

In certain embodiments, the recombinant adenovirus particles of step b) of the invention are purified first, and subsequently the purified recombinant adenovirus particles are used to infect the second type of complementing cells in step c). Purification of recombinant adenovirus particles can be done by a variety of previously described methods, including CsCl centrifugation, filtration and chromatography, and the like (see, e.g., WO 2005/080556 and references therein, and WO 2006/108707 and references therein, for a variety of useful methods for purification of recombinant adenovirus, all incorporated by reference herein). One advantage of such a method is the high degree of control over the virus quality and quantity that is achieved upon purification, before the virus is used in step c) of the invention.

However, purification of the recombinant adenovirus particles is a lengthy process typically taking several weeks to months. Therefore it is highly preferable to use the recombinant virus particles of step b) immediately, i.e., without further purification steps, for the infection in step c) of the invention. It is shown herein that this is possible, and surprisingly gives very good results. The results with the so-called 'crude' virus, i.e., culture medium of step b) from which the first type of complementing cells have been removed, e.g., by centrifugation, are at least as good as with purified virus, regarding quantity and quality of the protein of interest obtained, while the methods wherein the crude virus is used are significantly shorter. The advantage is thus that the method of the invention becomes very fast if no virus purification steps are performed. The present methods allow use of such fast methods, and no virus purification, nor exact determination of the moi, is required to obtain high yields of intact protein of interest in a very fast process. Therefore, in certain embodiments, the recombinant adenovirus particles in step b) are obtained in a culture medium, and the culture medium containing the recombinant adenovirus particles is separated from the first type of complementing cells to obtain a crude adenovirus particle composition, and the crude adenovirus particle composition is used for the infection of the second type of complementing cells in step c). In advantageous embodiments, a freeze-thaw cycle is performed with the culture of step b) to release more of the recombinant adenovirus particles. This increases the amount of particles that can be used for step c), and has the additional advantage to kill the first type of complementing cells, and thus further decreases the chance that such cells inadvertently end up in the culture of step c). The separation of the medium and the virus particles from the cells can be done using simple methods such as centrifugation or filtration, and the like, making use of the large size and weight differences between cells and virus particles, in a manner known to the skilled person.

It will be clear that step b) can be performed first and independently from step c), to obtain the recombinant adenovirus particle composition. The recombinant adenovirus can then for instance optionally be stored and used for step c) at a later time if desired. Therefore, step c) is a possible embodiment of the invention as well. The invention therefore further provides a method for producing a protein of interest, the method comprising: infecting a culture of complementing cells with a recombinant adenoviral particle that has a genome comprising nucleic acid encoding the protein of interest under control of a promoter, wherein the genome has deletions in a first region and in a second region of the adenovirus genome, wherein each of the first region and the second region is required for adenoviral genome replication and/or adenovirus particle formation, wherein the complementing cells express protein from the first region of the adenovirus genome but not protein from the second region of the adenovirus genome, to produce the protein of interest, and harvesting the protein of interest. In preferred embodiments hereof, the first region of the adenovirus is E1. In certain embodiments, the second region of the adenovirus is E2A.

Preferred complementing cells of this aspect express adenovirus E1 protein, such as HEK293 cells, 911 cells, PER.C6 cells, and the like. The most preferred complementing cells for this aspect are PER.C6 cells.

To illustrate the invention, the following examples are provided, not intended to limit the scope of the invention. The human erythropoietin (EPO) molecule contains four carbohydrate chains. Three contain N-linkages to asparagines, and one contains an O-linkage to a serine residue. The importance of glycosylation in the biological activity of EPO has been well documented (Delorme et al., 1992; Yamaguchi et al., 1991). The cDNA encoding human EPO was cloned and expressed in PER.C6 cells and PER.C6/E2A cells, expression was shown, and the glycosylation pattern was analyzed.

The practice of this invention will employ, unless otherwise indicated, conventional techniques of immunology, molecular biology, microbiology, cell biology, and recombinant DNA, which are within the skill of the art. See, e.g., Sambrook, Fritsch and Maniatis, *Molecular Cloning: A Laboratory Manual*, 2nd edition, 1989; *Current Protocols in Molecular Biology*, F. M. Ausubel, et al., eds, 1987; the series *Methods in Enzymology* (Academic Press, Inc.); *PCR2: A Practical Approach*, M. J. MacPherson, B. D. Hams, G. R. Taylor, eds, 1995; *Antibodies: A Laboratory Manual*, Harlow and Lane, eds, 1988.

EXAMPLES

Example 1

Construction of Basic Expression Vectors

Plasmid pcDNA3.1/Hygro(−) (Invitrogen) was digested with NruI and EcoRV, dephosphorylated at the 5' termini by Shrimp Alkaline Phosphatase (SAP, GIBCO Life Tech.) and the plasmid fragment lacking the immediate early enhancer and promoter from CMV was purified from gel. Plasmid pAdApt (Crucell N V of Leiden, N L), containing the full length CMV enhancer/promoter (−735 to +95) next to overlapping Adeno-derived sequences to produce recombinant adenovirus, was digested with AvrII, filled in with Klenow polymerase and digested with HpaI; the fragment containing the CMV enhancer and promoter was purified over agarose gel. This CMV enhancer and promoter fragment was ligated bluntiblunt to the NruI/EcoRV fragment from pcDNA3.1/Hygro(−). The resulting plasmid was designated pcDNA2000/Hyg(−).

Figure 2:
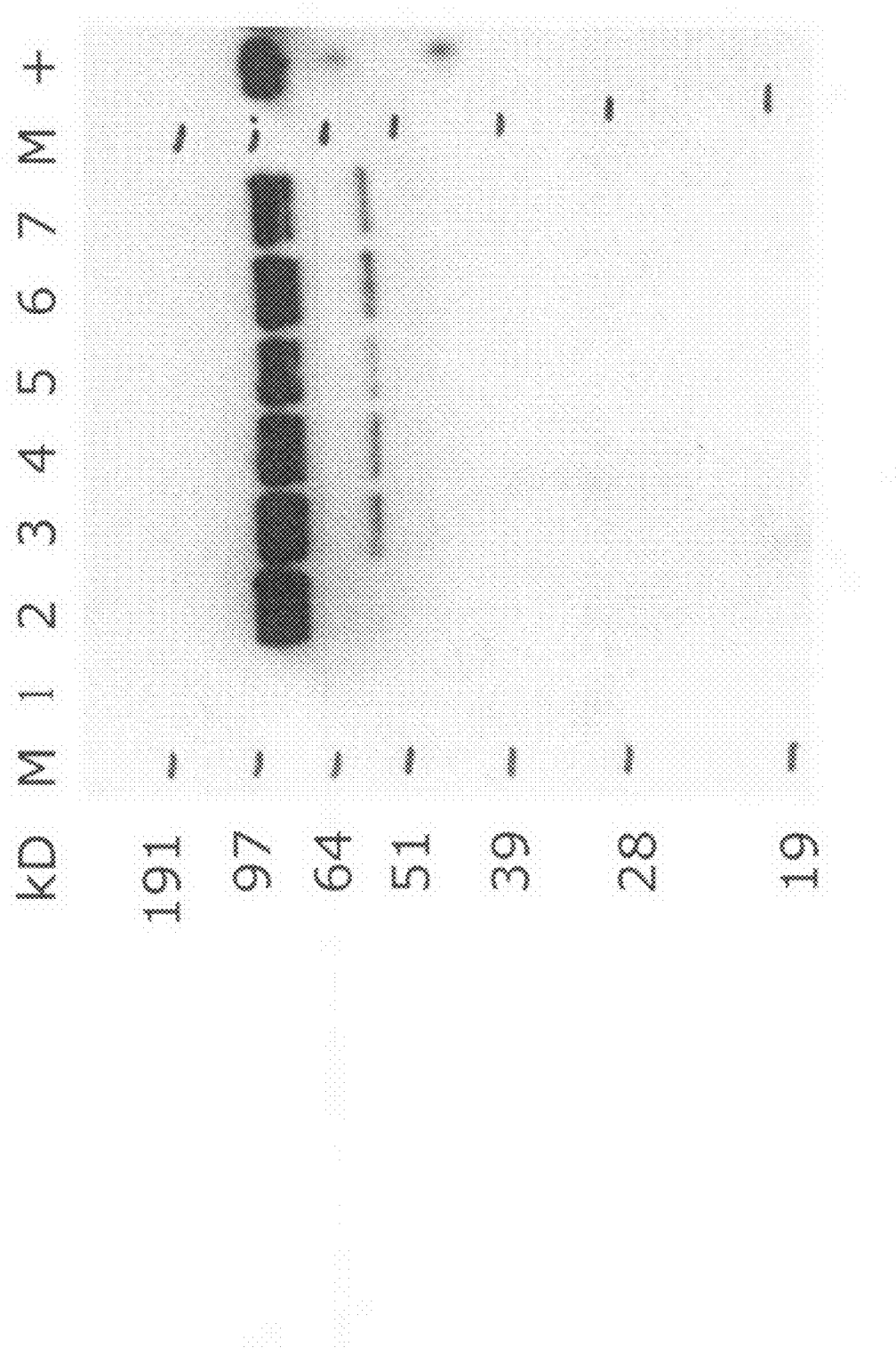
FIG. 2. Analysis of S565 generated in PER.C6 cells, 3 days after infection with various MOI's of Ad5.dE1dE2A.S565 viruses. PER.C6 cell cultures were infected with 0, 100, 250, 500, 1000, 1500 and 2000 vp/cell Ad5.dE1.dE2A.S565 (lanes 1-7). Medium samples were separated using SDS-PAGE and analyzed on western blot. S565 was detected using anti-c-myc monoclonal antibody. Molecular weight marker (M) is depicted in the picture. Purified S565 transiently produced by plasmid transfection in HEK293 cells was included as positive control (+). See example 36 for details.
Figure 4:
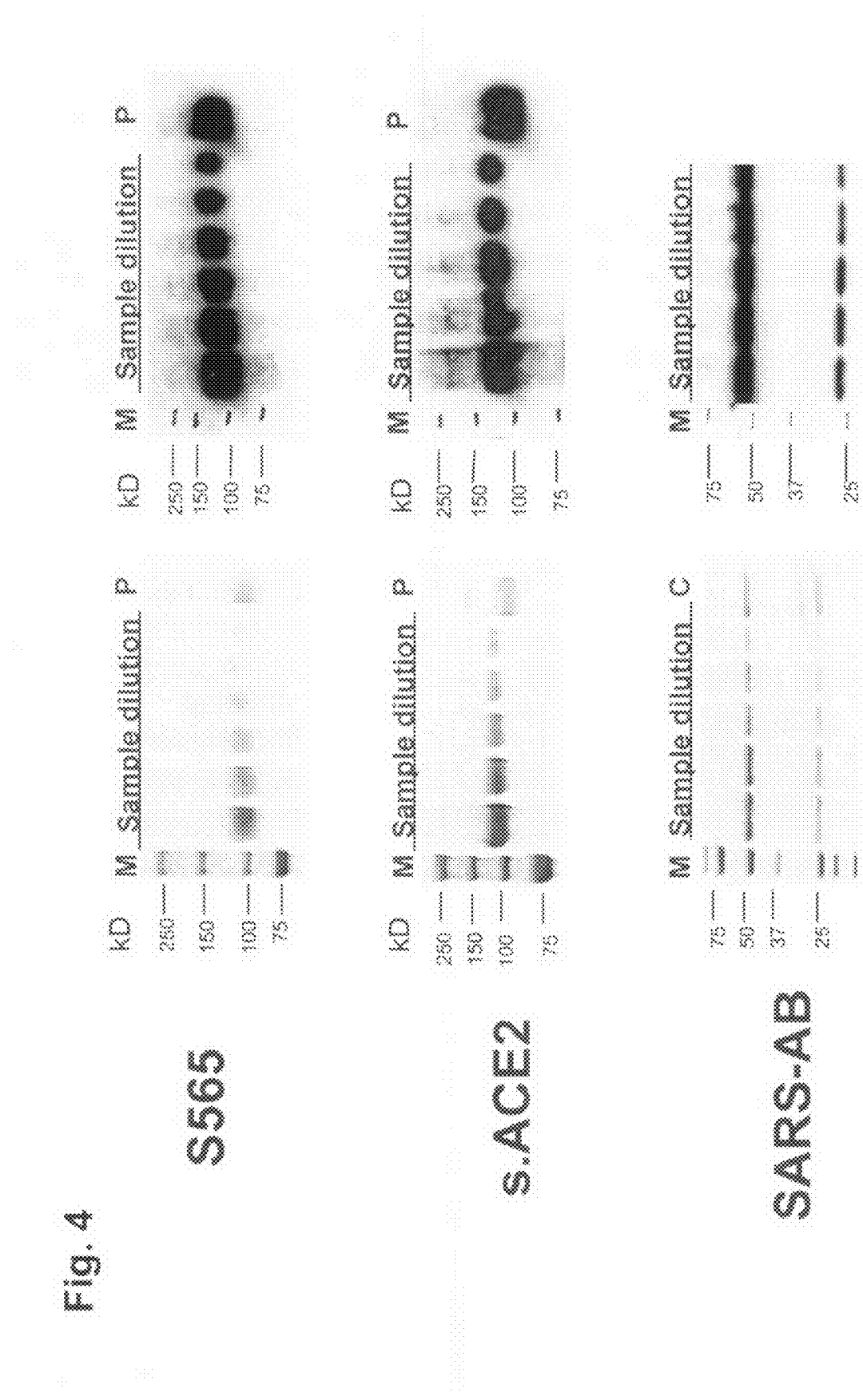
FIG. 4. Integrity of transiently expressed and purified S565, s.ACE2 and SARS-AB proteins. Roller bottle PER.C6 cultures were infected with 30 vp/cell of Ad5.dE1dE2A.S565, Ad5.dE1dE2A.s.ACE2 or Ad5.dE1.dE2A.SARS-AB viruses. Proteins were separated on SDS-PAGE gels and analyzed on western blots. S565 and s.ACE2 were visualized with mouse-anti-c.myc (HRP-conjugated) monoclonal antibody. SARS-AB was visualized using donkey-anti-human IgG (HRP-conjugated) monoclonal antibody using an ECL-detection system. Molecular weight marker (M) is depicted in the picture. Purified S565 transiently produced in HEK293 cells (P), and stably produced CR3014 (anti-SARS antibody) on PER.C6 cells were included as positive controls (C). See example 36 for details.

Plasmid pcDNA2000/Hyg(−) was digested with PmlI, and the linearized plasmid lacking the Hygromycin resistance marker gene was purified from gel and religated. The resulting plasmid was designated pcDNA2000. Plasmid pcDNA2000 was digested with PmlI and dephosphorylated by SAP at both termini. Plasmid pIG-GC9 containing the wild-type human DHFR cDNA (Havenga et al., 1998) was used to obtain the wild-type DHFR-gene by polymerase chain reaction (PCR) with introduced, noncoding PmlI sites upstream and down stream of the cDNA. PCR primers that were used were DHFR up: 5'-GAT CCA CGT GAG ATC TCC ACC ATG GTT GGT TCG CTA AAC TG-3' (SEQ ID NO:1), corresponding to the SEQUENCE LISTING of U.S. patent application Ser. No. 10/234,007, now U.S. Pat. No. 7,132,280 (hereafter referred to as 'the '007 application') of Bout et al., the contents of the entirety of which are incorporated by this reference) and DHFR down: 5'-GAT CCA CGT GAG ATC TTT AAT CAT TCT TCT CAT ATAC-3' (SEQ ID NO:2) corresponding to the incorporated '007 application. The PCR-product was digested with PmlI and used for ligation into pcDNA2000 (digested with PmlI, and dephosphorylated by SAP) to obtain pcDNA2000/DHFRwt (FIG. 1 of the incorporated '007 application). Wild-type sequences and correctly used cloning sites were confirmed by double stranded sequencing. Moreover, a mutant version of the human DHFR gene (DHFRm) was used to reach a 10,000-fold higher resistance to methotrexate in PER.C6 and PER.C6/E2A by selection of a possible integration of the transgene in a genomic region with high transcriptional activity. This mutant carries an amino acid substitution in position 32 (phenylalanine to serine) and position 159 (leucine to proline) introduced by the PCR procedure. PCR on plasmid pIG-GC12 (Havenga et al., 1998) was used to obtain the mutant version of human DHFR. Cloning of this mutant is comparable to wild-type DHFR. The plasmid obtained with mutant DHFR was designated pcDNA2000/DHFRm.

pIPspAdapt 6 (Galapagos Genomics of Belgium) was digested with AgeI and BamHI restriction enzymes. The resulting polylinker fragment has the following sequence: 5'-ACC GGT GAA TTC GGC GCG CCG TCG ACG ATA TCG ATC GGA CCG ACG CGT TCG CGA GCG GCC GCA ATT CGC TAG CGT TAA CGG ATC C -3' (SEQ ID NO:3) corresponding to the incorporated '007 application. The used AgeI and BamHI recognition sites are underlined. This fragment contains several unique restriction enzyme recognition sites and was purified over agarose gel and ligated to an AgeI/BamHI-digested and agarose gel-purified pcDNA2000/DHFRwt plasmid. The resulting vector was named pcDNA2001/DHFRwt (FIG. 2 of the incorporated '007 application).

pIPspAdapt7 (Galapagos of Belgium) is digested with AgeI and BamHI restriction enzymes and has the following sequence: 5'-ACC GGT GAA TTG CGG CCG CTC GCG AAC GCG TCG GTC CGT ATC GAT ATC GTC GAC GGC GCG CCG AAT TCG CTA GCG TTA ACG GAT CC-3' (SEQ ID NO:4) corresponding to the incorporated '007 application. The used AgeI and BamHI recognition sites are underlined in the incorporated '007 application. The polylinker fragment contains several unique restriction enzyme recognition sites (different from pIPspAdapt6), which are purified over agarose gel and ligated to an AgeI/BamHI-digested and agarose gel-purified pcDNA2000/DHFRwt. This results in pcDNA2002/DHFRwt (FIG. 3 of the incorporated '007 application).

pcDNA2000/DHFRwt was partially digested with restriction enzyme PvuII. There are two PvuII sites present in this plasmid and cloning was performed into the site between the SV40 poly(A) and ColE1, not the PvuII site down stream of the BGH poly(A). A single site-digested mixture of plasmid was dephosphorylated with SAP and blunted with Klenow enzyme and purified over agarose gel. pcDNA2000/DHFRwt was digested with MunI and PvuII restriction enzymes and filled in with Klenow and free nucleotides to have both ends blunted. The resulting CMV promoter-linker-BGH poly(A)-containing fragment was isolated over gel and separated from the vector. This fragment was ligated into the partially digested and dephosphorylated vector and checked for orientation and insertion site. The resulting plasmid was named pcDNAs3000/DHFRwt (FIG. 4 of the incorporated '007 application).

Example 2

Construction of EPO Expression Vectors

Figure 5:
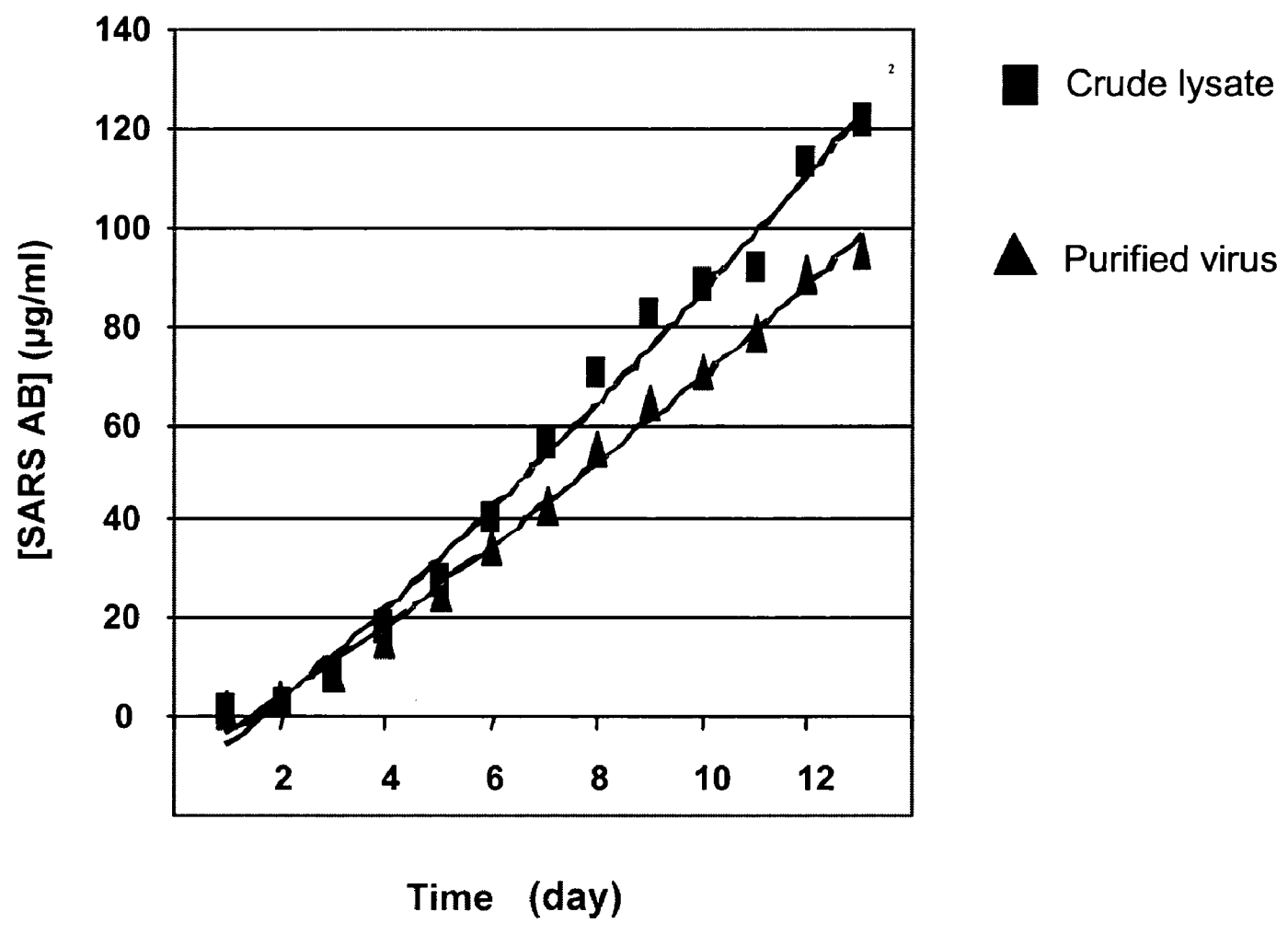

The full length human EPO cDNA was cloned, employing oligonucleotide primers EPO-START: 5' AAA AAG GAT CCG CCA CCA TGG GGG TGC ACG AAT GTC CTG CCT G-3' (SEQ ID NO:5) corresponding to the incorporated '007 application and EPO-STOP: 5'-AAA AAG GAT CCT CAT CTG TCC CCT GTC CTG CAG GCC TC-3' (SEQ ID NO:6) corresponding to the incorporated '007 application (Cambridge Bioscience Ltd.) in a PCR on a human adult liver cDNA library. The amplified fragment was cloned into pUC18 linearized with BamHI. Sequence was checked by double stranded sequencing. This plasmid containing the EPO cDNA in pUC18 was digested with BamHI and the EPO insert was purified from agarose gel. Plasmids pcDNA2000/DHFRwt and pcDNA2000/DHFRm were linearized with BamHI and dephosphorylated at the 5' overhang by SAP, and the plasmids were purified from agarose gel. The EPO cDNA fragment was ligated into the BamHI sites of pcDNA2000/DHFRwt and pcDNA2000/DHFRm; the resulting plasmids were designated pEPO2000/DHFRwt (FIG. 5 of the incorporated '007 application) and pEPO2000/DHFRm.

The plasmid pMLPI.TK (described in PCT International Patent Publication No. WO 97/00326) is an example of an adapter plasmid designed for use in combination with improved packaging cell lines like PER.C6 (described in PCT International Patent Publication No. WO 97/00326 and U.S. Pat. No. 6,033,908 to Bout et al. (Mar. 7, 2000), the contents of both of which are incorporated by this reference). First, a PCR fragment was generated from pZipDMo+PyF101(N—) template DNA (described in International Patent Application No. PCT/NL96/00195) with the following primers: LTR-1 (5'-CTG TAC GTA CCA GTG CAC TGG CCT AGG CAT GGA AAA ATA CAT AAC TG-3' (SEQ ID NO:7) corresponding to the incorporated '007 application and LTR-2 (5'-GCG GAT CCT TCG AAC CAT GGT AAG CTT GGT ACC GCT AGC GTT AAC CGG GCG ACT CAG TCA ATC G-3' (SEQ ID NO:8) corresponding to the incorporated '007 application). The PCR product was then digested with BamHI and ligated into pMLP10 (Levrero et al., 1991), that was digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990, using the following primers: HSAI (5'-GCG CCA CCA TGG GCA GAG CGA TGG TGG C-3' (SEQ ID NO:9) corresponding to the incorporated '007 application) and HSA2 (5'-GTT AGA TCT AAG CTT GTC GAC ATC GAT CTA CTA ACA GTA GAG ATG TAG AA-3' (SEQ ID NO:10) corresponding to the incorporated '007 application). The 269 bp PCR fragment was subcloned in a shuttle vector using NcoI and BglII sites. Sequencing confirmed incorporation of the correct coding sequence of the HSA gene, but with an extra TAG insertion directly following the TAG stop codon. The coding region of the HSA gene, including the TAG duplication, was then excised as a NcoI/SalI fragment and cloned into a 3.5 kb NcoI/BstBI cut pLTR10, resulting in pLTR-HSA10. This plasmid was digested with EcoRI and BamHI, after which the fragment, containing the left ITR, the packaging signal, the L420 promoter and the HSA gene, was inserted into vector pMLPI.TK digested with the same enzymes and thereby replacing the promoter and gene sequences, resulting in the new adapter plasmid pAd5/L420-HSA.

The pAd5/L420-HSA plasmid was digested with AvrII and BglII followed by treatment with Klenow and ligated to a blunt 1570 bp fragment from pcDNA1/amp (Invitrogen) obtained by digestion with HhaI and AvrII followed by treatment with T4 DNA polymerase. This adapter plasmid was named pAd5/CLIP.

To enable removal of vector sequences from the left ITR, pAd5/L420-HSA was partially digested with EcoRI and the linear fragment was isolated. An oligo of the sequence 5' TTA AGT CGA C-3' (SEQ ID NO: 11) corresponding to the incorporated '007 application was annealed to itself, resulting in a linker with a SalI site and EcoRI overhang. The linker was ligated to the partially digested pAd5/L420-HSA vector and clones were selected that had the linker inserted in the EcoRI site 23 bp upstream of the left adenovirus ITR in pAd5/L420-HSA, resulting in pAd5/L420-HSA.sal.

To enable removal of vector sequences from the left ITR, pAd5/CLIP was also partially digested with EcoRI and the linear fragment was isolated. The EcoRI linker 5' TTA AGT CGA C-3' (SEQ ID NO: 12) corresponding to the incorporated '007 application was ligated to the partially digested pAd5/CLIP vector and clones were selected that had the linker inserted in the EcoRI site 23 bp upstream of the left adenovirus ITR, resulting in pAd5/CLIP.sal. The vector pAd5/L420-HSA was also modified to create a PacI site upstream of the left ITR. Hereto, pAd5/L420-HSA was digested with EcoRI and ligated to a PacI linker (5'-AAT TGT CTT AAT TAA CCG CTT AA-3' (SEQ ID NO:13) corresponding to the incorporated '007 application). The ligation mixture was digested with PacI and religated after isolation of the linear DNA from agarose gel to remove concatamerized linkers. This resulted in adapter plasmid pAd5/L420-HSA.pac.

This plasmid was digested with AvrII and BglII. The vector fragment was ligated to a linker oligonucleotide digested with the same restriction enzymes. The linker was made by annealing oligos of the following sequence: PLL-1 (5'-GCC ATC CCT AGG AAG CTT GGT ACC GGT GAA TTC GCT AGC GTT AAC GGA TCC TCT AGA CGA GAT CTG G-3' (SEQ ID NO:14) corresponding to the incorporated '007 application) and PLL-2 (5'-CCA GAT CTC GTC TAG AGG ATC CGT TAA CGC TAG CGA ATT CAC CGG TAC CAA GCT TCC TAG GGA TGG C-3' (SEQ ID NO:15) corresponding to the incorporated '007 application). The annealed linkers were separately ligated to the AvrII/BglII-digested pAd5/L420-HSA.pac fragment, resulting in pAdMire.pac. Subsequently, a 0.7 kb ScaI/BsrGI fragment from pAd5/CLIP.sal containing the sal linker was cloned into the ScaI/BsrGI sites of the pAdMire.pac plasmid after removal of the fragment containing the pac linker. This resulting plasmid was named pAdMire.sal.

Plasmid pAd5/L420-HSA.pac was digested with AvrII and 5' protruding ends were filled in using Klenow enzyme. A second digestion with HindIII resulted in removal of the L420 promoter sequences. The vector fragment was isolated and ligated separately to a PCR fragment containing the CMV promoter sequence. This PCR fragment was obtained after amplification of CMV sequences from pCMVLacI (Stratagene) with the following primers: CMVplus (5'-GAT CGG TAC CAC TGC AGT GGT CAA TAT TGG CCA TTA GCC-3' (SEQ ID NO:16) corresponding to the incorporated '007 application) and CMVminA (5'-GAT CAA GCT TCC AAT GCA CCG TTC CCG GC-3' (SEQ ID NO:17) corresponding to the incorporated '007 application). The PCR fragment was first digested with PstI after which the 3'-protruding ends were removed by treatment with T4 DNA polymerase. Then the DNA was digested with HindIII and ligated into the AvrII/

HindIII-digested pAd5/L420-HSA.pac vector. The resulting plasmid was named pAd5/CMV-HSA.pac. This plasmid was then digested with HindIII and BamHI and the vector fragment was isolated and ligated to the HindIII/BglII polylinker sequence obtained after digestion of pAdMire.pac. The resulting plasmid was named pAdApt.pac and contains nucleotides −735 to +95 of the human CMV promoter/enhancer (M. Boshart et al., 1985).

Figure 6:
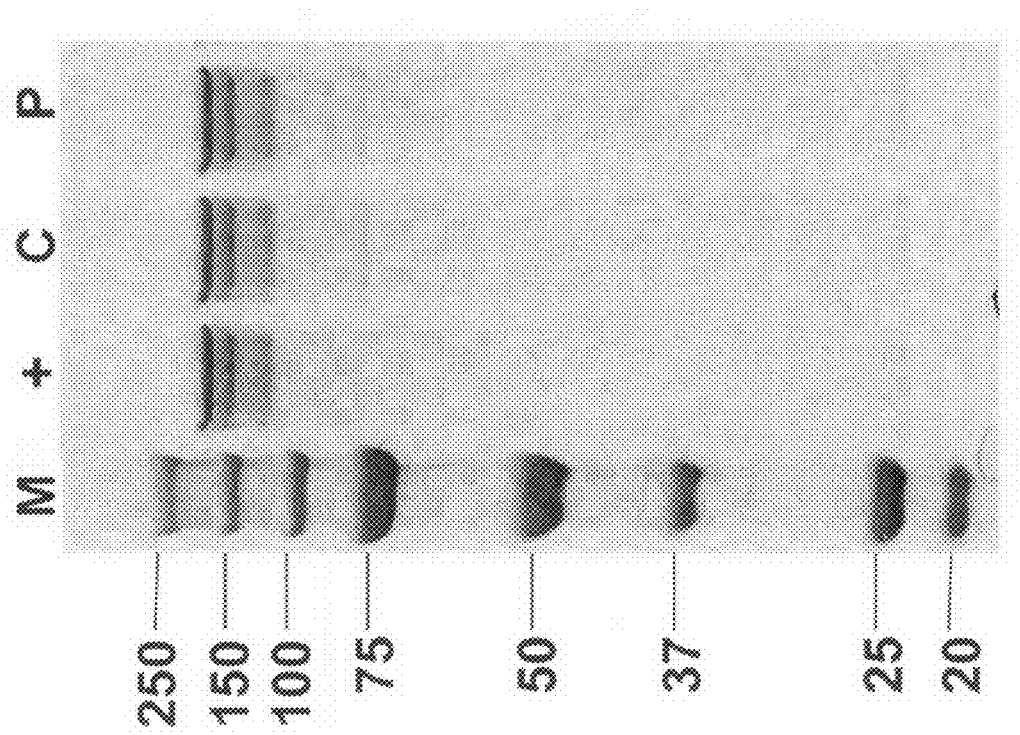
FIG. 6. SDS-PAGE analysis, under non-reduced conditions, of purified SARS-AB batches transiently produced in PER.C6 cells. Cell cultures were infected in parallel with 4 IU/cell of purified virus (P) and crude lysates (C) of Ad5.dE1.dE2A.SARS-AB. Molecular weight marker (M) is indicated. Stably produced SARS-AB was included as positive control (+). See example 36 for details.

The full length human EPO cDNA (Genbank accession number: MI 1319) containing a perfect Kozak sequence for proper translation was removed from the pUC18 backbone after a BamHI digestion. The cDNA insert was purified over agarose gel and ligated into pAdApt.pac, which was also digested with BamHI, subsequently dephosphorylated at the 5' and 3' insertion sites using SAP and also purified over agarose gel to remove the short BamHI-BamHI linker sequence. The obtained circular plasmid was checked with KpnI, DdeI and NcoI restriction digestions that all gave the right size bands. Furthermore, the orientation and sequence was confirmed by double stranded sequencing. The obtained plasmid with the human EPO cDNA in the correct orientation was named pAdApt.EPO (FIG. 6 of the incorporated '007 application).

Example 3

Construction of UBS-54 Expression Vectors

The constant domains (CH1, -2 and -3) of the heavy chain of the human immunoglobulin G1 (IgG1) gene including intron sequences and connecting ("Hinge") domain were generated by PCR using an upstream and a down stream primer. The sequence of the upstream primer (CAMH-UP) is 5'-GAT CGA TAT CGC TAG CAC CAA GGG CCC ATC GGT C-3' (SEQ ID NO: 18) corresponding to the incorporated '007 application, in which the annealing nucleotides are depicted in italics and two sequential restriction enzyme recognition sites (EcoRV and NheI) are underlined.

The sequence of the down stream primer (CAMH-DOWN) is: 5'-GAT CGT TTA AAC TCA TTT ACC CGG AGA CAG-3' (SEQ ID NO:19) corresponding to the incorporated '007 application, in which the annealing nucleotides are depicted in italics and the introduced PmeI restriction enzyme recognition site is underlined.

The order in which the domains of the human IgG1 heavy chain were arranged is as follows: CH1-intron-Hinge-intron-CH2-intron-CH3. The PCR was performed on a plasmid (pCMgamma NEO Skappa Vgamma Cgamma hu) containing the heavy chain of a humanized antibody directed against D-dimer from human fibrinogen (Vandamme et al., 1990). This antibody was designated "15C5" and the humanization was performed with the introduction of the human constant domains including intron sequences (Bulens et al., 1991). The PCR resulted in a product of 1621 nucleotides. The NheI and PmeI sites were introduced for easy cloning into the pcDNA2000/Hyg(−) polylinker. The NheI site encoded two amino acids (Ala and Ser) that are part of the constant region CH1, but that did not hybridize to the DNA present in the template (Crowe et al., 1992).

Figure 7A:
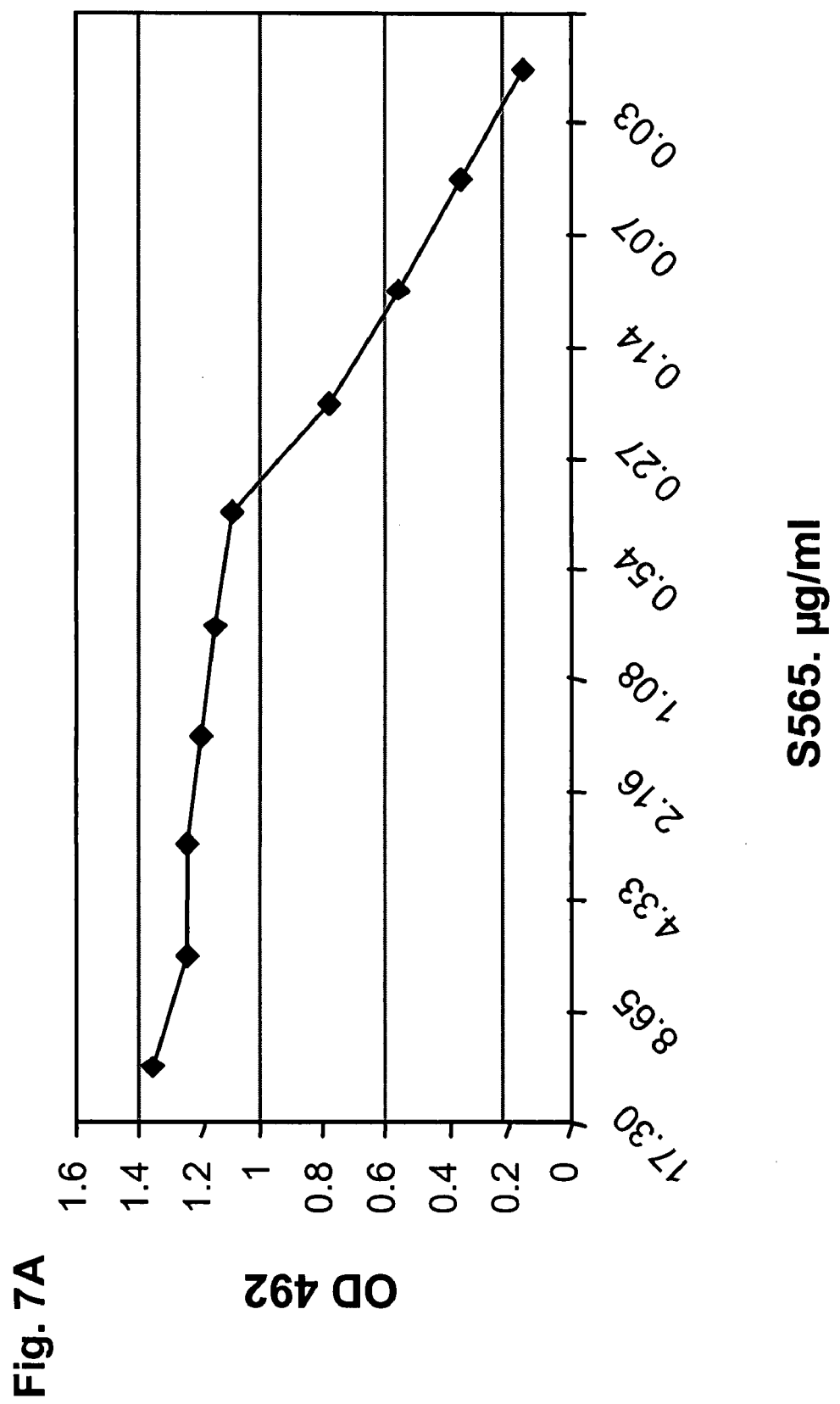
FIG. 7. A) Binding of CR3014 (anti-SARS antibody produced in stably transfected PER.C6 cells) to transiently produced S565.
Figure 7B:
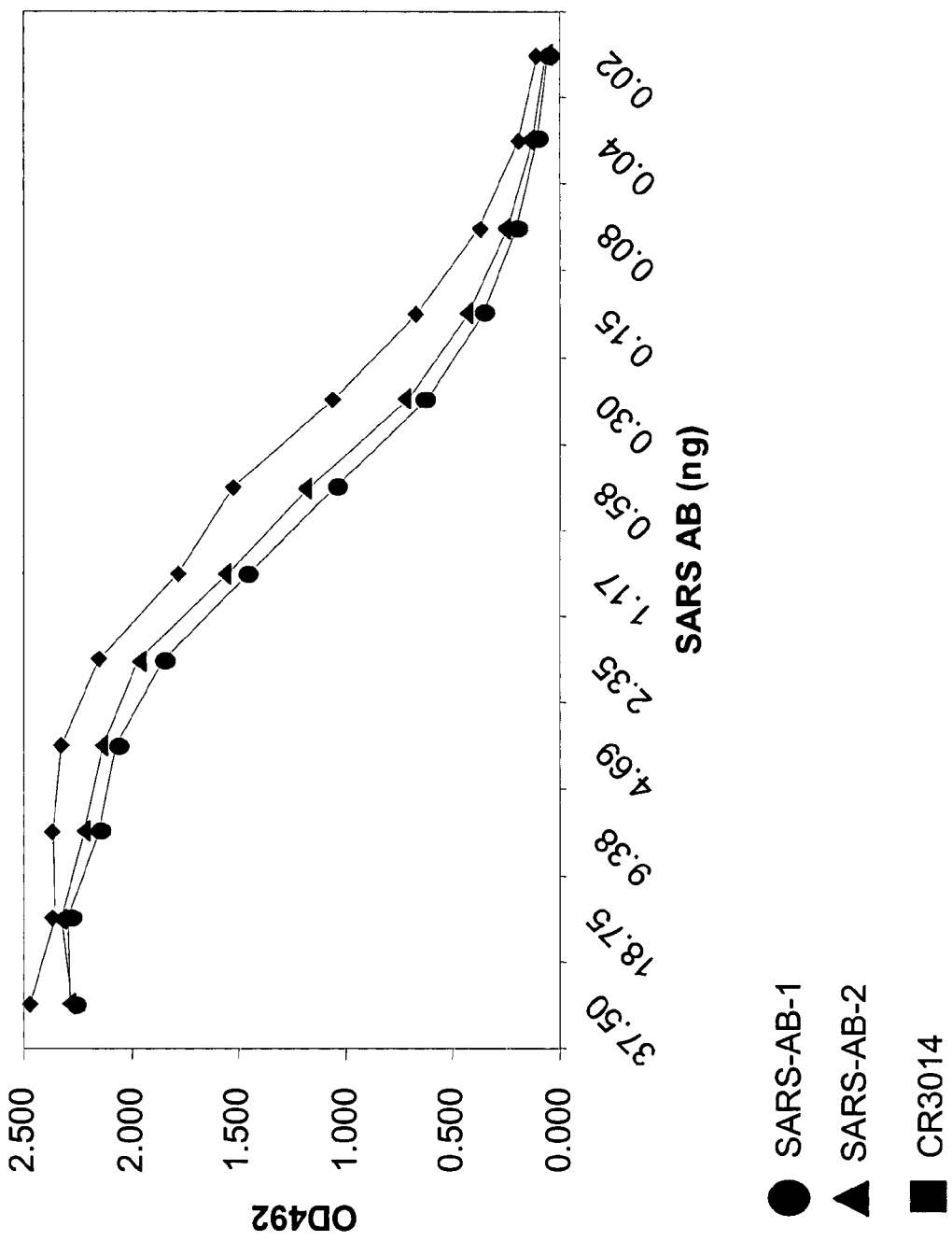

The PCR product was digested with NheI and PmeI restriction enzymes, purified over agarose gel and ligated into a NheI and PmeI-digested and agarose gel-purified pcDNA2000/Hygro(−). This resulted in plasmid pHC2000/Hyg(−) (FIG. 7 of the incorporated '007 application), which can be used for linking the human heavy chain constant domains, including introns to any possible variable region of any identified immunoglobulin heavy chain for humanization.

The constant domain of the light chain of the human immunoglobulin (IgG1) gene was generated by PCR using an upstream and a down stream primer: The sequence of the upstream primer (CAML-UP) is 5'-GAT CCG TAC GGT GGC TGCACCATC TGT C-3' (SEQ ID NO:20) corresponding to the incorporated '007 application, in which the annealing nucleotides are depicted in italics and an introduced SunI restriction enzyme recognition site is underlined.

The sequence of the down stream primer (CAML-DOWN) is 5'-GAT CGT TTA AAC CTA ACA CTC TCC CCT GTT G-3' (SEQ ID NO:21) corresponding to the incorporated '007 application, in which the annealing nucleotides are in italics and an introduced PmeI restriction enzyme recognition site is underlined.

The PCR was performed on a plasmid (pCMkappa DHFR13 15C5 kappa humanized) carrying the murine signal sequence and murine variable region of the light chain of 15C5 linked to the constant domain of the human IgG1 light chain (Vandamme et al., 1990; Bulens et al., 1991).

The PCR resulted in a product of 340 nucleotides. The SunI and PmeI sites were introduced for cloning into the pcDNA2001/DHFRwt polylinker. The SunI site encoded two amino acids (Arg and Thr) of which the threonine residue is part of the constant region of human immunoglobulin light chains, while the arginine residue is part of the variable region of CAMPATH-1H (Crowe et al., 1992). This enabled subsequent 3' cloning into the SunI site, which was unique in the plasmid.

The PCR product was digested with SunI and PmeI restriction enzymes purified over agarose gel, ligated into a BamHI, PmeI-digested, and agarose gel-purified pcDNA2001/DHFRwt, which was blunted by Klenow enzyme and free nucleotides. Ligation in the correct orientation resulted in loss of the BamHI site at the 5' end and preservation of the SunI and PmeI sites. The resulting plasmid was named pLC2001/DHFRwt (FIG. 8 of the incorporated '007 application), which plasmid can be used for linking the human light chain constant domain to any possible variable region of any identified immunoglobulin light chain for humanization.

pNUT-C gamma (Huls et al., 1999) contains the constant domains, introns and hinge region of the human IgG1 heavy chain (Huls et al., 1999) and received the variable domain upstream of the first constant domain. The variable domain of the gamma chain of fully humanized monoclonal antibody UBS-54 is preceded by the following leader peptide sequence: MACPGFLWALVISTCLEFSM (SEQ ID NO:22) corresponding to the incorporated '007 application (sequence: 5'-ATG GCA TGC CCT GGC TTC CTG TGG GCA CTT GTG ATC TCC ACC TGT CTT GAA TTT TCC ATG-3') (SEQ ID NO:23) corresponding to the incorporated '007 application. This resulted in an insert of approximately 2 kb in length. The entire gamma chain was amplified by PCR using an upstream primer (UBS-UP) and the down stream primer CAMH-DOWN. The sequence of UBS-UP is as follows: 5'-GAT CAC GCG TGC TAG CCA CCA TGG CAT GCC CTG GCT TC-3' (SEQ ID NO:24) corresponding to the incorporated '007 application in which the introduced MluI and NheI sites are underlined and the perfect Kozak sequence is italicized.

The resulting PCR product was digested with NheI and PmeI restriction enzymes, purified over agarose gel and ligated to the pcDNA2000/Hygro(−) plasmid that is also digested with NheI and PmeI, dephosphorylated with tSAP and purified over gel. The resulting plasmid was named pUBS-Heavy2000/Hyg(−) (FIG. 9 of the incorporated '007 application). pNUT-C kappa contains the constant domain of the light chain of human IgG1 kappa (Huls et al., 1999) and received the variable domain of fully humanized monoclonal antibody UBS-54 kappa chain preceded by the following leader peptide: MACPGFLWALVISTCLEFSM (SEQ ID NO:25) corresponding to the incorporated '007 application (sequence: 5'-ATG GCA TGC CCT GGC TTC CTG TGG GCA CTT GTG ATC TCC ACC TGT CTT GAA TTT TCC ATG-3' (SEQ ID NO:26) corresponding to the incorporated '007 application, for details on the plasmid see U-BiSys of Utrecht, NL). This resulted in an insert of approximately 1.2 kb in length.

The entire insert was amplified by PCR using the upstream primer UBS-UP and the down stream primer CAML-DOWN, hereby modifying the translation start site. The resulting PCR product was digested with NheI and PmeI restriction enzymes, purified over agarose gel and ligated to pcDNA2001/DHFRwt that was also digested with NheI and PmeI, dephosphorylated by tSAP and purified over gel, resulting in pUBS-Light2001/DHFRwt (FIG. 10 of the incorporated '007 application). To remove the extra intron which is located between the variable domain and the first constant domain that is present in pNUT-Cgamma and to link the signal peptide and the variable domain to the wild-type constant domains of human IgG1 heavy chain, lacking a number of polymorphisms present in the carboxy-terminal constant domain in pNUT-Cgamma, a PCR product is generated with primer UBS-UP and primer UBSHV-DOWN that has the following sequence: 5'-GAT CGC TAG CTG TCGAGA CGG TGA CCA G-3' (SEQ ID NO:27) corresponding to the incorporated '007 application, in which the introduced NheI site is underlined and the annealing nucleotides are italicized. The resulting PCR product is digested with NheI restriction enzyme, purified over gel and ligated to a NheI-digested and SAP-dephosphorylated pHC2000/Hyg(−) plasmid that was purified over gel. The plasmid with the insert in the correct orientation and reading frame is named pUBS2-Heavy2000/Hyg(−) (FIG. 11 of the incorporated '007 application).

For removal of an extra intron which is located between the variable domain and the constant domain that is present in pNUT-Ckappa and to link the signal peptide and the variable domain to the wild-type constant domain of human IgG1 light chain, a PCR product was generated with primer UBS-UP and primer UBSLV-DOWN that has the following sequence: 5'-GAT CCG TAC GCT TGA TCT CCA CCT TGG TC -3' (SEQ ID NO:28) corresponding to the incorporated '007 application, in which the introduced SunI site is underlined and the annealing nucleotides are in bold. Then the resulting PCR product was digested with MluI and SunI restriction enzymes, purified over gel and ligated to a MluI and SunI-digested pLC2001/DHFRwt plasmid that was purified over gel. The resulting plasmid was named pUBS2-Light2001/DHFRwt (FIG. 12 of the incorporated '007 application).

The PCR product of the full-length heavy chain of UBS-54 is digested with NheI and PmeI restriction enzymes and blunted with Klenow enzyme. This fragment is ligated to the plasmid pcDNAs3000/DHFRwt that is digested with BstXI restriction enzyme, blunted, dephosphorylated by SAP and purified over gel. The plasmid with the heavy chain insert is named pUBS-Heavy3000/DHFRwt. Subsequently, the PCR of the light chain is digested with MluI and PmeI restriction enzymes, blunted, purified over gel and ligated to pUBS-Heavy3000/DHFRwt that is digested with HpaI, dephosphorylated by tSAP and purified over gel. The resulting vector is named pUBS-3000/DHFRwt (FIG. 13 of the incorporated '007 application). The gene that encodes the heavy chain of UBS-54 without an intron between the variable domain and the first constant region and with a wild-type carboxy terminal constant region (2031 nucleotides) is purified over gel after digestion of pUBS2-2000/Hyg(−) with EcoRI and PmeI and treatment with Klenow enzyme and free nucleotides to blunt the EcoRI site. Subsequently, the insert is ligated to a pcDNAs3000/DHFRwt plasmid that is digested with BstXI, blunted, dephosphorylated with SAP and purified over gel. The resulting plasmid is named pUBS2-Heavy3000/DHFRwt. pUBS2-Light2001/DHFRwt is then digested with EcoRV and PmeI, and the 755 nucleotide insert containing the signal peptide linked to the variable domain of the kappa chain of UBS-54 and the constant domain of human IgG1 kappa chain without an intron sequence is purified over gel and ligated to pUBS2-Heavy3000/DHFRwt that is digested with HpaI, dephosphorylated with tSAP and purified over gel. The resulting plasmid is named pUBS2-3000/DHFRwt (FIG. 14 of the incorporated '007 application).

Plasmid pRc/CMV (Invitrogen) was digested with BstBI restriction enzymes, blunted with Klenow enzyme and subsequently digested with XmaI enzyme. The Neomycin resistance gene containing fragment was purified over agarose gel and ligated to pUBS-Light2001/DHFRwt plasmid that was digested with XmaI and PmlI restriction enzymes, followed by dephosphorylation with SAP and purified over gel to remove the DHFR cDNA. The resulting plasmid was named pUBS-Light2001/Neo(−). The fragment was also ligated to a XmaI/PmlI-digested and gel-purified pcDNA2001/DHFRwt plasmid resulting in pcDNA2001/Neo. The PCR product of the UBS −54 variable domain and the digested and purified constant domain PCR product were used in a three-point ligation with a MluI/PmeI-digested pcDNA2001/Neo. The resulting plasmid was named pUBS2-Light2001/Neo.

Example 4

Construction of CAMPATH-1H Expression Vectors

Cambridge Bioscience Ltd. (UK) generates a 396 nucleotide fragment containing a perfect Kozak sequence followed by the signal sequence and the variable region of the published CAMPATH-1H light chain (Crowe et al., 1992). This fragment contains, on the 5' end, an introduced and unique HindIII site and, on the 3' end, an introduced and unique SunI site and is cloned into an appropriate shuttle vector. This plasmid is digested with HindIII and SunI and the resulting CAMPATH-1H light chain fragment is purified over gel and ligated into a HindIII/SunI-digested and agarose gel-purified pLC2001/DHFRwt. The resulting plasmid is named pCAMPATH-Light2001/DHFRwt. Cambridge Bioscience Ltd. (UK) generated a 438 nucleotide fragment containing a perfect Kozak sequence followed by the signal sequence and the published variable region of the CAMPATH-1H heavy chain (Crowe et al., 1992), cloned into an appropriate cloning vector. This product contains a unique HindIII restriction enzyme recognition site on the 5' end and a unique NheI restriction enzyme recognition site on the 3' end. This plasmid was digested with HindIII and NheI and the resulting CAMPATH-1H heavy chain fragment was purified over gel and ligated into a purified and HindIII/NheI-digested pHC2000/Hyg(−). The resulting plasmid was named pCAMPATH-Heavy2000/Hyg(−).

Example 5

Construction of 15C5 Expression Vectors

The heavy chain of the humanized version of the monoclonal antibody 15C5 directed against human fibrin fragment D-dimer (Bulens et al., 1991; Vandamme et al., 1990) consisting of human constant domains including intron sequences, hinge region and variable regions preceded by the signal peptide from the 15C5 kappa light chain is amplified by PCR on plasmid "pCMgamma NEO Skappa Vgamma Cgamma hu" as a template using CAMH-DOWN as a down stream primer and 15C5-UP as the upstream primer. 15C5-UP has the following sequence: 5'-GA TCA CGC GTG CTA GCC ACC ATG GGT ACT CCT GCT CAG TTT CTT GGA ATC-3' (SEQ ID NO:29) corresponding to the incorporated '007 application, in which the introduced MluI and NheI restriction recognition sites are underlined and the perfect Kozak sequence is italicized. To properly introduce an adequate Kozak context, the adenine at position +4 (the adenine in the ATG start codon is +1) is replaced by a guanine, resulting in a mutation from an arginine into a glycine amino acid. To prevent primer dimerization, position +6 of the guanine is replaced by a thymine and the position +9 of the cytosine is replaced by thymine. This latter mutation leaves the threonine residue intact. The resulting PCR was digested with NheI and PmeI restriction enzymes, purified over gel and ligated to a NheI and PmeI-digested pcDNA2000/Hygro (−), that is dephosphorylated by SAP and purified over agarose gel. The resulting plasmid is named p15C5-Heavy2000/Hyg(−). The light chain of the humanized version of the monoclonal antibody 15C5 directed against human fibrin fragment D-dimer (Bulens et al., 1991; Vandamme et al., 1990) consisting of the human constant domain and variable regions preceded by a 20 amino acid signal peptide is amplified by PCR on plasmid pCMkappa DHFR13 15C5kappa hu as a template, using CAML-DOWN as a down stream primer and 15C5-UP as the upstream primer. The resulting PCR is digested with NheI and PmeI restriction enzymes, purified over gel and ligated to an NheI and PmeI-digested pcDNA2001/DHFRwt that is dephosphorylated by SAP and purified over agarose gel. The resulting plasmid is named p15C5-Light2001/DHFRwt.

Example 6

Establishment of Methotrexate Hygromycin and G418 Selection Levels

PER.C6 and PER.C6/E2A were seeded in different densities. The starting concentration of methotrexate (MTX) in these sensitivity studies ranged between 0 nM and 2500 nM. The concentration which was just lethal for both cell lines was determined; when cells were seeded in densities of 100,000 cells per well in a six-well dish, wells were still 100% confluent at 10 nM and approximately 90 to 100% confluent at 25 nM, while most cells were killed at a concentration of 50 nM and above after six days to 15 days of incubation. These results are summarized in Table 1 of the incorporated '007 application. PER.C6 cells were tested for their resistance to a combination of Hygromycin and G418 to select outgrowing stable colonies that expressed both heavy and light chains for the respective recombinant monoclonal antibodies encoded by plasmids carrying either a hygromycin or a neomycin resistance gene. When cells were grown on normal medium containing 100 μg/ml hygromycin and 250 μg/ml G418, non-transfected cells were killed and stable colonies could appear. (See, Example 7.)

CHO-dhfr cells ATCC deposit CRL9096 are seeded in different densities in their respective culture medium. The starting concentration of methotrexate in these sensitivity studies ranges from approximately 0.5 nM to 500 nM. The concentration, which is just lethal for the cell line, is determined and subsequently used directly after growth selection on hygromycin in the case of IgG heavy chain selection (hyg) and light chain selection (dhfr).

Example 7

Transfection of EPO Expression Vectors to Obtain Stable Cell Lines

Cells of cell lines PER.C6 and PER.C6/E2A were seeded in 40-tissue culture dishes (10 cm diameter) with approximately 2 to 3 million cells/dish and were kept overnight under their respective conditions (10% $CO_2$ concentration and temperature, which is 39° C. for PER.C6/E2A and 37° C. for PER.C6). The next day, transfections were all performed at 37° C. using Lipofectamine (Gibco). After replacement with fresh (DMEM) medium after four hours, PER.C6/E2A cells were transferred to 39° C. again, while PER.C6 cells were kept at 37° C. Twenty dishes of each cell line were transfected with 5 μg ScaI-digested pEPO2000/DHFRwt and twenty dishes were transfected with 5 μg ScaI-digested pEPO2000/DHFRm, all according to standard protocols. Another 13 dishes served as negative controls for methotrexate killing and transfection efficiency, which was approximately 50%. On the next day, MTX was added to the dishes in concentrations ranging between 100 and 1000 nM for DHFRwt and 50,000 and 500,000 nM for DHFRm dissolved in medium containing dialyzed FBS. Cells were incubated over a period of four to five weeks. Tissue medium (including MTX) was refreshed every two to three days. Cells were monitored daily for death, comparing between positive and negative controls. Outgrowing colonies were picked and subcultured. No positive clones could be subcultured from the transfectants that received the mutant DHFR gene, most likely due to toxic effects of the high concentrations of MTX that were applied. From the PER.C6 and PER.C6/E2A cells that were transfected with the wild-type DHFR gene, only cell lines could be established in the first passages when cells were grown on 100 nM MTX, although colonies appeared on dishes with 250 and 500 nM MTX. These clones were not viable during subculturing, and were discarded.

Example 8

Sub-Culturing of Transfected Cells

From each cell line, approximately 50 selected colonies that were resistant to the threshold MTX concentration were grown subsequently in 96-well, 24-well, and 6-well plates and T25 flasks in their respective medium plus MTX. When cells reached growth in T25 tissue culture flasks, at least one vial of each clone was frozen and stored, and was subsequently tested for human recombinant EPO production. For this, the commercial ELISA kit from R&D Systems was used (Quantikine IVD human EPO, Quantitative Colorimetric Sandwich ELISA, cat.# DEPOO). Since the different clones appeared to have different growth characteristics and growth curves, a standard for EPO production was set as follows: At day 0, cells were seeded in T25 tissue culture flasks in concentrations ranging between 0.5 to 1.5 million per flask. At day 4, supernatant was taken and used in the EPO ELISA. From this, the production level was set as ELISA units per million seeded cells per day. (U/1E6/day) A number of these clones are given in Table 2 of the incorporated '007 patent application.

The following selection of good producer clones was based on high expression, culturing behavior and viability. To allow checks for long-term viability, suspension growth in roller bottles and bioreactor during extended time periods, more vials of the best producer clones were frozen, and the following best producers of each cell line were selected for further investigations P8, P9, E17 and E55 in which "P" stands for PER.C6 and "E" stands for PER.C6/E2A. These clones are subcultured and subjected to increasing doses of methotrexate in a time span of two months. The concentration starts at the threshold concentration and increases to approximately 0.2 mM. During these two months, EPO ELISA experiments are performed on a regular basis to detect an increase in EPO production. At the highest methotrexate concentration, the best stable producer is selected and compared to the amounts from the best CHO clone and used for cell banking (RL). From every other clone, five vials are frozen. The number of amplified EPO cDNA copies is detected by Southern blotting.

Example 9

EPO Production in Bioreactors

The best performing EPO producing transfected stable cell line of PER.C6, P9, was brought into suspension and scaled up to 1 to 2 liter fermentors. To get P9 into suspension, attached cells were washed with PBS and subsequently incubated with JRH ExCell 525 medium for PER.C6 (JRH Biosciences), after which the cells loosen from the flask and form the suspension culture. Cells were kept at two concentrations of MTX: 0 nM and 100 nM. General production levels of EPO that were reached at these concentrations (in roller bottles) were respectively 1500 and 5700 units per million seeded cells per day. Although the lower yields in the absence of MTX can be explained by removal of the integrated DNA, it seems as if there is a shut-down effect of the integrated DNA since cells that are kept at lower concentrations of MTX for longer periods of time are able to reach their former yields when they are transferred to 100 nM MTX concentrations again. (See, Example 11.)

Suspension P9 cells were grown normally with 100 nM MTX and used for inoculation of bioreactors. Two bioreactor settings were tested: perfusion and repeated batch cultures.

A. Perfusion in a 2 Liter Bioreactor.

Cells were seeded at a concentration of $0.5 \times 10^6$ cells per ml and perfusion was started at day 3 after cells reached a density of approximately $2.3 \times 10^6$ cells per ml. The perfusion rate was 1 volume per 24 hours with a bleed of approximately 250 ml per 24 hours. In this setting, P9 cells stayed at a constant density of approximately $5 \times 10^6$ cells per ml and a viability of almost 95% for over a month. The EPO concentration was determined on a regular basis and is shown in FIG. 15 (of the incorporated '007 application). In the 2 liter perfused bioreactor the P9 cells were able to maintain a production level of approximately 6000 ELISA units per ml. With a perfusion rate of one working volume per day (1.5 to 1.6 liter), this means that in this 2 liter setting, the P9 cells produced approximately $1 \times 10^7$ units per day per 2 liter bioreactor in the absence of MTX.

B. Repeated Batch in a 2 Liter Bioreactor.

P9 suspension cells that were grown on roller bottles were used to inoculate a 2 liter bioreactor in the absence of MTX and were left to grow until a density of approximately 1.5 million cells per ml, after which a third of the population was removed (+/−1 liter per 2 to 3 days) and the remaining culture was diluted with fresh medium to reach again a density of 0.5 million cells per ml. This procedure was repeated for three weeks and the working volume was kept at 1.6 liter. EPO concentrations in the removed medium were determined and shown in FIG. 16 of the incorporated '007 application. The average concentration was approximately 3000 ELISA units per ml. With an average period of two days after which the population was diluted, this means that, in this 2 liter setting, the P9 cells produced approximately $1.5 \times 10^6$ units per day in the absence of MTX.

C. Repeated Batch in a 1 Liter Bioreactor with Different Concentrations of Dissolved Oxygen, Temperatures and pH Settings.

Fresh P9 suspension cells were grown in the presence of 100 nM MTX in roller bottles and used for inoculation of 4×1 liter bioreactors to a density of 0.3 million cells per ml in JRH ExCell 525 medium. EPO yields were determined after 3, 5 and 7 days. The first settings that were tested were: 0.5%, 10%, 150% and as a positive control 50% Dissolved Oxygen (% DO). 50% DO is the condition in which PER.C6 and P9 cells are normally kept. In another run, P9 cells were inoculated and tested for EPO production at different temperatures (32° C., 34° C., 37° C. and 39° C.) in which 37° C. is the normal setting for PER.C6 and P9, and in the third run, fresh P9 cells were inoculated and tested for EPO production at different pH settings (pH 6.5, pH 6.8, pH 7.0 and pH 7.3). PER.C6 cells are normally kept at pH 7.3. An overview of the EPO yields (three days after seeding) is shown in FIG. 17 of the incorporated '007 application. Apparently, EPO concentrations increase when the temperature is rising from 32 to 39° C. as was also seen with PER.C6/E2A cells grown at 39° C. (Table 4) (of the incorporated '007 application), and 50% DO is optimal for P9 in the range that was tested here. At pH 6.5, cells cannot survive since the viability in this bioreactor dropped beneath 80% after seven days. EPO samples produced in these settings are checked for glycosylation and charge in 2D electrophoresis. (See, also Example 17.)

Example 10

Amplification of the DHFR Gene

A number of cell lines described in Example 8 were used in an amplification experiment to determine the possibility of increasing the number of DHFR genes by increasing the concentration of MTX in a time span of more than two months. The concentration started at the threshold concentration (100 nM) and increased to 1800 nM with in-between steps of 200 nM, 400 nM, 800 nM and 1200 nM. During this period, EPO ELISA experiments were performed on a regular basis to detect the units per million seeded cells per day (FIG. 18 of the incorporated '007 application). At the highest MTX concentration (1800 nM), some vials were frozen. Cell pellets were obtained and DNA was extracted and subsequently digested with BglII, since this enzyme cuts around the wild-type DHFR gene in pEPO200/DHFRwt (FIG. 5 of the incorporated '007 application), so a distinct DHFR band of that size would be distinguishable from the endogenous DHFR bands in a Southern blot. This DNA was run and blotted and the blot was hybridized with a radioactive DHFR probe and subsequently with an adenovirus E1 probe as a background control (FIG. 19 of the incorporated '007 application). The intensities of the hybridizing bands were measured in a phosphorimager and corrected for background levels. These results are shown in Table 3 of the incorporated '007 application. Apparently, it is possible to obtain amplification of the DHFR gene in PER.C6 cells, albeit in this case only with the endogenous DHFR and not with the integrated vector.

Example 11

Stability of EPO Expression in Stable Cell Lines

A number of cell lines mentioned in Example 8 were subject to long term culturing in the presence and absence of MTX. EPO concentrations were measured regularly in which 1.0 to $1.5 \times 10^6$ cells per T25 flask were seeded and left for four days to calculate the production levels of EPO per million seeded cells per day. The results are shown in FIG. 20 of the incorporated '007 application. From this, it is concluded that there is a relatively stable expression of EPO in P9 cells when cells are cultured in the presence of MTX and that there is a decrease in EPO production in the absence of MTX. However, when P9 cells were placed on 100 nM MTX again after being cultured for a longer period of time without MTX, the expressed EPO reached its original level (+/−3000 ELISA units per million seeded cells per day), suggesting that the integrated plasmids are shut off but are stably integrated and can be switched back on again. It seems as if there are differences between the cell lines P8 and P9 because the production level of P8 in the presence of MTX is decreasing in time over a high number of passages (FIG. 20A of the incorporated '007 application), while P9 production is stable for at least 62 passages (FIG. 20B of the incorporated '007 application).

Example 12

Transient Expression of Recombinant EPO on Attached and Suspension Cells after Plasmid DNA Transfections pEPO2000/DHFRwt, pEPO2000/DHFRm and pAdApt.EPO plasmids from Example 2 are purified from *E. coli* over columns, and are transfected using lipofectamine, electroporation, PEI or other methods. PER.C6 or PER.C6/E2A cells are counted and seeded in DMEM plus serum or JRH ExCell 525 medium or the appropriate medium for transfection in suspension. Transfection is performed at 37° C. up to 16 hours, depending on the transfection method used, according to procedures known by a person skilled in the art. Subsequently, the cells are placed at different temperatures and the medium is replaced by fresh medium with or without serum. In the case when it is necessary to obtain medium that completely lacks serum components, the fresh medium lacking serum is removed again after 3 hours and replaced again by medium lacking serum components. For determination of recombinant EPO production, samples are taken at different time points. Yields of recombinant protein are determined using an ELISA kit (R&D Systems) in which 1 Unit equals approximately 10 ng of recombinant CHO-produced EPO protein (100,000 Units/mg). The cells used in these experiments grow at different rates, due to their origin, characteristics and temperature. Therefore, the amount of recombinant EPO produced is generally calculated in ELISA units/$10^6$ seeded cells/day, taking into account that the antisera used in the ELISA kit do not discriminate between non- and highly glycosylated recombinant EPO. Generally, samples for these calculations are taken at day 4 after replacing the medium upon transfection.

PER.C6/E2A cells, transfected at 37° C. using lipofectamine and subsequently grown at 39° C. in the presence of serum, typically produced 3100 units/$10^6$ cells/day. In the absence of serum components without any refreshment of medium lacking serum, these lipofectamine-transfected cells typically produced 2600 units/$10^6$ cells/day. PER.C6 cells, transfected at 37° C. using lipofectamine and subsequently grown at 37° C. in the presence of serum, typically produced 750 units/$10^6$ cells/day and, in the absence of serum, 590 units/$10^6$ cells/day. For comparison, the same expression plasmids pEPO2000/DHFRwt and pEPO2000/DHFRm were also applied to transfect CHO cells (ECACC deposit no. 85050302) using lipofectamine, PEI, calcium phosphate procedures and other methods. When CHO cells were transfected using lipofectamine and subsequently cultured in Hams F12 medium in the presence of serum, a yield of 190 units/$10^6$ cells/day was obtained. In the absence of serum, 90 units/$10^6$ cells/day were produced, although higher yields can be obtained when transfections are being performed in DMEM.

Different plates containing attached PER.C6/E2A cells were also transfected at 37° C. with pEPO2000/DHFRwt plasmid and subsequently placed at 32° C., 34° C., 37° C. or 39° C. to determine the influence of temperature on recombinant EPO production. A temperature-dependent production level was observed ranging from 250 to 610 units/$10^6$ seeded cells/day, calculated from a day 4 sample, suggesting that the difference between production levels observed in PER.C6 and PER.C6/E2A is partly due to incubation temperatures (see, also FIG. 17 of the incorporated '007 application). Since PER.C6/E2A grows well at 37° C., further studies were performed at 37° C.

Different plates containing attached PER.C6 and PER.C6/E2A cells were transfected with pEPO2000/DHFRwt, pEPO2000/DHFRm and pAdApt.EPO using lipofectamine. Four hours after transfection, the DMEM was replaced with either DMEM plus serum or JRH medium lacking serum and EPO was allowed to accumulate in the supernatant for several days to determine the concentrations that are produced in the different mediums. PER.C6 cells were incubated at 37° C., while PER.C6/E2A cells were kept at 39° C. Data from the different plasmids were averaged since they contain a similar expression cassette. Calculated from a day 6 sample, the following data were obtained: PER.C6 grown in DMEM produced 400 units/$10^6$ seeded cells/day, and when they were kept in JRH medium, they produced 300 units/$10^6$ seeded cells/day. PER.C6/E2A grown in DMEM produced 1800 units/$10^6$ seeded cells/day, and when they were kept in JRH, they produced 1100 units/$10^6$ seeded cells/day. Again, a clear difference was observed in production levels between PER.C6 and PER.C6/E2A, although this might partly be due to temperature differences. There was, however, a significant difference with PER.C6/E2A cells between the concentration in DMEM vs. the concentration in JRH medium, although this effect was almost completely lost in PER.C6 cells.

EPO expression data obtained in this system are summarized in Table 4 (of the incorporated '007 application). PER.C6 and derivatives thereof can be used for scaling up the DNA transfections system. According to Wurm and Bernard (1999), transfections on suspension cells can be performed at 1 to 10 liter set-ups in which yields of 1 to 10 mg/l (0.1 to 1 pg/cell/day) of recombinant protein have been obtained using electroporation. A need exists for a system in which this can be well controlled and yields might be higher, especially for screening of large numbers of proteins and toxic proteins that cannot be produced in a stable setting. With the lipofectamine transfections on the best PER.C6 cells in the absence of serum, we reached 590 units/million cells/day (+/−5.9 pg/cell/day when 1 ELISA unit is approximately 10 ng EPO), while PER.C6/E2A reached 31 pg/cell/day (in the presence of serum). The medium used for suspension cultures of PER.C6 and PER.C6/E2A (JRH ExCell 525) does not support efficient transient DNA transfections using components like PEI. Therefore, the medium is adjusted to enable production of recombinant EPO after transfection of pEPO2000/DHFRwt and pEPO2000/DHFRm containing a recombinant human EPO cDNA, and pcDNA2000/DHFRwt containing other cDNAs encoding recombinant proteins.

One to 10 liter suspension cultures of PER.C6 and PER.C6/E2A growing in adjusted medium to support transient DNA transfections using purified plasmid DNA are used for electroporation or other methods, performing transfection with the same expression plasmids. After several hours, the transfection medium is removed and replaced by fresh medium without serum. The recombinant protein is allowed to accumulate in the supernatant for several days, after which the supernatant is harvested and all the cells are removed. The supernatant is used for down stream processing to purify the recombinant protein.

Example 13

Generation of AdApt.EPO Recombinant Adenoviruses pAdApt.EPO was co-transfected with the pWE/Ad.AflII-rITR.tetO-E4, pWE/Ad.AflII-rITR.DE2A, and pWE/Ad.AflII-rITR.DE2A.tetO-E4 cosmids in the appropriate cell lines using procedures known to persons skilled in the art. Subsequently, cells were left at their appropriate temperatures for several days until full cytopathic effect ("CPE") was observed. Then cells were applied to several freeze/thaw steps to free all viruses from the cells, after which the cell debris was spun down. For IG.Ad5/AdApt.EPO.dE2A, the supernatant was used to infect cells, followed by an agarose overlay for plaque purification using several dilutions. After a number of days, when single plaques were clearly visible in the highest dilutions, nine plaques and one negative control (picked cells between clear plaques, so most likely not containing virus) were picked and checked for EPO production on A549 cells. All plaque picked viruses were positive and the negative control did not produce recombinant EPO. One positive producer was used to infect the appropriate cells and to propagate virus starting from a T-25 flask to a roller bottle setting. Supernatants from the roller bottles were used to purify the virus, after which the number of virus particles (vps) was determined and compared to the number of infectious units (IUs) using procedures known to persons skilled in the art. Then, the vp/IU ratio was determined.

Example 14

Infection of Attached and Suspension PER.C6 Cells with IG.Ad5/AdApt.EPO.dE2A

Purified viruses from Example 13 were used for transient expression of recombinant EPO in PER.C6 cells and derivatives thereof. IG.Ad5/AdApt.EPO.dE2A virus was used to infect PER.C6 cells, while IG.Ad5/AdApt.EPO.tetOE4 and IG.Ad5/AdApt.EPO.dE2A.tetOE4 viruses can be used to infect PER.C6/E2A cells to lower the possibility of replication and, moreover, to prevent inhibition of recombinant protein production due to replication processes. Infections were performed on attached cells as well as on suspension cells in their appropriate medium using ranges of multiplicities of infection (moi's): 20, 200, 2000, 20000 vp/cell. Infections were performed for four hours in different settings ranging from six-well plates to roller bottles, after which the virus containing supernatant was removed. The cells were washed with PBS or directly refreshed with new medium. Then, cells were allowed to produce recombinant EPO for several days, during which samples were taken and EPO yields were determined. Also, the number of viable cells compared to dead cells was checked. The amount of EPO that was produced was again calculated as ELISA unit seeded cells/day, because the different cell lines have different growth characteristics due to their passage number and environmental circumstances such as temperature and selective pressures. Suspension growing PER.C6 cells were seeded in 250 ml JRH ExCell 525 medium in roller bottles (1 million cells per ml) and subsequently infected with purified IG.Ad5/AdApt.EPO.dE2A virus with a moi of 200 vp/cell. The estimation used for vp determination was high (vp/tU ratio of this batch is 330, which indicates an moi of 0.61 IUs/cell). Thus, not all cells were hit by an infectious virus. A typical production of recombinant EPO in this setting from a day 6 sample was 190 units/$10^6$ seeded cells/day, while in a setting in which 50% of the medium including viable and dead cells was replaced by fresh medium, approximately 240 units/$10^6$ cells/day were obtained. The refreshment did not influence the viability of the viable cells, but the removed recombinant protein could be added to the amount that was obtained at the end of the experiment, albeit present in a larger volume. An identical experiment was performed with the exception that cells were infected with a moi of 20 vp/cell, resembling approximately 0.06 Infectious Units/cell. Without refreshment, a yield of 70 ELISA units/$10^6$ cells/day was obtained, while in the experiment in which 50% of the medium was refreshed at day 3, a typical amount of 80 units/$10^6$ cells/day was measured. This indicates that there is a dose response effect when an increasing number of infectious units are used for infection of PER.C6 cells.

Furthermore, PER.C6 cells growing in DMEM were seeded in six-well plates and left overnight in 2 ml DMEM with serum to attach. The next day, cells were infected with another batch of IG.Ad5/AdApt.EPO.dE2A virus (vp/IU ratio 560) with a moi of 200 vp/cells (0.35 Infectious Units/cell). After four hours, the virus containing medium was removed and replaced by fresh medium including serum, and cells were left to produce recombinant EPO for more than two weeks with replacement of the medium with fresh medium every day. The yield of recombinant EPO production calculated from a day 4 sample was 60 units/$10^6$ cells/day.

Expression data obtained in this system have been summarized in Table 5 (of the incorporated '007 application).

Due to the fact that a tTA-tetO regulated expression of the Early region 4 of adenovirus (E4) impairs the replication capacity of the recombinant virus in the absence of active E4, it is also possible to use the possible protein production potential of the PER.C6/E2A as well as its parental cell line PER.C6 to produce recombinant proteins in a setting in which a recombinant adenovirus is carrying the human EPO cDNA as the transgene and in which the E4 gene is under the control of a tet operon. Then, very low levels of E4 mRNA are being produced, resulting in very low but detectable levels of recombinant and replicating virus in the cell line PER.C6/E2A and no detectable levels of this virus in PER.C6 cells. To produce recombinant EPO in this way, the two viruses IG.Ad5/AdApt.EPO.tetOE4 and IG.Ad5/AdApt.EPO.dE2A.tetOE4 are used to infect PER.C6 cells and derivatives thereof. Attached and suspension cells are infected with different moi's of the purified adenoviruses in small settings (six-well plates and T25 flasks) and large settings (roller bottles and fermentors). Samples are taken at different time points and EPO levels are determined.

Since viruses that are deleted in E1 and E2A in the viral backbone can be complemented in PER.C6/E2A cells but not in the original PER.C6 cells, settings are used in which a mixture of both cell lines is cultured in the presence of IG.Ad5/AdApt.EPO.dE2A virus. The virus will replicate in PER.C6/E2A, followed by lysis of the infected cells and a subsequent infection of PER.C6 or PER.C6/E2A cells. In contrast, in PER.C6 cells, the virus will not replicate and the cells will not lyse due to viral particle production, but will produce recombinant EPO that will be secreted in the supernatant. A steady state culture/replication/EPO production system is set up in which fresh medium and fresh PER.C6 and PER.C6/E2A cells are added at a constant flow, while used medium, dead cells and debris are removed. Together with this, recombinant EPO is taken from the system and used for purification in a down stream processing procedure in which virus particles are removed.

Example 15

Purification and Analysis of Recombinant EPO

Large batches of growing cells are produced in bioreactors; the secreted recombinant human EPO protein is purified according to procedures known by one of skill in the art. The purified recombinant human EPO protein from PER.C6 and PER.C6/E2A stable clones or transfectants is checked for glycosylation and folding by comparison with commercially available EPO and EPO purified from human origin (urine) using methods known to one of skill in the art (see, Examples 16 and 17). Purified and glycosylated EPO proteins from PER.C6 and PER.C6/E2A are tested for biological activity in in vitro experiments and in mouse spleens as described (Krystal (1983) and in vitro assays (see, Example 18).

Example 16

Activity of Beta-galactoside Alpha 2,6-sialyltransferase in PER.C6

It is known that CHO cells do not contain a gene for beta-galactoside alpha 2,6-sialyltransferase, resulting in the absence of alpha 2,6-linked sialic acids at the terminal ends of—and O-linked oligosaccharides of endogenous and recombinant glycoproteins produced on these CHO cells. Since the alpha 2,3-sialyltransferase gene is present in CHO cells, proteins that are produced on these cells are typically from the 2,3 linkage type. EPO that was purified from human urine does, however, contain both alpha 2,3- and alpha 2,6-linked sialic acids. To determine whether PER.C6 cells, being a human cell line, are able to produce recombinant EPO containing both alpha 2,3- and alpha 2,6-linkages, a direct neuraminidase assay was performed on recombinant EPO produced on PER.C6 cells after transfection with EPO expression vectors. As a control, commercially available Eprex samples were used, which were derived from CHO cells and which should only contain sialic acid linkages of the alpha 2,3 type. The neuraminidases that were used were from Newcastle Disease Virus (NDV) that specifically cleaves alpha 2,3-linked neuraminic acids (sialic acids) from—and O-linked glycans, and from Vibrocholerae (VC) that non-specifically cleaves all terminal—or O-linked sialic acids (alpha 2,3, alpha 2,6 and alpha 2,8 linkages). Both neuraminidases were from Boehringer and were incubated with the samples according to guidelines provided by the manufacturer. Results are shown in FIG. 21A (of the incorporated '007 application). In lanes 2 and 3 (treatment with NDV neuraminidase), a slight shift is observed as compared to lane 1 (non-treated PER.C6 EPO). When this EPO sample was incubated with VC derived neuraminidase, an even faster migrating band is observed as compared to NDV treated samples. However, with the commercially available Eprex, only a shift was observed when NDV derived neuraminidase was applied (lanes 6 and 7 compared to the non-treated sample in lane 5) and not when VC neuraminidase was used (lane 8).

To definitely establish that no sialic acids of the alpha 2,6 linkage type are present on CHO cells, but that they do exist in proteins present on the cell surface of PER.C6 cells, the following experiment was performed: CHO cells were released from the solid support using trypsin-EDTA, while for PER.C6, suspension cells were used. Both suspensions were washed once with Mem-5% FBS and incubated in this medium for one hour at 37° C. After washing with PBS, the cells were resuspended to approximately $10^6$ cells/ml in binding medium (Tris-buffered saline, pH 7.5, 0.5% BSA, and 1 mM each of $MgCl_2$, $MnCl_2$ and $CaCl_2$). Aliquots of the cells were incubated for 1 hour at room temperature with DIG-labeled lectins, *Sambucus nigra* agglutinin ("SNA") and *Maackia amurensis* agglutinin ("MAA"), which specifically bind to sialic acid linkages of the alpha 2,6 Gal and alpha 2,3 Gal types, respectively. Control cells were incubated without lectins. After one hour, both lectin-treated and control cells were washed with PBS and then incubated for one hour at room temperature with FITC-labeled anti-DIG antibody (Boehringer-Mannheim). Subsequently, the cells were washed with PBS and analyzed for fluorescence intensity on a FACsort apparatus (Becton Dickinson). The FACS analysis is shown in FIG. 21B (of the incorporated '007 application). When the SNA lectin is incubated with CHO cells, no shift is seen as compared to non-treated cells, while when this lectin is incubated with PER.C6 cells, a clear shift (dark fields) is observed as compared to non-treated cells (open fields). When both cell lines are incubated with the MAA lectin, both cell lines give a clear shift as compared to non-treated cells.

From these EPO digestions and FACS results, it is concluded that there is a beta-galactoside alpha 2,6 sialyltransferase activity present in human PER.C6 cells which is absent in CHO cells.

Example 17

Determination of Sialic Acid Content in PER.C6 Produced EPO

The terminal neuraminic acids (or sialic acids) that are present on the—and O-linked glycans of EPO protect the protein from clearance from the bloodstream by enzymes in the liver. Moreover, since these sialic acids are negatively charged, one can distinguish between different EPO forms depending on their charge or specific pI. Therefore, EPO produced on PER.C6 and CHO cells was used in two-dimensional electrophoresis in which the first dimension separates the protein on charge (pH range 3-10) and the second dimension separates the proteins further on molecular weight. Subsequently, the proteins were blotted and detected in a western blot with an anti-EPO antibody.

It is also possible to detect the separated EPO protein by staining the gel using Coomassie blue or silver staining methods, subsequently removing different spots from the gel and determining the specific glycan composition of the different—or O-linked glycosylations that are present on the protein by mass spectrometry.

In FIG. 22A of the incorporated '007 application, a number of EPO samples are shown that were derived from P9 supernatants. P9 is the PER.C6 cell line that stably expresses recombinant human EPO (see, Example 8). These samples were compared to commercially available Eprex, which contains only EPO forms harboring approximately 9 to 14 sialic acids. Eprex should, therefore, be negatively charged and be focusing towards the pH3 side of the gel. FIG. 22B (of the incorporated '007 application) shows a comparison between EPO derived from P9 in an attached setting in which the cells were cultured on DMEM medium and EPO derived from CHO cells that were transiently transfected with the pEPO2000/DHFRwt vector. Apparently, the lower forms of EPO cannot be detected in the CHO samples, whereas all forms can be seen in the P9 sample. The sialic acid content is given by numbering the bands that were separated in the first dimension from 1 to 14. It is not possible to determine the percentage of each form of EPO molecules present in the mixtures because the western blot was performed using ECL, and because it is unknown whether glycosylation of the EPO molecule or transfer of the EPO molecule to the nitrocellulose inhibits recognition of the EPO molecule by the antibody. However, it is possible to determine the presence of the separate forms of sialic acid containing EPO molecules. It can be concluded that PER.C6 is able to produce the entire range of 14 sialic acid containing isoforms of recombinant human EPO.

Example 18

In Vitro Functionality of PER.C6 Produced EPO

The function of recombinant EPO in vivo is determined by its half-life in the bloodstream. Removal of EPO takes place by liver enzymes that bind to galactose residues in the glycans that are not protected by sialic acids and by removal through the kidney. Whether this filtering by the kidney is due to misfolding or due to under- or mis-glycosylation is unknown. Furthermore, EPO molecules that reach their targets in the bone marrow and bind to the EPO receptor on progenitor cells are also removed from circulation. Binding to the EPO receptor and down stream signaling depends heavily on a proper glycosylation status of the EPO molecule. Sialic acids can, to some extent, inhibit binding of EPO to the EPO receptor, resulting in a lower effectiveness of the protein. However, since the sialic acids prevent EPO from removal, these sugars are essential for its function to protect the protein on its travel to the EPO receptor. When sialic acids are removed from EPO in vitro, a better binding to the receptor occurs, resulting in a stronger down stream signaling. This means that the functionalities in vivo and in vitro are significantly different, although a proper EPO receptor binding property can be checked in vitro despite the possibility of an under-sialylation causing a short half-life in vivo (Takeuchi et al., 1989).

Several in vitro assays for EPO functionality have been described of which the stimulation of the IL3, GM-CSF and EPO-dependent human cell line TF-1 is most commonly used. Hereby, one can determine the number of in vitro units per mg (Kitamura et al., 1989; Hammerling et al., 1996). Other in vitro assays are the formation of red colonies under an agarose layer of bone marrow cells that were stimulated to differentiate by EPO, the incorporation of 59Fe into heme in cultured mouse bone marrow cells (Krystal et al., 1981 and 1983; Takeuchi et al., 1989), in rat bone marrow cells (Goldwasser et al., 1975) and the Radio Immuno Assay (RIA) in which the recognition of EPO for antisera is determined.

EPO produced on PER.C6/E2A cells was used to stimulate TF-1 cells as follows: Cells were seeded in 96-well plates with a density of around 10,000 cells per well in medium lacking IL3 or GM-CSF, which are the growth factors that can stimulate indefinite growth of these cells in culture. Subsequently, medium is added, resulting in final concentrations of 0.0001, 0.001, 0.01, 0.1, 1 and 10 units per ml. These units were determined by ELISA, while the units of the positive control Eprex were known (4000 units per ml) and were diluted to the same concentration. Cells were incubated with these EPO samples for four days, after which an MTS assay (Promega) was performed to check for viable cells by fluorescence measurement at 490 nm (fluorescence is detectable after transfer of MTS into formazan). FIG. 23 of the incorporated '007 application shows the activity of two samples derived from PER.C6/E2A cells that were transfected with an EPO expression vector and subsequently incubated at 37° C. and 39° C. for four days. The results suggest that samples obtained at 39° C. are more active than samples obtained at 37° C., which might indicate that the sialic acid content is suboptimal at higher temperatures. It is hereby shown that PER.C6 produced EPO can stimulate TF-1 cells in an in vitro assay, strongly suggesting that the EPO that is produced on this human cell line can interact with the EPO receptor and stimulate differentiation.

Example 19

Production of Recombinant Murine, Humanized and Human Monoclonal Antibodies in PER.C6 and PER.C6/E2A A. Transient DNA Transfections cDNAs encoding heavy and light chains of murine, humanized and human monoclonal antibodies (mAbs) are cloned in two different systems: one in which the heavy and light chains are integrated into one single plasmid (a modified pcDNA2000/DHFRwt plasmid) and the other in which heavy and light chain cDNAs are cloned separately into two different plasmids (see, Examples 1, 3, 4 and 5). These plasmids can carry the same selection marker (like DHFR) or they carry their own selection marker (one that contains the DHFR gene and one that contains, for instance, the neo-resistance marker). For transient expression systems, it does not matter what selection markers are present in the backbone of the vector since no subsequent selection is being performed. In the common and regular transfection methods used in the art, equal amounts of plasmids are transfected. A disadvantage of integrating both heavy and light chains on one single plasmid is that the promoters that are driving the expression of both cDNAs might influence each other, resulting in non-equal expression levels of both subunits, although the number of cDNA copies of each gene is exactly the same.

Plasmids containing the cDNAs of the heavy and light chain of a murine and a humanized monoclonal antibody are transfected and, after several days, the concentration of correctly folded antibody is determined using methods known to persons skilled in the art. Conditions such as temperature and used medium are checked for both PER.C6 and PER.C6/E2A cells. Functionality of the produced recombinant antibody is controlled by determination of affinity for the specified antigen.

B. Transient Viral Infections cDNAs encoding a heavy and a light chain are cloned in two different systems: one in which the heavy and light chains are integrated into one single adapter plasmid (a modified pAdApt.pac) and the other in which heavy and light chain cDNAs are cloned separately into two different adapters (each separately in pAdApt.pac). In the first system, viruses are propagated that carry an E1 deletion (dE1) together with an E2A deletion (dE2A) or both deletions in the context of a tetOE4 insertion in the adenoviral backbone. In the second system, the heavy and light chains are cloned separately in pAdApt.pac and separately propagated to viruses with the same adenoviral backbone. These viruses are used to perform single or co-infections on attached and suspension growing PER.C6 and PER.C6/E2A cells. After several days, samples are taken to determine the concentration of full length recombinant antibodies, after which the functionality of these antibodies is determined using the specified antigen in affinity studies.

C. Stable Production and Amplification of the Integrated Plasmid.

Expression plasmids carrying the heavy and light chain together and plasmids carrying the heavy and light chain separately are used to transfect attached PER.C6 and PER.C6/E2A and CHO-dhfr cells. Subsequently, cells are exposed to MTX and/or hygromycin and neomycin to select for integration of the different plasmids. Moreover, a double selection with G418 and hygromycin is performed to select for integration of plasmids that carry the neomycin and hygromycin resistance gene. Expression of functional full length monoclonal antibodies is determined and best expressing clones are used for subsequent studies including stability of integration, copy number detection, determination of levels of both subunits and ability to amplify upon increase of MTX concentration after the best performing cell lines are used for mAb production in larger settings such as perfused and (fed-) batch bioreactors, after which optimization of quantity and quality of the mAbs is executed.

Example 20

Transfection of mAb Expression Vectors to Obtain Stable Cell Lines

PER.C6 cells were seeded in DMEM plus 10% FBS in 47-tissue culture dishes (10 cm diameter) with approximately $2.5 \times 10^6$ cells per dish and were kept overnight under their normal culture conditions (10% $CO_2$ concentration and 37° C.). The next day, co-transfections were performed in 39 dishes at 37° C. using Lipofectamine in standard protocols with 1 μg MunI-digested and purified pUBS-Heavy2000/Hyg(−) and 1 μg SeaI-digested and purified pUBS-Light2001/Neo (see, Example 3) per dish, while two dishes were co-transfected as controls with 1 μg MunI-digested and purified pcDNA2000/Hyg(−) and 1 μg SeaI-digested and purified pcDNA2001/Neo. As a control for transfection efficiency, four dishes were transfected with a LacZ control vector, while two dishes were not transfected and served as negative controls.

After hours, cells were washed twice with DMEM and re-fed with fresh medium without selection. The next day, medium was replaced by fresh medium containing different selection reagents: 33 dishes of the heavy and light chain co-transfectants, two dishes that were transfected with the empty vectors and the two negative controls (no transfection) were incubated only with 50 μg per ml hygromycin, two dishes of the heavy and light chain co-transfectants and two dishes of the transfection efficiency dishes (LacZ vector) were incubated only with 500 μg per ml G418, while two transfection efficiency dishes were not treated with selection medium but used for transfection efficiency that was around 40%. Two dishes were incubated with a combination of 50 μg per ml hygromycin and 250 μg per ml G418 and two dishes were incubated with 25 μg per ml hygromycin and 500 μg per ml G418.

Since cells were overgrowing when they were only incubated with hygromycin alone, it was decided that a combination of hygromycin and G418 selection would immediately kill the cells that integrated only one type of the two vectors that were transfected. Seven days after seeding, all co-transfectants were further incubated with a combination of 100 μg per ml hygromycin and 500 μg per ml G418. Cells were refreshed two or three days with medium containing the same concentrations of selecting agents. Fourteen days after seeding, the concentrations were adjusted to 250 μg per ml G418 and 50 μg per ml hygromycin. Twenty-two days after seeding, a large number of colonies had grown to an extent in which it was possible to select, pick and subculture. Approximately 300 separate colonies were selected and picked from the 10 cm dishes and subsequently grown via 96 wells and/or 24 wells via six-well plates to T25 flasks. In this stage, cells are frozen (four vials per subcultured colony) and production levels of recombinant UBS-54 mAb are determined in the supernatant using the ELISA described in Example 26.

CHO-dhfr cells are seeded in DMEM plus 10% FBS including hypoxanthine and thymidine in tissue culture dishes (10 cm diameter) with approximately 1 million cells per dish and are kept overnight under normal conditions and used for a co-transfection the next day with pUBS-Heavy2000/Hyg(−) and pUBS-Light2001/DHFRwt under standard protocols using Lipofectamine. Medium is replaced with fresh medium after a few hours and split to different densities to allow the cells to adjust to the selection medium when stable integration is taking place without a possible outgrowth of non-transfected cells. Colonies are first selected on hygromycin resistance and, subsequently, MTX is added to select for double integrations of the 2 plasmids in these subcultured cell lines.

Transfections as described for pUBS-Heavy2000/Hyg(−) and pUBS-Light2001/Neo are performed with pUBS2-Heavy2000/Hyg(−) and pUBS2-Light2001/Neo in PER.C6 and PER.C6/E2A and selection is performed with either subsequent incubation with hygromycin followed by G418 or as described above with a combination of both selection reagents. CHO-dhfr cells are transfected with pUBS2-Heavy2000/Hyg(−) and pUBS2-Light2001/DHFRwt as described herein and selection is performed in a sequential way in which cells are first selected with hygromycin, after which an integration of the light chain vector is controlled by selection on MTX.

Furthermore, PER.C6 and PER.C6/E2A cells are also used for transfections with pUBS-3000/Hyg(−) and pUBS2-3000/Hyg(−), while CHO-dhfr cells are transfected with pUBS-3000/DHFRwt and pUBS2-3000/DHFRwt, after which a selection and further amplification of the integrated plasmids are performed by increasing the MTX concentration. In the case of the pcDNAs3000 plasmids, an equal number of mRNAs of both the heavy and light chain is expected, while in the case of two separate vectors, it is unclear whether a correct equilibrium is achieved between the two subunits of the immunoglobulin.

Transfections are also being performed on PER.C6, PER.C6/E2A and CHO-dhfr with expression vectors described in Examples 4 and 5 to obtain stable cell lines that express the humanized IgG1 mAb CAMPATH-1H and the humanized IgG1 mAb 15C5 respectively.

Example 21

Sub-Culturing of Transfected Cells

From PER.C6 cells transfected with pUBS-Heavy2000/Hyg (−) and PUBS-Light2001/Neo, approximately 300 colonies that were growing in medium containing Hygromycin and G418 were generally grown subsequently in 96-well, 24-well and 6-well plates in their respective medium plus their respective selecting agents. Cells that were able to grow in 24-well plates were checked for mAb production by using the ELISA described in Example 26. If cells scored positively, at least one vial of each clone was frozen and stored, and cells were subsequently tested and subcultured. The selection of a good producer clone is based on high expression, culturing behavior and viability. To allow checks for long term viability, amplification of the integrated plasmids and suspension growth during extended time periods, best producer clones are frozen, of which a number of the best producers of each cell line are selected for further work. Similar experiments are being performed on CHO-dhfr cells transfected with different plasmids and PER.C6 and PER.C6/E2A cells that were transfected with other combinations of heavy and light chains and other combinations of selection markers.

Example 22 mAb Production in Bioreactors

The best UBS-54 producing transfected cell line of PER.C6 is brought into suspension by washing the cells in PBS and then culturing the cells in JRH ExCell 525 medium, first in small culture flasks and subsequently in roller bottles, and scaled up to 1 to 2 liter fermentors. Cells are kept on hygromycin and G418 selection until it is proven that integration of the vectors is stable over longer periods of time. This is done when cells are still in their attached phase or when cells are in suspension.

Suspension growing mAb producing PER.C6 cells are generally cultured with hygromycin and G418 and used for inoculation of bioreactors from roller bottles. Production yields, functionality and quality of the produced mAb is checked after growth of the cells in perfused bioreactors and in fed batch settings.

A. Perfusion in a 2 Liter Bioreactor.

Cells are seeded in suspension medium in the absence of selecting agents at a concentration of approximately $0.5 \times 10^6$ cells per ml and perfusion is started after a number of days when cell density reaches approximately 2 to $3 \times 10^6$ cells per ml. The perfusion rate is generally 1 volume per 24 hours with a bleed of approximately 250 ml per 24 hours. In this setting, cells stay normally at a constant density of approximately $5 \times 10^6$ cells per ml and a viability of almost 95% for over a month. The mAb production levels are determined on a regular basis.

B. Fed Batch in a 2 Liter Bioreactor.

In an initial run, mAb producing PER.C6 suspension cells that are grown on roller bottles are used to inoculate a 2 liter bioreactor in the absence of selecting agents to a density of 0.3 to 0.5 million cells per ml in a working volume of 300 to 500 ml and are left to grow until the viability of the cell culture drops to 10%. As a culture lifetime standard, it is determined at what day after inoculation the viable cell density drops beneath 0.5 million cells per ml. Cells normally grow until a density of 2 to 3 million cells per ml, after which the medium components become limiting and the viability decreases. Furthermore, it is determined how much of the essential components, such as glucose and amino acids in the medium are being consumed by the cells. Next to that, it is determined what amino acids are being produced and what other products are accumulating in the culture. Depending on this, concentrated feeding samples are being produced that are added at regular time points to increase the culture lifetime and thereby increase the concentration of the mAb in the supernatant. In another setting, 10× concentrated medium samples are developed that are added to the cells at different time points and that also increase the viability of the cells for a longer period of time, finally resulting in a higher concentration of mAb in the supernatant.

Example 23

Transient Expression of Humanized Recombinant Monoclonal Antibodies

The correct combinations of the UBS-54 heavy and light chain genes containing vectors were used in transient transfection experiments in PER.C6 cells. For this, it is not important which selection marker is introduced in the plasmid backbone, because the expression lasts for a short period (two to three days). The transfection method is generally lipofectamine, although other cationic lipid compounds for efficient transfection can be used. Transient methods are extrapolated from T25 flasks settings to at least 10-liter bioreactors. Approximately 3.5 million PER.C6 and PER.C6/E2A cells were seeded at day 1 in a T25 flask. At day 2, cells were transfected with, at most, 8 µg plasmid DNA using lipofectamine and refreshed after two to four hours and left for two days. Then, the supernatant was harvested and antibody titers were measured in a quantitative ELISA for human IgG1 immunoglobulins (CLB, see also Example 26). Levels of total human antibody in this system are approximately 4.8 µg/million seeded cells for PER.C6 and 11.1 µg/million seeded cells for PER.C6/E2A. To determine how much of the produced antibody is of full size and built up from two heavy and two light chains, as well as the expression levels of the heavy and/or light chain alone and connected by disulfide bridges, control ELISAs recognizing the sub-units separately are developed. Different capturing and staining antibody combinations are used that all detect human(ized) IgG1 sub-units. Supernatants of PER.C6 transfectants (transfected with control vectors or pUBS-Heavy2000/Hyg(−) and pUBS-Light2001/DHFRwt) were checked for full sized mAb production (FIG. 24) (of the incorporated '007 application). Samples were treated with and without DTT, wherein one can distinguish between full sized mAb (non-reduced) and heavy and light chain separately (reduced). As expected, the heavy chain is only secreted when the light chain is co-expressed and most of the antibody is of full size.

Example 24

Scale-Up System for Transient Transfections

PER.C6 and derivatives thereof are used for scaling up the DNA transfections system. According to Wurm and Bernard (1999), transfections on suspension cells can be performed at 1 to 10 liter set-ups in which yields of 1 to 10 mg/l (0.1 to 1 pg/cell/day) of recombinant protein have been obtained using electroporation.

A need exists for a system in which this can be well controlled and yields might be higher, especially for screening of large numbers of proteins and toxic proteins that cannot be produced in a stable setting. Moreover, since cell lines such as CHO are heavily affected by apoptosis-inducing agents such as lipofectamine, the art teaches that there is a need for cells that are resistant to this. Since PER.C6 is hardly affected by transfection methods, it seems that PER.C6 and derivatives thereof are useful for these purposes. One to 50 liter suspension cultures of PER.C6 and PER.C6/E2A growing in adjusted medium to support transient DNA transfections using purified plasmid DNA are used for electroporation or other methods, performing transfection with the same expression plasmids. After several hours, the transfection medium is removed and replaced by fresh medium without serum. The recombinant protein is allowed to accumulate in the supernatant for several days, after which the supernatant is harvested and all the cells are removed. The supernatant is used for down stream processing to purify the recombinant protein.

Example 25

Scale Up System for Viral Infections

Heavy and light chain cDNAs of the antibodies described in Examples 3, 4 and 5 are cloned into recombinant adenoviral adapter plasmids separately and in combination. The combinations are made to ensure an equal expression level for both heavy and light chains of the antibody to be formed. When heavy and light chains are cloned separately, viruses are being produced and propagated separately, of which the infectability and the concentration of virus particles are determined and finally co-infected into PER.C6 and derivatives thereof to produce recombinant mAbs in the supernatant. Production of adapter vectors, recombinant adenoviruses and mAbs is as described for recombinant EPO (see, Examples 13 and 14).

Example 26

Development of an ELISA for Determination of Human mAbs

Greiner microlon plates #655061 were coated with an anti-human IgG1 kappa monoclonal antibody (Pharmingen #M032196 0.5) with 100 µl per well in a concentration of 4 µg per ml in PBS. Incubation was performed overnight at 4° C. or for 90 minutes at 37° C. Then, wells were washed three times with 0.05% Tween/PBS (400 µl per well) and subsequently blocked with 100 µl 5% milk dissolved in 0.05% Tween/PBS per well for 30 minutes at 37° C. and then, the plate was washed three times with 400 µl 0.05% Tween/PBS per well. As a standard, a purified human IgG1 antibody was used (Sigma, #108H9265) diluted in 0.5% milk/0.05% Tween/PBS in dilutions ranging from 50 to 400 ng per ml. Per well, 100 µl of the standard was incubated for one hour at 37° C. Then, the plate was washed three times with 400 µl per well 0.05% Tween/PBS. As the second antibody, a biotin labeled mouse monoclonal anti-human IgG1 antibody was used (Pharmingen #M045741) in a concentration of 2 ng per ml. Per well, 100 µl of this antibody was added and incubated for one hour at 37° C. and the wells were washed three times with 400 µl 0.05% Tween/PBS.

Subsequently, conjugate was added: 100 µl per well of a 1:1000 dilution of Streptavidin-HRP solution (Pharmingen #M045975) and incubated for one hour at 37° C., and the plate was again washed three times with 400 µl per well with 0.05% Tween/PBS.

One ABTS tablet (Boehringer Mannheim #600191-01) was dissolved in 50 ml ABTS buffer (Boehringer Mannheim #60328501) and 100 µl of this solution was added to each well and incubated for one hour at RT or 37° C. Finally, the OD was measured at 405 nm. Supernatant samples from cells transfected with mAb encoding vectors were generally dissolved and diluted in 0.5% milk/0.05% Tween/PBS. If samples did not fit with the linear range of the standard curve, other dilutions were used.

Example 27

Production of Influenza HA and NA Proteins in a Human Cell for Recombinant Subunit Vaccines cDNA sequences of genes encoding hemaglutinin (HA) and neuraminidase (NA) proteins of known and regularly appearing novel influenza virus strains are being determined and generated by PCR with primers for convenient cloning into pcDNA2000, pcDNA2001, pcDNA2002 and pcDNAs3000 vectors (see, Example 1). Subsequently, these resulting expression vectors are being transfected into PER.C6 and derivatives thereof for stable and transient expression of the recombinant proteins to result in the production of recombinant HA and NA proteins that are, therefore, produced in a complete standardized way with human cells under strict and well-defined conditions. Cells are allowed to accumulate these recombinant HA and NA proteins for a standard period of time. When the pcDNAs3000 vector is used, it is possible to clone both cDNAs simultaneously and have the cells produce both proteins at the same time. From separate or combined cultures, the proteins are being purified following standard techniques and final HA and NA titers are being determined and activities of the proteins are checked by persons skilled in the art. Then, the purified recombinant proteins are used for vaccination studies and finally used for large-scale vaccination purposes.

The HA1 fragment of the swine influenza virus A/swine/Oedenrode/7C/96 (Genbank accession number AF092053) was obtained by PCR using a forward primer with the following sequence: 5' ATT GGC GCG CCA CCA TGA AGA CTA TCA TTG CTT TGA GCT AC 3' (SEQ ID NO:30) corresponding to the incorporated '007 application, and with a reverse primer with the following sequence: 5' GAT GCT AGC TCA TCT AGT TTG TTT TTC TGG TAT ATT CCG 3' (SEQ ID NO:31) corresponding to the incorporated '007 application. The resulting 1.0 kb PCR product was digested with AscI and NheI restriction enzymes and ligated with AscI and NheI-digested and purified pcDNA2000/DHFRwt vector, resulting in pcDNA2001/DHFRwt-swHA1. Moreover, the HA2 fragment of the same virus was amplified by PCR using the same forward primer as described for HA1 and another reverse primer with the following sequence: 5' GAT GCT AGC TCA GTC TTT GTA TCC TGA CTT CAG TTC AAC ACC 3' (SEQ ID NO:32) corresponding to the incorporated '007 application. The resulting 1.6 kb HA2 PCR product was cloned in an identical way as described for HA1, resulting in pcDNA2001/DHFRwt-swHA2.

Example 28

Integration of cDNAs Encoding Post-Translational Modifying Enzymes

Since the levels of recombinant protein production in stable and transiently transfected and infected PER.C6 and PER.C6/E2A are extremely high and since a higher expression level is usually obtained upon DHFR dependent amplification due to increase of MTX concentration, an "out-titration" of the endogenous levels of enzymes that are involved in post-translational modifications might occur.

Therefore, cDNAs encoding human enzymes involved in different kinds of post-translational modifications and processes such as glycosylation, phosphorylation, carboxylation, folding and trafficking are being overexpressed in PER.C6 and PER.C6/E2A to enable a more functional recombinant product to be produced to extreme levels in small and large settings. It was shown that CHO cells can be engineered in which an alpha-2,6-sialyltransferase was introduced to enhance the expression and bioactivity of tPA and human erythropoietin (Zhang et al., 1998, Minch et al., 1995, Jenkins et al., 1998). Other genes such as beta 1,4-galactosyltransferase were also introduced into insect and CHO cells to improve the N-linked oligosaccharide branch structures and to enhance the concentration of sialic acids at the terminal residues (Weikert et al., 1999; Hollister et al., 1998). PER.C6 cells are modified by integration of cDNAs encoding alpha 2,3-sialyltransferase, alpha 2,6-sialyltransferase and beta 1,4-galactosyltransferase proteins to further increase the sialic acid content of recombinant proteins produced on this human cell line.

Example 29

Inhibition of Apoptosis by Overexpression of Adenovirus E1B in CHO-dhfr Cells It is known that CHO cells, overexpressing recombinant exogenous proteins, are highly sensitive for apoptotic signals, resulting in a generally higher death rate among these stable producing cell lines as compared to the wild-type or original cells from which these cells were derived. Moreover, CHO cells die of apoptotic effects when agents such as lipofectamine are being used in transfection studies. Thus, CHO cells have a great disadvantage in recombinant protein production in the sense that the cells are very easily killed by apoptosis due to different reasons. Since it is known that the E1B gene of adenovirus has anti-apoptotic effects (White et al., 1992; Yew and Berk 1992), stable CHO-dhfr cells that express both heavy and light chains of the described antibodies (see, Examples 3, 4 and 5) are being transfected with adenovirus E1B cDNAs to produce a stable or transient expression of the E1B proteins to finally ensure a lower apoptotic effect in these cells and thereby increase the production rate of the recombinant proteins. Transiently transfected cells and stably transfected cells are compared to wild-type CHO-dhfr cells in FACS analyses for cell death due to the transfection method or due to the fact that they over-express the recombinant proteins.

Stable CHO cell lines are generated in which the adenovirus E1B proteins are overexpressed. Subsequently, the apoptotic response due to effects of, for instance, Lipofectamine in these stable E1B producing CHO cells is compared to the apoptotic response of the parental cells that did not receive the E1B gene. These experiments are executed using FACS analyses and commercially available kits that can determine the rate of apoptosis.

Example 30

Inhibition of Apoptosis by Overexpression of Adenovirus E1B in Human Cells

PER.C6 cells and derivatives thereof do express the E1A and E1B genes of adenovirus. Other human cells, such as A549 cells, are being used to stably overexpress adenovirus E1B to determine the anti-apoptotic effects of the presence of the adenovirus E1B gene as described for CHO cells (see, Example 29). Most cells do respond to transfection agents such as lipofectamine or other cationic lipids, resulting in massive apoptosis and finally resulting in low concentrations of the recombinant proteins that are secreted, simply due to the fact that only few cells survive the treatment. Stable E1B overexpressing cells are compared to the parental cell lines in their response to overexpression of toxic proteins or apoptosis inducing proteins and their response to transfection agents such as lipofectamine.

Example 31

Generation of PER.C6 Derived Cell Lines Lacking a Functional DHFR Protein

PER.C6 cells are used to knock out the DHFR gene using different systems to obtain cell lines that can be used for amplification of the exogenous integrated DHFR gene that is encoded on the vectors that are described in Examples 1 to 5 or other DHFR expressing vectors. PER.C6 cells are screened for the presence of the different chromosomes and are selected for a low copy number of the chromosome that carries the human DHFR gene. Subsequently, these cells are used in knock-out experiments in which the open reading frame of the DHFR gene is disrupted and replaced by a selection marker. To obtain a double knock-out cell line, both alleles are removed via homologous recombination using two different selection markers or by other systems as, for instance, described for CHO cells (Urlaub et al., 1983).

Other systems are also applied in which the functionality of the DHFR protein is lowered or completely removed, for instance, by the use of anti-sense RNA or via RNA/DNA hybrids, in which the gene is not removed or knocked out, but the down stream products of the gene are disturbed in their function.

Example 32

Long-Term Production of Recombinant Proteins Using Protease and Neuraminidase Inhibitors Stable clones described in Example 8 are used for long-term expression in the presence and absence of MTX, serum and protease inhibitors. When stable or transfected cells are left during a number of days to accumulate recombinant human EPO protein, a flattening curve instead of a straight increase is observed, which indicates that the accumulated EPO is degraded in time. This might be an inactive process due to external factors such as light or temperature. It might also be that specific proteases that are produced by the viable cells or that are released upon lysis of dead cells digest the recombinant EPO protein. Therefore, an increasing concentration of $CuSO_4$ is added to the culture medium after transfection and on the stable producing cells to detect a more stable production curve. Cells are cultured for several days and the amount of EPO is determined at different time points. $CuSO_4$ is a known inhibitor of protease activity, which can be easily removed during down stream processing and EPO purification. The most optimal concentration of $CuSO_4$ is used to produce recombinant human EPO protein after transient expression upon DNA transfection and viral infections. Furthermore, the optimal concentration of $CuSO_4$ is also used in the production of EPO on the stable clones. In the case of EPO in which the presence of terminal sialic acids is important to ensure a long circulation half-life of the recombinant protein, it is necessary to produce highly sialylated EPO. Since living cells produce neuraminidases that can be secreted upon activation by stress factors, it is likely that produced EPO lose their sialic acids due to these stress factors and produced neuraminidases. To prevent clipping off of sialic acids, neuraminidase inhibitors are added to the medium to result in a prolonged attachment of sialic acids to the EPO that is produced.

Example 33

Stable Expression of Recombinant Proteins in Human Cells Using the Amplifiable Glutamine Synthetase System PER.C6 and derivatives thereof are being used to stably express recombinant proteins using the glutamine synthetase (GS) system. First, cells are being checked for their ability to grow in glutamine-free medium. If cells cannot grow in glutamine-free medium, this means that these cells do not express enough GS, finally resulting in death of the cells. The GS gene can be integrated into expression vectors as a selection marker (as is described for the DHFR gene) and can be amplified by increasing the methionine sulphoximine (MSX) concentration resulting in overexpression of the recombinant protein of interest, since the entire stably integrated vector will be co-amplified as was shown for DHFR. The GS gene expression system became feasible after a report of Sanders et al. (1984) and a comparison was made between the DHFR selection system and GS by Cockett et al. (1990). The production of recombinant mAbs using GS was first described by Bebbington et al. (1992).

The GS gene is cloned into the vector backbones described in Example 1 or cDNAs encoding recombinant proteins and heavy and light chains of mabs are cloned into the available vectors carrying the GS gene. Subsequently, these vectors are transfected into PER.C6 and selected under MSX concentrations that will allow growth of cells with stable integration of the vectors.

Example 34

Production of Recombinant HIV gp120 Protein in a Human Cell

The cDNA encoding the highly glycosylated envelope protein gp120 from Human Immunodeficiency Virus (HIV) is determined and obtained by PCR using primers that harbor a perfect Kozak sequence in the upstream primer for proper translation initiation and convenient restriction recognition sequences for cloning into the expression vectors described in Example 1. Subsequently, this PCR product is sequenced on both strands to ensure that no PCR mistakes are being introduced.

The expression vector is transfected into PER.C6, derivatives thereof and CHO-dhfr cells to obtain stable producing cell lines. Differences in glycosylation between CHO-produced and PER.C6 produced gp120 are being determined in 2D electrophoresis experiments and subsequently in Mass Spectrometry experiments, since gp120 is a heavily glycosylated protein with mainly O-linked oligosaccharides. The recombinant protein is purified by persons skilled in the art and subsequently used for functionality and other assays. Purified protein is used for vaccination purposes to prevent HIV infections.

Example 35

Transient Expression of Recombinant Proteins on PER.C6 Cells Mediated by E1A/E2A-Deleted Ad5 Infection Transient production of recombinant proteins using plasmid DNA in cell lines in suspension is currently performed using for example $CaPO_4$ co-precipitation or PEI (poly-ethylenimine) reagents. The transfection efficiency and consequently protein yield are in general low and range between a few to 25 mg/l at $\geq 1$ liter scale. In the examples below a transient expression system is presented that makes use of recombinant adenoviruses that are replication deficient in the cell line used for the production of proteins. The transient expression system is very efficient allowing for easy up-scaling to 10 liters and further when used in suspension cells. In these examples, the recombinant Ad5-based adenoviruses are deleted for the E1 and E2A regions and for that reason can only be generated on cell lines that provide both functions, as for example PER.E2A cells (see U.S. Pat. No. 6,395,519).

Recombinant viruses that are both E1 and E2A deleted were generated by a homologous recombination procedure using a plasmid-based system as described in U.S. Pat. No. 6,878,549. This system consists of a first construct called adapter plasmid (pAdApt) that contains Ad5 sequences 1 to 454 including the left ITR and packaging signal, an expression cassette replacing the E1 gene, and an Ad5 fragment corresponding to nucleotides 3511 to 6095. The expression cassette consists of the human CMV promoter, a multiple cloning site (MCS) and the SV40 pA. Nucleic acid encoding the protein of interest was cloned in the MCS. Furthermore, the plasmid-based system consisted of a cosmid (pWE/Ad.AflII-rITRdE2A, see example 10 of U.S. Pat. No. 6,878,549) constituting Ad5 sequences between nucleotide 3534 and 35935 having a deletion encompassing the E2A coding sequences (corresponding to nucleotides 22443-24033; sequence numbering as in Ad5 genbank sequence M73260) and that may be deleted for E3 sequences between Ad5 nucleotide 28592 to 30471.

To evaluate Ad5.dE1.dE2A-mediated protein expression on PER.C6 cells we selected the following transgenes, representing three classes of proteins of interest:

1. ACE2, the cellular receptor for SARS coronavirus (SARS-CoV) and S1-spike, the viral spike protein of SARS-CoV both representing membrane proteins,
2. s.ACE2 and S565, the soluble forms of ACE2 and S1-spike respectively belonging to the class of secreted proteins,
3. SARS-AB; an antibody against SARS-CoV spike protein (ter Meulen et al, Lancet, 2004; 363(9427): 2139-41).

Generation of Various Adapter Plasmids

In order to produce E1.E2A-deleted recombinant adenoviruses using this plasmid system, first several pAdApt plasmids comprising the transgenes, as listed above, were constructed using conventional molecular biological techniques.

Generation of pAdApt.S1-Spike and pAdApt.S565

The cDNA of S1-spike (3767 bp; J. Virol. 2005; 79(3): 1635-1644.) was codon-optimised for optimal expression in human cells by GENEART (Regensburg, Germany) and cloned into the expression cassette of pAdApt, resulting in pAdApt.S1-spike.

pAdApt.S565, the adapter plasmid containing the truncated form lacking the trans-membrane region (referred to as 'secreted' or 'soluble' form) of S1-spike was generated after subcloning into the pAdApt-expression cassette of a restriction fragment comprising the N terminal 1695 bp of S1-spike. S565, a fragment containing the region responsible for binding to ACE2 was fused in frame to a myc/his tag previously introduced in pAdApt, enabling purification and detection of the expressed protein.

Generation of pAdApt.ACE2 and pAdApt.sACE2

The cDNA encoding the full-length cellular receptor for SARS-CoV (ACE2; 2417 bp; Genbank sequence AF291820) was synthesized by GENEART and cloned into the expression cassette of pAdApt, resulting in pAdApt.ACE2.

s.ACE2, the truncated variant of ACE2 lacking the transmembrane region (aa residues 741-805 of ACE2) was generated by cloning the 2217 bp coding region (corresponding to residues 1 to 739 of ACE2) into the expression cassette of pAdApt in frame with and upstream of a myc/his taq. The final plasmid was named pAdApt.sACE2.

Generation of pAdApt.SARS-AB

Genes encoding the variable heavy (VH) and variable light chain (VL) of scFv 03-014; an antibody against the viral spike protein (S1) of SARS-CoV (ter Meulen et al, Lancet, 2004; 363(9427): 2139-41)) were constructed synthetically by GENEART. These genes were separately subcloned into plasmids that already contained an appropriate leader sequence and either the constant CH1, CH2 and CH3 regions of the heavy chain (HC) or Ckappa, the constant region of the light chain (LC) resulting in subclones containing the complete (constant and variable) SARS-AB HC and SARS-AB LC respectively. To enable translation of HC and LC from one transcript, a fragment including an Internal Ribosome Entry Site (IRES) sequence was inserted in between HC and LC and cloned in the expression cassette of pAdApt (thereby replacing the original CMV promoter for a CMV promoter containing an additional chimeric intron). Initially identical leader sequences were used upstream the heavy and light chains. In order to circumvent vector instability due to homologous recombination between these identical leaders during virus replication, the leader of the LC was exchanged for another one (sharing 44% homology on nucleotide level) that was demonstrated to be equally functional. The final construct was named pAdApt.SARS-AB.

Virus Generation, Production and Purification.

Generation of recombinant Adenovirus batches with E1 and E2A deleted (Ad5.dE1.dE2A) was accomplished using a lipofectamine mediated co-transfection procedure using 2 μg linearized (Pac I/Sal I digested) pAdApt carrying the various transgenes and 6 μg linearized (Pac I digested) cosmid (pWE/AflII-rITRdE2A). Co-transfection of adherent PER.E2A cells was performed using Lipofectamine-2000 according to manufacturers instructions. Following co-transfection cells were cultured in 25 $cm^2$ flasks and after two days the culture format was expanded to 80 $cm^2$ scale. Upon signs of full cyto-pathic effect (CPE) indicating that functional adenovirus has formed, cells and medium were harvested and recombinant virus was released by freeze-thawing, centrifuged to remove cell debris and supernatants were collected. These cleared supernatants are referred to as crude lysates.

To generate high quality purified viruses, crude lysates were subsequently used to plaque purify the recombinant viruses according to standard methods. A number of isolated plaques for each virus were isolated and amplified on PER.E2A cells in 24 well plates to generate crude lysates for analysis. All plaques were tested for virus integrity and identity by PCR analysis of the transgene, E2A and the E3 region. Based on these results PER.E2A host cells were infected with part of the plaque-amplified material and grown at 34° C. until full CPE was observed. Cells and medium were harvested and stored at −20° C. Crude lysates were prepared and part of this material was used for infection in subsequent steps. In this manner the virus was expanded from amplified plaque (1 ml) to 25 $cm^2$ flask (5 ml), 175 $cm^2$ flask (15 ml) and finally to a triple layer flask (175III $cm^2$, 50 ml). In a production run (48×175III $cm^2$) PER.E2A cells were infected using the supernatant of the triple layer as inoculum. Productions were harvested when CPE was visible and virus was purified from the packaging cells using a two-step CsCl banding procedure. Purification of intact virus particles from remains (protein and fragmented DNA) of the host cell was performed using a second CsCl gradient centrifugation.

Purified virus batches were tested for the presence of intact transgene, and presence or absence of E3 and E2A regions respectively. Transgene expression and both titer and infectious titer were determined using standard western blot, High Pressure Liquid Chromatography (HPLC) and Tissue Culture Infectious Dose 50 ($TCID_{50}$) assays respectively. In all virus batches intact transgenes, presence of E3 and absence of E2A regions were confirmed by PCR using specific primers.

Transgene expression of all batches was tested in adherent PER.C6 cultures after two days of infections using MOI's ranging from 0 to 3000 vp/cell. Presence in the culture medium of (myc/his-tagged) S565 and s.ACE2 was demonstrated by western blot using mouse-anti-c.myc (HRP-conjugated), while SARS-AB was detected on western blot using donkey-anti-human IgG (HRP-conjugated). Proper expression of the transmembrane proteins S1-spike and ACE2 on the cell membranes were detected using FACS after cell staining with human-anti-spike (CR3014)/goat-anti-human IgG (PE-conjugated) for S1-spike and goat-anti-ACE2/donkey anti IgG (PE-conjugated) for ACE2.

Instead of generating purified batches of Ad5.dE1.dE2A viruses, the crude lysates can be directly used to inoculate PER.C6 cells and produce recombinant proteins. The crude lysate can also be first amplified on PER.E2A cells grown in larger formats to generate more crude lysate, enabling inoculation of a larger volume with more PER.C6 cells for protein production.

Transient Expression of Proteins in PER.C6 Cells

To study protein synthesis in PER.C6 cells, virus batches were produced on PER-E2A cells as described above, and used to infect PER.C6 cells in roller bottles and shaker flasks according to the method outlined below. For infection of PER.C6 cells in roller bottles (100 ml culture volume) cells were seeded at $0.3\times10^6$ cells/ml in AEM medium (Invitrogen) supplemented with L-glutamine. Cells were cultured in roller bottles (2 rpm) at 37° C. in an incubator at 10% $CO_2$. When cell concentrations reached $2\times10^6$ cells/ml, cultures were centrifuged for 10 minutes at 500×g and pellets were resuspended in 100 ml fresh AEM/L-glutamine at a final cell concentration of $2.5\times10^6$ cells/ml. The next day cells were counted using the Casey counter and virus was added to the roller bottles corresponding to the desired MOI.

For infection of PER.C6 cells in shaker flasks (25 ml culture volume) cells grown in roller bottles (as above) were counted, centrifuged and cell pellets were resuspended in fresh AEM/L-glutamine at $2.5 \times 10^6$ cells/ml after which virus was added at the desired MOI. Cells were cultured in shaker flasks (75 rpm) at 37° C. at 10% $CO_2$.

Harvest of the medium was done between day 3 and 14, depending on the type of experiment and the protein expressed. The method described above for roller bottles and shaker flasks can simply be adapted and applied for other culture formats by persons skilled in the art. Also the mentioned cell densities and medium can be modified to achieve higher production levels.

Example 36

Yields of Various Recombinant Proteins Produced in PER.C6 Cells Mediated by Ad5.dE1.dE2A Infection The following experiments were performed to define preferred parameters like multiplicity of infection (MOI), cell density and day of harvest for Ad5.dE1.dE2A-mediated protein synthesis in PER.C6 cells. In addition, typical yields of the secreted proteins (s.ACE2 and S565) and the yield of SARS-AB obtained in PER.C6 cells mediated by E1.E2A-deleted Ad5 infection is presented.

In order to determine the preferred MOI for protein yield, PER.C6 cells were infected with Ad5.dE1.dE2A.S565 at various MOI's, medium containing S565 protein was collected and quantified by western blot.

Hereto, cells ($1 \times 10^6$ cells/ml) were cultured and infected in shaker flasks (25 ml) in AEM medium according to the procedure described above (example 35). Cells were infected with Ad5.dE1.dE2A.S565 at MOI's of 0, 100, 250, 500, 1000, 1500 and 2000 vp/cell, and cultured for 5 days in AEM. Every day samples were taken from these cultures, centrifuged and the pellets were resuspended in 1 ml PBS. In these samples numbers of total cells and viable cells were measured using the easy counter according to a standard procedure. The supernatants were filtered, proteins were separated by SDS-PAGE and analyzed in western blots using anti-myc monoclonal antibody (FIG. 2). Western blot analysis of samples, taken from day 2 and day 3 after infection with MOI 100, showed one single product of the expected molecular weight of 97 kD. Samples taken from cultures that were infected with the higher (>100) MOI's showed, besides the product of the expected size, an additional product around 64 kD of unknown origin. Based on the presence of this extra fragment, MOI's 250, 500, 1000, 1500 and 2000 vp/cell were considered not to be optimal for further experimental use. Moreover, the amount of produced protein did not increase with the increasing MOI, indicating that there was an excess of virus. These observations indicated that the MOI is preferably <100 vp/cell, and a new infection experiment using MOI's of less then 100 vp/ml was initiated.

Lower MOI's as well as multiple cell densities were included in the next experiment, in order to determine both preferred MOI as well as preferred cell concentrations for protein production in PER.C6 cells. Various PER.C6 cell cultures ($1 \times 10^6$, $2 \times 10^6$ and $2.5 \times 10^6$ cells/ml) were infected with MOI's of 0, 30, 60 and 100 vp/cell. Samples were collected and analyzed similarly as described above. Samples taken on days 2, 3 and 4 were analyzed in western blots and showed the highest signal for MOI 30 at a cell density of $2.5 \times 10^6$ cells/ml although differences between infection with MOI 30 and 60 were within a factor of 2-3.

Similar infection experiments in roller bottles in BMIV medium (a proprietary medium of Crucell Holland B.V.) using MOI of 30 and a cell density of $2.5 \times 10^6$ cells/ml during 7 days confirmed highest product yields on day 4-post infection.

To investigate if MOI 30 also gave good results for expressing an antibody, a similar experiment was performed whereby PER.C6 cells ($2.5 \times 10^6$ cells/ml) were infected with Ad5.dE1.dE2A.SARS-AB at MOIs of 0, 30, 60, 120 and 240 vp/cell. Cultures were monitored and sampled for 8 days. SARS-AB yield was quantified using a standardized AKTA-ProtA method. Increasing SARS-AB concentrations were detected in all cultures over time with final values of 23, 18, 10 and 6 µg/ml on day 8 in cultures infected with MOI 30, 60, 120 and 240 vp/cell respectively showing highest antibody production levels following infection with 30 vp/cell (FIG. 3).

These experiments thus demonstrated efficient protein production in PER.C6 cells in suspension cultures using the E1-E2A-deleted adenoviruses, and led to the surprising observation that best yields were obtained with the lower range of MOIs.

Product Yield and Purity Following E1/E2a-Deleted Adenovirus-Mediated Transient Expression in PER. C6 Cells To determine the yields of the three types of secreted proteins, S565, s.ACE2 and SARS-AB, experiments were performed using the conditions determined above.

PER.C6 roller bottle cultures (100 ml) were infected with MOI 30 and 60 vp/cell at $2.5 \times 10^6$ cells/ml as described above. In case of S565 and s.ACE2, cells were cultured in parallel for 4 days post infection, both in AEM and in BMIV medium. Ad5.dE1.dE2A.SARS-AB infected cells were cultured for 12 days in AEM. Harvested culture media were centrifuged and filtered over a 0.22 µm bottle top filter.

In case of S565 and s.ACE2, total protein concentration in culture harvests was determined using the Micro BCA™ protein assay (Pierce; The Netherlands), according to manufacturers protocol. Samples of the harvests were also serially diluted and separated on SDS-PAGE gels. After colloid blue staining, the gel was optically scanned and all single products (in the linear sample range) present in the individual lanes were digitally integrated and converted to Integrated Optical Density (IOD) values. This enabled the expression of the individual proteins as percentage of total protein per lane and is defined for this example as protein purity. Subsequently, the amount of produced S565 and s.ACE2 was calculated by multiplication of the purity by the total amount of protein. In this way purities of the Ad5-mediated S565 and s.ACE2 in culture harvests were determined, and ranged between 60-75% and 30-40% respectively. These figures demonstrate that the described method herein for transient protein expression is an efficient and clean system to produce proteins. Protein yields were calculated and ranged between 500-600 µg/ml for s.ACE2 and 220-370 µg/ml for S565. Yields are presented in Table 2.

The SARS-AB concentration present in culture medium was determined using HPLC-protA column chromatography standardized for IgG quantitation according to manufacturers protocol, and ranged between 120-140 µg/ml.

Analysis of Purified S565, s.ACE2 and SARS-AB

The secreted proteins S565 and s.ACE2 were chromatographically purified using standard affinity and desalting columns. The soluble (Myc/His tagged) proteins S565 and s.ACE2 were produced in 100 ml roller bottles; expressed proteins present in culture medium were purified on an AKTA explorer (GE-health care) using HisTrap HP (1 ml) affinity and HiTrap desalting (5 ml) columns (GE-health care). Purified proteins were quantified by a micro BCA protein assay (Pierce; The Netherlands), according to manufacturers protocol.

SARS-AB was purified using HiTrap rProtein A protA and HiPrep 26/10 affinity and desalting columns (GE-health care) and quantified by optical density measurements at 280 nm.

Western blot analysis following denaturing SDS-PAGE of sets of serially diluted samples using a mouse-anti-c-myc (HRP-conjugated) MAb for detection of s.ACE2 and S565, and a donkey-anti-human IgG (HRP-conjugated) MAb for detection of SARS-AB, demonstrated the presence of only the products of the expected sizes (FIG. 4), indicating efficient full length product formation and the absence of truncation or degradation of products during synthesis or storage.

SARS-AB Production in PER. C6 Cells Using Crude Lysates

Transient expression of recombinant protein is aimed at the fast production of recombinant proteins in quantities enabling further testing in vitro and in vivo. The experiments described above were performed using purified and quantified adenovirus batches, which take about 3-4 months to complete.

In order to reduce the period of time required for Ad5-mediated transient expression it is desirable to use viruses from crude stocks early in the procedure of virus generation. The next experiment describes the comparison of SARS-AB yield in PER.C6 cells after infection with either Ad5.dE1.dE2A.SARS-AB purified virus or crude lysate (harvested medium containing virus at the moment full-CPE occurred following co-transfection of PER.E2A with pAdApt.SARS-AB and pWE/AflII-rITRdE2A). The two inoculums were referred to in this example as ‘purified virus’ and ‘crude lysate’ respectively. The crude lysate is also referred to in the invention as a ‘crude adenovirus particle compostion’.

Since the virus titer of the crude lysate cannot be accurately measured using standard HPLC methods, infectious titers (IU/ml) were determined using $TCID_{50}$ assays. Generating the crude lysate virus preparation including the $TCID_{50}$ determination takes around 4 weeks, representing a considerable time reduction as compared to the 3-4 months necessary to generate the purified virus batch. In a side-by-side comparison study, PER.C6 cells were infected with purified virus or crude lysate preparations using similar amounts of infectious virus particles (IU), corresponding to an MOI of 30 vp/ml of the purified batch. Cell culture and virus infections of 100 ml roller bottles were performed as described above. The number of total and viable cells was monitored for 12 days post infection. Medium samples were collected and measured for SARS-AB production as described above. As shown in FIG. 5, both infections showed increasing SARS-AB concentration during the sampling period with higher product yields for cultures infected with crude lysate virus preparation (120 μg/ml) compared to the ones infected with the purified virus (80 μg/ml). SARS-AB generated by both types of virus inoculums was harvested on day 12 and purified using AKTA-protA chromatography. Quality of the SARS-AB batches was analyzed using non-reduced colloid blue stained SDS-PAGE (FIG. 6), according to standard protocols.

Both batches generated from purified adenovirus or from crude lysate preparations showed identical patterns compared with the positive control (the SARS-antibody from a stably transfected PER.C6 cell line (CR3014)).

This experiment thus demonstrates that quality and quantity of the SARS-AB produced using similar low infectious doses (MOI 30=4 IU/cell) of crude lysates and purified virus were comparable with products isolated from a stable expressing PER.C6-derived cell line. Thus it is possible to use crude lysates in the transient expression method described herein, which significantly reduces the time lines for transient production of proteins.

Example 37

Functional Analysis of Virus Mediated Transiently Produced Proteins

In the next experiments transiently produced proteins produced according to the methods described in example 36 were analyzed for having proper structural conformation by testing specific interaction with a relevant ligand or target in binding assays.

Proper expression and structural integrity of the membrane bound proteins ACE2, S1-spike and the secreted protein s.ACE2 was measured using FACS as outlined below.

Correct protein structure of transiently produced S565 and SARS-AB were tested in an ELISA-based assay for their ability to bind to CR3014 and to S1-spike, respectively. CR3014 is used as a positive control antibody and is isolated from a PER.C6-derived cell line expressing the SARS-AB in a stable manner.

Functional Analysis of S565

Functionality of S565 was analyzed in an ELISA-based assay. Serially diluted purified myc/his-tagged S565 was bound to mouse-anti-c.myc coated 96-wells plates, and subsequently incubated with a fixed CR3014 (anti-SARS Ab) concentration. Binding of CR3014 to S565 was detected using peroxidase-conjugated AffiniPure donkey anti-human IgG (Jackson Immuno Research), according to standard methods. The relationship between optical density measured at 492 nm and the S565 concentration showed an S-curve representative for specific interaction between an antibody and its substrate. The result of this assay demonstrated the ability of control antibody CR3014 to bind to the transiently produced and purified S565, indicating proper folding of this secreted protein (FIG. 7A).

Functional Analysis of SARS-AB

The purified S565 protein (of which the integrity was confirmed, see previous paragraph) preparation was used to analyze the two purified SARS-AB batches produced in PER.C6 cells, infected with purified virus or crude lysates of Ad5.dE1.dE2A.SARS-AB (described in example 36). To this end a fixed amount of purified myc/his-tagged S565 was linked to mouse-anti-c.myc-coated 96-wells plates, and subsequently incubated with transiently produced SARS-AB in serial dilutions. Binding of SARS-AB to S565 was detected using peroxidase-conjugated AffiniPure donkey anti-human IgG (Jackson Immuno Research) according to standard methods. S-curves generated in this binding assay demonstrated the ability of the tested SARS-AB batches to bind the immobilized S565 (FIG. 7B). Thus, the antibody produced using the method of the invention was functional in binding its target.

Functional Analysis of S1-Spike

Transiently produced SARS-AB (functionality verified, see previous paragraph), was used to confirm proper conformation of S1-spike, the full length SARS spike protein, in a FACS assay. Hereto, suspension PER.C6 cells were infected with MOI 30 and MOI 100 vp/cell of Ad5.dE1.dE2A.S1-spike. Two days post-infection, cells were harvested and incubated with SARS-AB. The amount of SARS-AB bound to transiently expressed S1-spike on PER.C6 cell membranes was detected by incubation with goat-anti-human-IgG (PE-conjugated) and analyzed by FACS. Detection of positive cell populations of 95% and 91% by FACS analysis for MOI 30 and 100 vp/ml respectively, demonstrated binding of SARS-AB to S1-spike. Thus, S1-spike had a proper conformation when transiently produced in the Ad5.dE1.dE2A/PER.C6 protein production platform (FIG. 8).

Functional Analysis of s.ACE2

Transiently expressed S1.spike (proper conformation demonstrated, see previous paragraph) was used in a functional assay for s.ACE2. Proper conformation of s.ACE2 was determined by its ability to interact with S1-spike and measured by FACS. Briefly, suspension PER.C6 cells were infected with 30 vp/cell of Ad5.dE1.dE2A.S1-spike and cultured for two days, then cells were harvested and s.ACE2 (40 μg/ml) was added to the cells. The amount of s.ACE2 bound to membranes containing transiently expressed S1-spike was detected by incubating the cells with mouse-anti-c-Myc-FITC and analyzed using FACS. Detection of a positive cell population of 70% by FACS demonstrated the ability of s.ACE2 to bind to S1-spike and therefore demonstrated proper conformation of virus-mediated transiently produced s.ACE2 in PER.C6 cells (FIG. 9).

Functional Analysis of ACE2

Expression and structural integrity of the transmembrane ACE2 protein were analyzed by FACS, using a commercially available monoclonal antibody. Hereto, shaker flasks (25 ml; $2.5\times10^6$ cells/ml) and roller bottles (100 ml; $2.5\times10^6$ cells/ml) were infected in parallel with Ad5.dE1.dE2A.ACE2 at 0, 30, 60 and 120 vp/cell and harvested two days following infection. Cells were incubated subsequently with goat-anti-human ACE-2 IgG and PE-conjugated anti-human IgG (100-fold dilution) and analyzed using FACS-Calibur. In both culture formats, 80-96% of positive cells were measured for various MOI's and confirmed proper expression of ACE2 on the cell surface of PER.C6 cells following transient expression. In addition, it also demonstrated that shaker flasks and roller bottles were infected with similar high efficiency (FIG. 10).

Tables

TABLE 1

| moi (virus particles per cell) | ratio (virus particles/ infectious units) | culture conditions | culture medium | refreshment | EPO yields (ELISA units/1E6 cells/day) |
|---|---|---|---|---|---|
| 200 | 330 | roller bottle | JRH | day 3 | 240 |
| 200 | 330 | roller bottle | JRH | none | 190 |
| 20 | 330 | roller bottle | JRH | day 3 | 80 |
| 20 | 330 | roller bottle | JRH | none | 70 |
| 200 | 560 | 6-wells | DMEM + FBS | every day | 60 |

(=Table 5 of the incorporated '409 application).

EPO yields obtained after viral infections. Yields per million seeded cells were determined with an EPO ELISA on supernatants from PER.C6 cells that were infected with recombinant IG.Ad5.AdApt.EPO.dE2A adenovirus as described in Example 14. Two different batches of the virus were used with different vp/IU ratios (330 and 560) in two different settings (roller bottle suspension cultures and 6-wells attached cultures).

TABLE 2

| Protein | Medium | MOI | Volumetric (μg/ml) | Specific production (pg/cell/day) |
|---|---|---|---|---|
| s.ACE2 | AEM | 60 | 501 | 50 |

Volumetric and specific protein production levels in PER.C6 cells following virus-mediated production of various proteins. Cells were cultured in AEM or BMIV medium in roller bottles (100 ml; $2.5\times10^6$ cells/ml) and infected with MOI's of 30 or 60 vp/cell Ad5.dE1.dE2A vectors expressing s.ACE2, S565 or SARS-AB. See example 36 for details.

REFERENCES

Baldi L, Hacker DL, Adam M, FM Wurm (2007) Recombinant protein production by large scale transient gene expression in mammalian cells: state of the art and future perspectives. *Biotechnol Lett* 29: 677-684

Barbas CF, Kang AS, Lerner RA and Benkovic SJ (1991) Assembly of combinatorial antibody libraries on phage surfaces: The gene III site. Proc Natl Acad Sci USA. 88, 7978.

Baldwin RW, Byers VS (1986) Monoclonal antibodies in cancer treatment. Lancet 1, 603-605.

Bebbington C.R., G. Renner, S. Thomson, D. Abrams, and G.T. Yarranton (1992) High-level expression of a recombinant antibody from myeloma cells using a glutamine synthetase gene as an amplifiable selectable marker. *Biotechnology* 10:169-175.

Borrebaeck CAK, Malmborg A-C and Ohlin M (1993) Does endogenous glycosylation prevent the use of mouse monoclonal antibodies as cancer therapeutics? Immunology Today 14, 477-479.

Borrebaeck CAK (1999) Human monoclonal antibodies: The emperor's new clothes? Nature Biotech. 17, 621.

Boshart W., F. Weber, G. Jahn, K. Dorsch-Hasler, B. Fleckenstein, and W. Schaffner (1985) A very strong enhancer is located upstream of an immediate early gene of human cytomegalovirus. *Cell* 41:521-530.

Bruggeman M, Spicer C, Buluwela L, Rosewell I, Barton S, Surani MA, Rabbits TH (1991) Human antibody production in transgenic mice: expression from 100 kb of the human IgH locus. Eur J Immunol. 21, 1323-1326.

Bulens F., A.-M. Vandamme, H. Bemar, L. Nelles, R.H. Lijnen, and D. Collen (1991) Construction and characterization of a functional chimeric murine-human antibody directed against human fibrin fragment-D dimer. *Eur. J. Biochem.* 195:235-242.

Burton DR and Barbas III CF (1994) Human antibodies from combinatorial libraries. Adv Immunol. 57, 191-280.

Carter P, Presta L, Gorman CM, Ridgway JB, Henner D, Wong WL, Rowland AM, Kotts C, Carver ME and Shephard HM (1992) Humanization of an anti-p185HER2 antibody for human cancer therapy. Proc Natl Acad Sci USA 89, 4285-4289.

Clarkson T, Hoogenboom HR, Griffiths A and Winter G (1991) Making antibody fragments using phage display libraries. Nature 353, 624.

Cockett M.I., C.R. Bebbington, G.T. Yarranton (1990) High level expression of tissue inhibitor of metalloproteinases in Chinese hamster ovary cells using glutamine synthetase gene amplification. *Bio/technology* 8:662-667.

Crowe J.S., V.S. Hall, M.A. Smith, H.J. Cooper, and J.P. Tite (1992) Humanized monoclonal antibody CAMPATH-1H: myeloma cell expression of genomic constructs, nucleotide sequence of cDNA constructs and comparison of effector mechanisms of myeloma and Chinese hamster ovary cell-derived material. *Clin. Exp. Immunol.* 87:105-110.

Das G.C., S.K. Niyogi, and N.P. Salzman (1985) SV40 promoters and their regulation. *Prog. Nucleic Acid Res. Mol. Biol.* 32:217-236.

Debbas M. and E. White (1993) Wild-type p53 mediates apoptosis by E1A, which is inhibited by E1B. *Genes Dev.* 7:546-554.

Delorme E., T. Lorenzini, J. Giffin, F. Martin, F. Jacobsen, T. Boone, and S. Elliot (1992) Role of glycosylation on the secretion and biological activity of erythropoietin. *Biochemistry* 31:9871-9876.

Farley DC, Brown JL, and KN Leppard (2004) Activation of the early-late switch in adenovirus type 5 major late transcription unit expression by L4 gene products. *J Virol* 78: 1782-1791.

Farrow S.N., J.H. White, I. Martinou, T. Raven, K.T. Pun, C.J. Grinham, J.C. Martinou, R. Brown (1995) Cloning of a bcl-2 homologue by interaction with adenovirus E1B 19K. *Nature* 374:731-733.

Fishwild DM, O'Donnell SL, Bengoechea T, Hudson DV, Harding F, Bernhard SL, Jones D, Kay RM, Higgins KM, Schramm SR, Lonberg N (1996) High-avidity human IgG kappa monoclonal antibodies from a novel strain of minilocus transgenic mice. *Nat. Biotechnol.* 14, 845-851.

Frodin JE, Lefvert AK, Mellstedt H (1990) Pharmacokinetics of the mouse monoclonal antibody 17-1A in cancer patients receiving various treatment schedules. Cancer Res. 50, 4866-4871.

Fussenegger M., J.E. Bailey, H. Hauser, and P.P. Mueller (1999) Genetic optimization of recombinant glycoprotein production by mammalian cells. *Trends Biotechn.* 17:35-42.

Galili U (1993) Interaction of the natural anti-Gal antibody with alpha-galactosyl epitopes: a major obstacle for xenotransplantation in humans. Immunol Today 14, 480-482.

Garnier A, Côté J, Nadeau I, Kamen A, and B Massie (1994). Scale-up of the adenovirus expression system for the production of recombinant protein in human 293S cells. Cytotechnology 15: 145-155.

Garrard L, Yang M, O'Connell M, Kelley R and Henner DJ (1991) Fab assembly and enrichment in a monovalent phage display system. BioTechnology 9, 1373.

Gill D.R., S.E. Smyth, C.A. Goddard, I.A. Pringle, C.F. Higgins, W.H. Colledge, and S.C. Hyde (2001) Increased persistence of lung gene expression using plasmids containing the ubiquitin C or elongation factor 1α promoter. *Gene Therapy* 8:1539-1546.

Goldwasser E., J.F. Eliason, and D. Sikkema (1975) An assay for erythropoietin in vitro at the milliunit level. *Endocrinology* 97:315-23.

Gorman C.M., D. Gies, G. McCray, and M. Huang (1989) The human cytomegalovirus major immediate early promoter can be trans-activated by adenovirus early proteins. *Virology* 171:377-385.

Graham F.L., J. Smiley, W.C. Rusell, and R. Nairn (1977) Characteristics of a human cell line transformed by DNA from human adenovirus type 5. *J. Virol.* 36:59-74.

Green LL, Hardy MC, Maynard-Currie CE, Tsuda H, Louie DM, Mendez MJ, Abderrahim H, Noguchi M, Smith DH, Zeng Y (1994) Antigen-specific human monoclonal antibodies from mice engineered with human Ig heavy and light chain YACs. Nat. Genet. 7, 13-21.

Grundmann U, Nehrlich C, Rein T, Zettlmeissl G (1990) Complete cDNA sequence encoding human beta-galactoside alpha-2,6-sialyltransferase. Nucleic Acids Res. 18: 667.

Hale G, Dyer MJS, Clark MR, Phillips JM, Marcus R, Reichmann L, Winter G and Waldmann H (1988) Remission induction in non-Hodgkin lymphoma with reshaped human monoclonal antibody CAMPATH-1H. Lancet 2, 1394-1399.

Hammerling U., R. Kroon, T. Wilhelmsen, L. Sĵdin (1996) In vitro bioassay for human erythropoietin based on proliferative stimulation of an erythroid cell line and analysis of carbohydrate-dependent microheterogeneity. *J. Pharm. Biomed. An.* 14:1455-1469.

Han J., P. Sabbatini, D. Perez, L. Rao, D. Modha, and E. White (1996) The E1B 19K protein blocks apoptosis by interacting with and inhibiting the p53-inducible and death-promoting Bax protein. *Genes Dev.* 10:461-477.

Havenga M. J., A. B. Werner, D. Valerio, and H. H. van Es (1998) Methotrexate selectable retroviral vectors for Gaucher disease. *Gene Thero.* 5:1379-1388.

He T C, Zhou S, da Costa L T, Yu J, Kinzler K W, and B Vogelstein (1998) A simplified system for generating recombinant adenovirus. *Proc Natl Acad Sci USA* 95: 2509-2514.

Hodges B L, Evans H K, Everett R S, Ding E Y, Serra D, and A Amalfitano (2001) Adenovirus vectors with the 100K gene deleted and their potential for multiple gene therapy applications. *J Virol* 75: 5913-5920.

Hollister J. R., J. H. Shaper, and D. J. Jarvis (1998) Stable expression of mammalian beta-1,4-galactosyltransferase extends the N-glycosylation pathway in insect cells. *Glycobiology* 8:473-480.

Huls G. A., I. A. F. M. Heijnen, M. E. Cuomo, J. C. Koningsberger, L. Wiegman, E. Boel, A.-R. Van der Vuurst de Vries, S. A. J. Loyson, W. Helfrich, G. P. Van Berge Henegouwen, M. Van Meijer, J. De Kruif, and T. Logtenberg (1999) A recombinant, fully human monoclonal antibody with antitumor activity constructed from phage-displayed antibody fragments. *Nature Biotechnol.* 17:276-281.

Isaacs J D, Watts R A, Hazleman B L, Hale G, Keogan M T, Cobbold S P, Waldmann H (1992) Humanized monoclonal antibody therapy for rheumatoid arthritis. Lancet 340, 748-52.

Jacobovits A (1995) Production of fully human antibodies by transgenic mice. Curr Opin Biotechnol. 6, 561-566.

Jenkins N., R. B. Parekh, and D.C. James (1996) Getting the glycosylation right: implications for the biotechnology industry. *Nat. Biotechnol.* 14:975-81.

Jenkins N., L. Buckberry, A. Marc, and L. Monaco (1998) Genetic engineering of alpha 2,6-sialyltransferase in recombinant CHO cells. *Biochem. Soc. Trans.* 26, S115.

Kawashima I., H. Ozawa, M. Kotani, M. Suzuki, T. Kawano, M. Gomibuchi, and T. Tai (1993) Characterization of ganglioside expression in human melanoma cells: immunological and biochemical analysis. *J. Biochem.* (Tokyo) 114: 186-193.

Kay R., F. Takei, and R. K. Humphries (1990) Expression cloning of a cDNA encoding M1/69. *J. Immunol.* 145: 1952-1959.

Kitamura T., T. Tange, T. Terasawa, S. Chiba, T. Kuwaki, K. Miyagawa, Y.-F. Piao, K. Miyazono, A. Urabe, and F.

Takaku (1989) Establishment and characterization of a unique human cell line that proliferates dependently on GM-CSF, IL-3, or erythropoietin. *J. Cell Physiol.* 140:323-334.

Kohler G and Milstein C (1975) Continuous cultures of fused cells secreting antibody of predefined specificity. Nature 256:495.

Krystal G., A. C. Eaves, and C. J. Eaves (1981) A quantitative bioassay for erythropoietin, using mouse bone marrow. *J. Lab. Clin. Med.* 97:144-157.

Krystal G. (1983) A simple microassay for erythropoietin based on 3H-thymidine incorporation into spleen cells from phenylhydrazine treated mice. *Exp. Hematol.* 11:649-660.

Lee E. U., J. Roth, and J.C. Paulson (1989) Alteration of terminal glycosylation sequences on N-linked oligosaccharides of Chinese hamster ovary cells by expression of beta-galactoside alpha 2,6-sialyltransferase. *J. Biol. Chem.* 264:13848-13855.

Levrero M., V. Barban, S. Manteca, A. Ballay, C. Balsamo, M. L. Avantaggiata, G. Natoli, H. Skellekens, P. Tiollais, and M. Perricaudet (1991) Defective and non-defective adenovirus vectors for expression foreign genes in vitro and in vivo. *Gene* 101:195-202.

Lonberg N, Taylor L D, Harding F A, Trounstine M, Higgins K M, Schramm S R, Kuo C, Mashayekh R, Wymore K, McCabe J G (1994) Antigen-specific human antibodies from mice comprising four distinct genetic modifications. Nature 368, 856-859.

Lonberg N, Huszar D (1995) Human antibodies from transgenic mice. Int Rev Immunol. 13, 65-93.

Lowder J N, Meeker T C, Levy R (1985) Monoclonal antibody therapy of lymphoid malignancy. Cancer Surv. 4, 359-375.

Martinez-Salas, E. (1999) Internal ribosome entry site biology and its use in expression vectors *Curr Opin Biotechnol* 10, 458-64.

Massie B, Dionne J, Lamarche N, Fleurent J, and Y Langelier (1995) Improved adenovirus vector provides Herpes Simplex Virus Ribonucleotide Reductase R1 and R2 subunits very efficiently. Bio/Technology 13: 602-608.

McCafferty J, Griffiths A D, Winter G and Chiswell D J (1990) Phage antibodies: filamentous phage displaying antibody variable domains. Nature 348, 552.

Mellstedt H, Frodin J E, Masucci G, Ragnhammar P, Fagerberg J, Hjelm A L, Shetye J, Wersall P, Osterborg A (1991) The therapeutic use of monoclonal antibodies in colorectal carcinoma. Semin Oncol. 18, 462-477.

Mendez M J, Green L L, Corvalan J R, Jia X C, Maynard-Currie C E, Yang X D, Gallo M L, Louie D M, Lee D V, Erickson K L, Luna J, Roy C M, Abderrahim H, Kirschenbaum F, Noguchi M, Smith D H, Fukushima A, Hales J F, Klapholz S, Finer M H, Davis C G, Zsebo K M, Jakobovits A (1997) Functional transplant of megabase human immunoglobulin loci recapitulates human antibody response in mice. Nat. Genet. 15, 146-156.

Minch S. L., P. T. Kallio, and J. E. Bailey (1995) Tissue plasminogen activator coexpressed in Chinese hamster ovary cells with alpha(2,6)-sialyltransferase contains NeuAc alpha(2,6)Gal beta(1,4)Glc-N-AcR linkages. *Biotechn. Prog.* 11:348-351.

Morrison et al. Chimeric human antibody molecules: mouse antigen-binding domains with human constant region domains, Proc. Nat'l Acad. Sci. (USA), 81:6851-55 (1984).

Muchmore E. A., M. Milewski, A. Varki, and S. Diaz (1989) Biosynthesis of N-glycolyneuraminic acid. The primary site of hydroxylation of N-acetylneuraminic acid is the cytosolic sugar nucleotide pool. *J. Biol. Chem.* 264:20216-20223.

Muller N, Derouazi M, Van Tilborgh F, Wulhfard S, Hacker D L, Jordan M, and F M Wurm (2007) Scalable transient gene expression in Chinese hamster ovary cells in instrumented and non-instrumented cultivation systems. *Biotechnol Lett* 29: 703-711.

Nadler L, Stashenko P, Hardy R, Kaplan W, Burton L, Kufe D W, Antman K H, Schlossman S F (1980) Serotherapy of a patient with a monoclonal antibody directed against a human lymphoma-associated antigen. Cancer Res. 40, 3147-3154.

Oi V T, Morrison S L, Herzenberg L A, Berg P (1983) Immunoglobulin gene expression in transformed lymphoid cells. Proc Natl Acad Sci USA. 1983 80, 825-829.

Olive D. M., W. Al-Mulla, M. Simsek, S. Zarban, and W. al-Nakib (1990) The human cytomegalovirus immediate early enhancer-promoter is responsive to activation by the adenovirus-5 13S E1A gene. *Arch. Virol.* 112:67-80.

Owens R J and Young R J. (1994) The genetic engineering of monoclonal antibodies. J. Immunol. Methods 168, 149-165.

Reff M E, Carner K, Chambers K S, Chinn P C, Leonard J E, Raab R, Newman R A, Hanna N and Anderson D R (1994) Depletion of B cells in vivo by a chimeric mouse human monoclonal antibody to CD20. Blood 83, 435-445.

Rees, S, Coote, J, Stables, J, Goodson, S, Harris, S, and Lee, M G. (1996) Bicistronic vector for the creation of stable mammalian cell lines that predisposes all antibiotic-resistant cells to express recombinant protein *Biotechniques* 20, 102-104, 106, 108-110.

Reichmann L, Clark M, Waldmann H and Winter G (1988) Reshaping human antibodies for therapy. Nature 322, 323-327.

Riethmuller G, Riethmuller G, Schneider-Gadicke E, Schlimok G, Schmiegel W, Raab R, Hoffken K, Gruber R, Pichlmaier H, Hirche H, Pichlmayr R, et al. (1994) Randomized trial of monoclonal antibody for adjuvant therapy of resected Dukes' C colorectal carcinoma. Lancet 343, 1177-1183.

Rother R P and Squinto S P (1996) The alpha-Galactosyl epitope: A sugar coating that makes viruses and cells unpalatable. Cell 86, 185-188.

Sanders P. G. and R. H. Wilson (1984) Amplification and cloning of the Chinese hamster glutamine synthetase gene. *EMBO J.* 3:65-71.

Sandhu J S (1992) Protein Engineering of antibodies. Critical Rev Biotechnology 12, 437-462.

Schorpp M., R. Jager, K. Schellander, J. Schenkel, E. F. Wagner, H. Weiher, and P. Angel (1996) The human ubiquitin C promoter directs high ubiquitous expression of transgenes in mice *Nucleic Acids Res.* 24:1787-8.

Shawler D L, Bartholomew R M, Smith L M and Dillman R O (1985) Human immune response to multiple injections of murine monoclonal IgG. J. Immunol. 135, 1530.

Takeuchi M., N. Inoue, T. W. Strickland, M. Kubota, M. Wada, R. Shimizu, S. Hoshi, H. Kozutsumi, S. Takasaki, and A. Kobata (1989) Relationship between sugar chain structure and biological activity of recombinant human erythropoietin produced in Chinese hamster ovary cells. *Proc. Natl. Acad. Sci. U.S.A.* 86:7819-7822.

Urlaub G., E. Kas, A. M. Carothers, and L. A. Chasin (1983) Deletion of the diploid dihydrofolate reductase locus from cultured mammalian cells. *Cell* 33:405-412.

Vandamme A.-M., F. Bulens, H. Bemar, L. Nelles, R. H. Lijnen, and D. Collen (1990) Construction and characterization of a recombinant murine monoclonal antibody directed against human fibrin fragment-D dimer. *Eur. J. Biochem.* 192:767-775.

Vaswani S K and Hamilton R G (1998) Humanized antibodies as potential therapeutic drugs. Ann Allergy, Asthma and Immunol. 81, 105-115.

Vonach B., B. Hess, and C. Leist (1998) Construction of a novel CHO cell line coexpressing human glucosyltransferases and fusion PSGL-1-immunoglobulin G. In: O.-W. Merten et al. (eds), New developments and new applications in animal cell technology, pp. 181-183, Kluwer Academic Publishers.

Weikert S., D. Papac, J. Briggs, D. Cowfer, S. Tom, M. Gawlitzek, J. Lofgren, S. Mehta, V. Chisholm, N. Modi, S. Eppler, K. Carroll, S. Chamow, D. Peers, P. Berman, and L. Krummen (1999) Engineering Chinese hamster ovary cells to maximize sialic acid content of recombinant glycoproteins. *Nature Biotechnology* 17:1116-1121.

White E., P. Sabbatini, M. Debbas, W. S. Wold, D. I. Kusher, and L. R. Gooding (1992) The 19-kilodalton adenovirus E1B transforming protein inhibits programmed cell death and prevents cytolysis by tumor necrosis factor alpha. *Mol. Cell. Biol.* 12:2570-2580.

Winter G, Griffiths A D, Hawkins R E and Hoogenboom H R (1994) Making antibodies by phage display technology. Annu Rev Immunol. 12, 433-455.

Wurm F. and A. Bernard (1999) Large-scale transient expression in mammalian cells for recombinant protein production. *Curr. Opin. Biotechnol.* 10:156-159.

Yamaguchi K., K. Akai, G. Kawanishi, M. Ueda, S. Masuda, and R. Sasaki (1991) Effects of site-directed removal of N-glycosylation sites in human erythropoietin on its production and biological properties. *J. Biol. Chem.* 266: 20434-20439.

Yew P. R. and A. J. Berk (1992) Inhibition of p53 transactivation required for transformation by adenovirus early 1B protein. *Nature* 357:82-85.

Zhang X., S. H. Lok, and O. L. Kom (1998) Stable expression of human alpha-2,6-sialyltransferase in Chinese hamster ovary cells: functional consequences for human erythropoietin expression and bioactivity. *Biochem. Biophys. Acta.* 27:441-452.

What is claimed is:

1. A method for producing a protein of interest, the method comprising:
   a) providing a recombinant adenoviral vector comprising nucleic acid encoding the protein of interest under control of a promoter, wherein said recombinant adenoviral vector has deletions in the E1 and the E2A regions of the adenovirus genome,
   b) propagating said recombinant adenoviral vector in complementing cells that express adenoviral E1 protein and adenoviral E2A protein, to obtain recombinant adenovirus particles,
   c) infecting a culture of complementing cells that express adenoviral E1 protein, but not adenoviral E2A protein, with said recombinant adenovirus particles, to produce the protein of interest, and
   d) harvesting the protein of interest.

2. The method according to claim 1, wherein the complementing cells in step c) comprise PER.C6 cells as deposited at the ECACC under number 96022940.

3. The method according to claim 1, wherein the complementing cells in step b) comprise PER.C6 cells that express the temperature sensitive 125 mutant of E2A (ts125 E2A).

4. The method according to claim 1, wherein the promoter is a cytomegalovirus (CMV) promoter.

5. The method according to claim 1, wherein steps b) and c) are performed in different culture vessels.

6. The method according to claim 1, wherein in step c) the infection of the complementing cells with the recombinant adenovirus particles is performed at a multiplicity of infection (moi) of between 1 and 1000 virus particles (vp)/cell.

7. The method according to claim 6, wherein said moi is between 10 and 100 vp/cell.

8. The method according to claim 1, wherein the recombinant adenovirus particles in step b) are obtained in a culture medium, and wherein the culture medium containing the recombinant adenovirus particles is separated from the complementing cells to obtain a crude adenovirus particle composition, and wherein said crude adenovirus particle composition is used for the infection of step c).

9. The method according to claim 1, wherein the recombinant adenovirus particles in step b) are purified, and subsequently used for the infection of step c).

10. The method according to claim 1, wherein the protein of interest is an antibody.

11. The method according to claim 1, wherein the protein of interest is a blood coagulation protein.

12. The method according to claim 1, wherein the protein of interest is a viral protein other than an adenovirus protein.

13. The method according to claim 12, wherein the protein of interest is influenza hemaglutinin (HA).

14. The method according to claim 1, wherein the protein of interest is erythropoietin (EPO).

15. The method according to claim 1, wherein the complementing cells in step c) are in suspension.

16. A method of producing a protein of interest, the method comprising:
   providing a recombinant adenoviral vector comprising nucleic acid encoding the protein of interest under control of a promoter, wherein said recombinant adenoviral vector has deletions in a first region and in a second region of the adenovirus genome, wherein each of said first second regions is required for adenoviral genome replication and/or adenovirus particle formation;
   propagating said recombinant adenoviral vector in a first type of complementing cells that expresses proteins from said first and from said second regions of the adenovirus genome so as to complement the deletions of the recombinant adenoviral vector, to obtain recombinant adenovirus particles,
   infecting a culture of a second type of complementing cells with said recombinant adenovirus particles, wherein said second type of complementing cells express protein from said first region of the adenovirus genome, but not protein from said second region of the adenovirus genome, to produce the protein of interest; and
   harvesting the protein of interest.

17. A method for producing a protein of interest, the method comprising:
   infecting a culture of complementing cells with a recombinant adenoviral particle that has a genome comprising nucleic acid encoding the protein of interest under control of a promoter to produce the protein of interest,
      wherein said genome has deletions in a first region and in a second region, and each of the first and second regions is required for adenoviral genome replication and/or adenovirus particle formation, and
      wherein said complementing cells express protein from said first region of the genome of the adenoviral particle, but not protein from said second region of the genome of adenoviral particle, and
   harvesting the protein of interest.

18. The method according to claim 17, wherein said first region is E1.

19. A method for producing a protein of interest, the method comprising:
   infecting a culture of complementing cells with a recombinant adenoviral particle that has a genome comprising nucleic acid encoding the protein of interest under control of a promoter to produce the protein of interest,
      wherein said genome has deletions in a first region and in a second region, and each of the first and second regions is required for adenoviral genome replication and/or adenovirus particle formation, and wherein said complementing cells express protein from said first region of the genome of the adenoviral particle, but not protein from said second region of the genome of adenoviral particle, and harvesting the protein of interest, wherein said first region is E1 and wherein said second region is E2A.

20. The method according to claim 17, wherein said complementing cells Comprise PER.C6 cells as deposited at the ECACC under number 96022940.

* * * * *

SEQUENCE LISTING

```
<160> NUMBER OF SEQ ID NOS: 33

<210> SEQ ID NO 1
<211> LENGTH: 41
<212> TYPE: DNA
<213> ORGANISM: Artificial Sequence
<220> FEATURE:
<223> OTHER INFORMATION: PCR Primer-DHFR up, synthesized sequence

<400> SEQUENCE: 1
gatccacgtg agatctccac catggttggt tcgctaaact g                41

<210> SEQ ID NO 2
<211> LENGTH: 37
<212> TYPE: DNA
<213> ORGANISM: Artificial Sequence
<220> FEATURE:
<223> OTHER INFORMATION: PCR Primer-DHFR down, synthesized sequence

<400> SEQUENCE: 2
gatccacgtg agatctttaa tcattcttct catatac                     37

<210> SEQ ID NO 3
<211> LENGTH: 85
<212> TYPE: DNA
<213> ORGANISM: Artificial Sequence
<220> FEATURE:
<223> OTHER INFORMATION: polylinker fragment, synthesized sequence,
      restriction fragment from digestion of pIPspAdapt 6 with AgeI and
      Bam HI

<400> SEQUENCE: 3
accggtgaat tcggcgcgcc gtcgacgata tcgatcggac cgacgcgttc gcgagcggcc    60
gcaattcgct agcgttaacg gatcc                                          85

<210> SEQ ID NO 4
<211> LENGTH: 86
<212> TYPE: DNA
<213> ORGANISM: Artificial Sequence
<220> FEATURE:
```

-continued

```
<223> OTHER INFORMATION: polylinker fragment, synthesized sequence,
      restriction fragment from digestion of pIPspAdapt7 with AgeI and
      Bam HI

<400> SEQUENCE: 4
accggtgaat tgcggccgct cgcgaacgcg tcggtccgta tcgatatcgt cgacggcgcg      60
ccgaattcgc tagcgttaac ggatcc                                          86

<210> SEQ ID NO 5
<211> LENGTH: 43
<212> TYPE: DNA
<213> ORGANISM: Artificial Sequence
<220> FEATURE:
<223> OTHER INFORMATION: PCR Primer-EPO-START, synthesized sequence

<400> SEQUENCE: 5
aaaaaggatc cgccaccatg ggggtgcacg aatgtcctgc ctg                       43

<210> SEQ ID NO 6
<211> LENGTH: 38
<212> TYPE: DNA
<213> ORGANISM: Artificial Sequence
<220> FEATURE:
<223> OTHER INFORMATION: PCR Primer-EPO-STOP, synthesized sequence

<400> SEQUENCE: 6
aaaaaggatc ctcatctgtc ccctgtcctg caggcctc                             38

<210> SEQ ID NO 7
<211> LENGTH: 47
<212> TYPE: DNA
<213> ORGANISM: Artificial Sequence
<220> FEATURE:
<223> OTHER INFORMATION: PCR Primer-LTR-1, synthesized sequence

<400> SEQUENCE: 7
ctgtacgtac cagtgcactg gcctaggcat ggaaaaatac ataactg                   47

<210> SEQ ID NO 8
<211> LENGTH: 64
<212> TYPE: DNA
<213> ORGANISM: Artificial Sequence
<220> FEATURE:
<223> OTHER INFORMATION: PCR Primer-LTR-2, synthesized sequence

<400> SEQUENCE: 8
gcggatcctt cgaaccatgg taagcttggt accgctagcg ttaaccgggc gactcagtca     60
atcg                                                                  64

<210> SEQ ID NO 9
<211> LENGTH: 28
<212> TYPE: DNA
<213> ORGANISM: Artificial Sequence
<220> FEATURE:
<223> OTHER INFORMATION: PCR Primer-HSA1, synthesized sequence

<400> SEQUENCE: 9
gcgccaccat gggcagagcg atggtggc                                        28

<210> SEQ ID NO 10
<211> LENGTH: 50
<212> TYPE: DNA
<213> ORGANISM: Artificial Sequence
<220> FEATURE:
<223> OTHER INFORMATION: PCR Primer-HSA2, synthesized sequence
```

```
<400> SEQUENCE: 10
gttagatcta agcttgtcga catcgatcta ctaacagtag agatgtagaa              50

<210> SEQ ID NO 11
<211> LENGTH: 10
<212> TYPE: DNA
<213> ORGANISM: Artificial Sequence
<220> FEATURE:
<223> OTHER INFORMATION: Oligonucleotide, synthesized sequence, EcoRI
      linker

<400> SEQUENCE: 11
ttaagtcgac                                                          10

<210> SEQ ID NO 12
<211> LENGTH: 10
<212> TYPE: DNA
<213> ORGANISM: Artificial Sequence
<220> FEATURE:
<223> OTHER INFORMATION: oligonucleotide, synthesized sequence, EcoRI
      linker

<400> SEQUENCE: 12
ttaagtcgac                                                          10

<210> SEQ ID NO 13
<211> LENGTH: 23
<212> TYPE: DNA
<213> ORGANISM: Artificial Sequence
<220> FEATURE:
<223> OTHER INFORMATION: oligonucleotide, synthesized sequence, PacI
      linker

<400> SEQUENCE: 13
aattgtctta attaaccgct taa                                           23

<210> SEQ ID NO 14
<211> LENGTH: 67
<212> TYPE: DNA
<213> ORGANISM: Artificial Sequence
<220> FEATURE:
<223> OTHER INFORMATION: oligonucleotide, synthesized sequence, PLL-1

<400> SEQUENCE: 14
gccatcccta ggaagcttgg taccggtgaa ttcgctagcg ttaacggatc ctctagacga   60
gatctgg                                                             67

<210> SEQ ID NO 15
<211> LENGTH: 67
<212> TYPE: DNA
<213> ORGANISM: Artificial Sequence
<220> FEATURE:
<223> OTHER INFORMATION: oligonucleotide, synthesized sequence, PLL-2

<400> SEQUENCE: 15
ccagatctcg tctagaggat ccgttaacgc tagcgaattc accggtacca agcttcctag   60
ggatggc                                                             67

<210> SEQ ID NO 16
<211> LENGTH: 39
<212> TYPE: DNA
<213> ORGANISM: Artificial Sequence
<220> FEATURE:
<223> OTHER INFORMATION: PCR Primer-CMVplus, synthesized sequence
```

```
<400> SEQUENCE: 16
gatcggtacc actgcagtgg tcaatattgg ccattagcc                          39

<210> SEQ ID NO 17
<211> LENGTH: 29
<212> TYPE: DNA
<213> ORGANISM: Artificial Sequence
<220> FEATURE:
<223> OTHER INFORMATION: PCR Primer-CMVminA, synthesized sequence

<400> SEQUENCE: 17
gatcaagctt ccaatgcacc gttcccggc                                     29

<210> SEQ ID NO 18
<211> LENGTH: 34
<212> TYPE: DNA
<213> ORGANISM: Artificial Sequence
<220> FEATURE:
<223> OTHER INFORMATION: PCR Primer-CAMH-UP, synthesized sequence

<400> SEQUENCE: 18
gatcgatatc gctagcacca agggcccatc ggtc                               34

<210> SEQ ID NO 19
<211> LENGTH: 30
<212> TYPE: DNA
<213> ORGANISM: Artificial Sequence
<220> FEATURE:
<223> OTHER INFORMATION: PCR Primer-CAMH-DOWN, synthesized sequence

<400> SEQUENCE: 19
gatcgtttaa actcatttac ccggagacag                                    30

<210> SEQ ID NO 20
<211> LENGTH: 28
<212> TYPE: DNA
<213> ORGANISM: Artificial Sequence
<220> FEATURE:
<223> OTHER INFORMATION: PCR Primer-CAML-UP, synthesized sequence

<400> SEQUENCE: 20
gatccgtacg gtggctgcac catctgtc                                      28

<210> SEQ ID NO 21
<211> LENGTH: 31
<212> TYPE: DNA
<213> ORGANISM: Artificial Sequence
<220> FEATURE:
<223> OTHER INFORMATION: PCR Primer-CAML-DOWN, synthesized sequence

<400> SEQUENCE: 21
gatcgtttaa acctaacact ctcccctgtt g                                  31

<210> SEQ ID NO 22
<211> LENGTH: 20
<212> TYPE: PRT
<213> ORGANISM: Artificial Sequence
<220> FEATURE:
<223> OTHER INFORMATION: leader peptide sequence, synthesized sequence

<400> SEQUENCE: 22

Met Ala Cys Pro Gly Phe Leu Trp Ala Leu Val Ile Ser Thr Cys Leu
1               5                   10                  15

Glu Phe Ser Met
```

<210> SEQ ID NO 23
<211> LENGTH: 60
<212> TYPE: DNA
<213> ORGANISM: Artificial Sequence
<220> FEATURE:
<223> OTHER INFORMATION: oligonucleotide-leader peptide coding sequence, synthesized sequence

<400> SEQUENCE: 23
atggcatgcc ctggcttcct gtgggcactt gtgatctcca cctgtcttga attttccatg    60

<210> SEQ ID NO 24
<211> LENGTH: 38
<212> TYPE: DNA
<213> ORGANISM: Artificial Sequence
<220> FEATURE:
<223> OTHER INFORMATION: PCR Primer-UBS-UP, synthesized sequence

<400> SEQUENCE: 24
gatcacgcgt gctagccacc atggcatgcc ctggcttc                            38

<210> SEQ ID NO 25
<211> LENGTH: 20
<212> TYPE: PRT
<213> ORGANISM: Artificial Sequence
<220> FEATURE:
<223> OTHER INFORMATION: leader peptide, synthesized sequence

<400> SEQUENCE: 25

Met Ala Cys Pro Gly Phe Leu Trp Ala Leu Val Ile Ser Thr Cys Leu
1               5                   10                  15

Glu Phe Ser Met
            20

<210> SEQ ID NO 26
<211> LENGTH: 60
<212> TYPE: DNA
<213> ORGANISM: Artificial Sequence
<220> FEATURE:
<223> OTHER INFORMATION: oligonucleotide-leader peptide coding sequence, synthesized sequence

<400> SEQUENCE: 26
atggcatgcc ctggcttcct gtgggcactt gtgatctcca cctgtcttga attttccatg    60

<210> SEQ ID NO 27
<211> LENGTH: 28
<212> TYPE: DNA
<213> ORGANISM: Artificial Sequence
<220> FEATURE:
<223> OTHER INFORMATION: oligonucleotide, synthesized sequence, PCR product generated using primers UBS-UP and UBSHV-DOWN on template pNUT-Cgamma

<400> SEQUENCE: 27
gatcgctagc tgtcgagacg gtgaccag                                       28

<210> SEQ ID NO 28
<211> LENGTH: 29
<212> TYPE: DNA
<213> ORGANISM: Artificial Sequence
<220> FEATURE:
<223> OTHER INFORMATION: oligonucleotide, synthesized sequence, PCR product generated using primers UBS-UP and UBSLV-DOWN on template pNUT-Ckappa

```
<400> SEQUENCE: 28
gatccgtacg cttgatctcc accttggtc                                      29

<210> SEQ ID NO 29
<211> LENGTH: 50
<212> TYPE: DNA
<213> ORGANISM: Artificial Sequence
<220> FEATURE:
<223> OTHER INFORMATION: PCR Primer-15C5-UP, synthesized sequence

<400> SEQUENCE: 29
gatcacgcgt gctagccacc atgggtactc ctgctcagtt tcttggaatc               50

<210> SEQ ID NO 30
<211> LENGTH: 41
<212> TYPE: DNA
<213> ORGANISM: Artificial Sequence
<220> FEATURE:
<223> OTHER INFORMATION: PCR Primer-HA1 forward primer, synthesized
      sequence

<400> SEQUENCE: 30
attggcgcgc caccatgaag actatcattg ctttgagcta c                        41

<210> SEQ ID NO 31
<211> LENGTH: 39
<212> TYPE: DNA
<213> ORGANISM: Artificial Sequence
<220> FEATURE:
<223> OTHER INFORMATION: PCR Primer-HA1 reverse primer, synthesized
      sequence

<400> SEQUENCE: 31
gatgctagct catctagttt gttttctgg tatattccg                            39

<210> SEQ ID NO 32
<211> LENGTH: 42
<212> TYPE: DNA
<213> ORGANISM: Artificial Sequence
<220> FEATURE:
<223> OTHER INFORMATION: PCR Primer-HA2 reverse primer, synthesized
      sequence

<400> SEQUENCE: 32
gatgctagct cagtctttgt atcctgactt cagttcaaca cc                       42

<210> SEQ ID NO 33
<211> LENGTH: 3052
<212> TYPE: DNA
<213> ORGANISM: Human Adenovirus Type 5
<220> FEATURE:
<223> OTHER INFORMATION: Nucleotides 459-3510 of Human Adenovirus Type 5

<400> SEQUENCE: 33
cgtgtagtgt atttataccc ggtgagttcc tcaagaggcc actcttgagt gccagcgagt    60
agagttttct cctccgagcc gctccgacac cgggactgaa aatgagacat attatctgcc   120
acggaggtgt tattaccgaa gaaatggccg ccagtctttt ggaccagctg atcgaagagg   180
tactggctga taatcttcca cctcctagcc attttgaacc acctaccctt cacgaactgt   240
atgatttaga cgtgacggcc cccgaagatc caacgagga ggcggtttcg cagattttc    300 ccgactctgt aatgttggcg gtgcaggaag ggattgactt actcacttt ccgccggcgc    360 ccggttctcc ggagccgcct caccttccc ggcagcccga gcagccggag cagagagcct   420
```

```
tgggtccggt ttctatgcca aaccttgtac cggaggtgat cgatcttacc tgccacgagg    480
ctggctttcc acccagtgac gacgaggatg aagagggtga ggagtttgtg ttagattatg    540
tggagcaccc cgggcacggt tgcaggtctt gtcattatca ccggaggaat acgggggacc    600
cagatattat gtgttcgctt tgctatatga ggacctgtgg catgtttgtc tacagtaagt    660
gaaaattatg ggcagtgggt gatagagtgg tgggtttggt gtggtaattt tttttttaat    720
ttttacagtt ttgtggttta agaattttg tattgtgatt tttttaaaag gtcctgtgtc    780
tgaacctgag cctgagcccg agccagaacc ggagcctgca agacctaccc gccgtcctaa    840
aatggcgcct gctatcctga dacgcccgac atcacctgtg tctagagaat gcaatagtag    900
tacggatagc tgtgactccg gtccttctaa cacacctcct gagatacacc cggtggtccc    960
gctgtgcccc attaaaccag ttgccgtgag agttggtggg cgtcgccagg ctgtggaatg   1020
tatcgaggac ttgcttaacg agcctgggca acctttggac ttgagctgta aacgccccag   1080
gccataaggt gtaaacctgt gattgcgtgt gtggttaacg cctttgtttg ctgaatgagt   1140
tgatgtaagt ttaataaagg gtgagataat gtttaacttg catggcgtgt taaatggggc   1200
ggggcttaaa gggtatataa tgcgccgtgg gctaatcttg gttacatctg acctcatgga   1260
ggcttgggag tgtttggaag attttttctgc tgtgcgtaac ttgctggaac agagctctaa   1320
cagtacctct tggttttgga ggtttctgtg gggctcatcc caggcaaagt tagtctgcag   1380
aattaaggag gattacaagt gggaatttga agagcttttg aaatcctgtg gtgagctgtt   1440
tgattctttg aatctgggtc accaggcgct tttccaagag aaggtcatca agactttgga   1500
tttttccaca ccggggcgcg ctgcggctgc tgttgctttt ttgagtttta taaggataa   1560 atggagcgaa gaaacccatc tgagcggggg gtacctgctg gattttctgg ccatgcatct   1620
gtggagagcg gttgtgagac acaagaatcg cctgctactg ttgtcttccg tccgcccggc   1680
gataataccg acggaggagc agcagcagca gcaggaggaa gccaggcggc ggcggcagga   1740
gcagagccca tggaacccga gagccggcct ggaccctcgg gaatgaatgt tgtacaggtg   1800
gctgaactgt atccagaact gagacgcatt ttgacaatta cagaggatgg gcaggggcta   1860 aaggggtaa agagggagcg gggggcttgt gaggctacag aggaggctag gaatctagct   1920
tttagcttaa tgaccagaca ccgtcctgag tgtattactt ttcaacagat caaggataat   1980
tgcgctaatg agcttgatct gctggcgcag aagtattcca tagagcagct gaccacttac   2040
tggctgcagc caggggatga ttttgaggag gctattaggg tatatgcaaa ggtggcactt   2100
aggccagatt gcaagtacaa gatcagcaaa cttgtaaata tcaggaattg ttgctacatt   2160
tctgggaacg gggccgaggt ggagatagat acggaggata gggtggcctt tagatgtagc   2220
atgataaata tgtggccggg ggtgcttggc atggacgggg tggttattat gaatgtaagg   2280
tttactggcc ccaattttag cggtacggtt ttcctggcca ataccaacct tatcctacac   2340
ggtgtaagct tctatgggtt taacaatacc tgtgtggaag cctggaccga tgtaagggtt   2400
cggggctgtg cctttactg ctgctggaag ggggtggtgt gtcgcccaa aagcagggct   2460 tcaattaaga aatgcctctt tgaaaggtgt accttggta tcctgtctga gggtaactcc   2520
agggtgcgcc acaatgtggc ctccgactgt ggttgcttca tgctagtgaa aagcgtggct   2580
gtgattaagc ataacatggt atgtggcaac tgcgaggaca gggcctctca gatgctgacc   2640
tgctcggacg gcaactgtca cctgctgaag accattcacg tagccagcca ctctcgcaag   2700
gcctggccag tgtttgagca taacatactg acccgctgtt ccttgcattt gggtaacagg   2760
```

```
aggggggtgt tcctacctta ccaatgcaat ttgagtcaca ctaagatatt gcttgagccc    2820
gagagcatgt ccaaggtgaa cctgaacggg gtgtttgaca tgaccatgaa gatctggaag    2880
gtgctgaggt acgatgagac ccgcaccagg tgcagaccct gcgagtgtgg cggtaaacat    2940
attaggaacc agcctgtgat gctggatgtg accgaggagc tgaggcccga tcacttggtg    3000
ctggcctgca cccgcgctga gtttggctct agcgatgaag atacagattg ag            3052
```